US007589252B2

(12) United States Patent
Huang et al.

(10) Patent No.: US 7,589,252 B2
(45) Date of Patent: Sep. 15, 2009

(54) PLANT TRANSCRIPTION FACTORS AND ENHANCED GENE EXPRESSION

(75) Inventors: Ning Huang, Davis, CA (US); Daichang Yang, Davis, CA (US); Yong-Sic Hwang, Davis, CA (US); Robert J. Schmidt, La Jolla, CA (US)

(73) Assignee: Ventria Bioscience, Sacramento, CA (US)

( * ) Notice: Subject to any disclaimer, the term of this patent is extended or adjusted under 35 U.S.C. 154(b) by 274 days.

(21) Appl. No.: 11/083,617

(22) Filed: Mar. 16, 2005

(65) Prior Publication Data

US 2005/0229273 A1 Oct. 13, 2005

Related U.S. Application Data

(63) Continuation of application No. 09/847,232, filed on May 2, 2001, now abandoned.

(60) Provisional application No. 60/266,920, filed on Feb. 6, 2001, provisional application No. 60/201,182, filed on May 2, 2000.

(51) Int. Cl.
*C12N 15/82* (2006.01)
*C12N 5/04* (2006.01)

(52) U.S. Cl. ........................ 800/278; 800/287; 800/290

(58) Field of Classification Search ................. 800/278, 800/287; 435/69.1
See application file for complete search history.

(56) References Cited

U.S. PATENT DOCUMENTS

| | | | | |
|---|---|---|---|---|
| 4,977,137 | A | 12/1990 | Nichols et al. | |
| 5,543,576 | A | 8/1996 | van Ooijen et al. | |
| 5,589,616 | A * | 12/1996 | Hoffman | 800/294 |
| 5,850,016 | A | 12/1998 | Jung et al. | |
| 5,994,628 | A | 11/1999 | Rodriguez | |
| 6,020,015 | A | 2/2000 | Gaull | |
| 6,160,202 | A * | 12/2000 | Bustos et al. | 800/278 |
| 6,228,623 | B1 * | 5/2001 | Asrar et al. | 435/135 |
| 6,270,827 | B1 | 8/2001 | Gaull et al. | |
| 6,635,806 | B1 | 10/2003 | Kriz et al. | |
| 2002/0192296 | A1 | 12/2002 | Gaull et al. | |
| 2003/0229925 | A1 | 12/2003 | Legrand et al. | |

FOREIGN PATENT DOCUMENTS

| | | |
|---|---|---|
| WO | WO 98/05788 | 2/1998 |
| WO | WO 98/10062 | 3/1998 |
| WO | WO 98/59062 | 12/1998 |
| WO | WO 02/063975 A2 | 8/2002 |

OTHER PUBLICATIONS

Schwechheimer et al (2000, Funct Intergr Genomics 1:35-43).*
Wu et al (1998, Plant Cell Physiol 39(8):885-889).*
Arakawa, T. et al., *Chemicals via Higher Plant Bioengineering*, pp. 149-159, 1999.
Bosch, D. et al., *Transgenic Research* 3:304-310, 1994.
Chong, D.K.X. et al., *Transgenic Research* 6:289-296, 1997.
Lönnerdal, B., *Am. J.. Clin. Nutr.* 63:4, 621S-626S, 1996.
Qiu, J. et al., *Proc. Natl. Acad. Sci. USA* 95:12641-12646, 1998.
Horvath, H. et al., *PNAS* 97(4):1914-1919, 2000.
Lönnerdal, B. and Iyer S., *Annual Reviews Nutr.* 15:93-110, 1995.
Salmon, V. et al., *Protein Expression and Purification* 13:127-135, 1998.
Chong, D. K. X. et al., *Transgenic Research* 9:71-78, 2000.
Lohmann, J. et al., *Cell* 105:793-803, 2001.
Busch, M. et al., *Science* 285:585-587, 1999.
Terashima, M. et al. *Appl. Microbiol Biotechnol.* 52:516-523, 1999.
Schwechheimer et al., *Funct. Intergr Genomics* 1:35-43, 2000.
Izawa et al., *J. Mol. Biol.* 230:1131-1144, 1993.
Hao et al., *The J. of Biological Chemistry* 273(41):26857-26861, 1998.
Okita et al., *J. Biol. Chem.* 264(21):12573-81, 1989, abstract only.
Nakase et al., *Plant Molecular Biology* 33:513-522, 1997.
Russell, D.A. et al., *Transgenic Res.* 6:157-168, 1997.
Genschick, P. et al., *Gene* 148:195-202,1994.
McElroy, D.E. et al., *Plant Cell* 2:163-171, 1990.
Wang, Y. et al., *Molecular Cell Biol.*12(8):3399-3406, 1992.
Washida, H. et al., *Plant Molecular Biol.* 40:1-12, 1999.
Cercós, M. et al., *Plant Journal* 19(2):107-118, 1999.
Holdsworth, M. J. et al., *Plant Molecular Biol.* 29:711-720, 1995.
Schmidt, R. J. et al., *Plant Cell* 4:689-700, 1992.
Wu, C.Y. et al, *Plant Journal* 14(6):673-683, 1998.
Mena, M.I. et al, *Plant Journal* 16(1):53-62, 1998.
Vicente-Carbajosa, V. et al., *Plant Journal* 13(5):629-640, 1998.
Albani, D. et al., *Plant Cell* 9:171-184, 1997.
Muller, M. et al., *J. Plant Physiol.* 145:606-613, 1995.
Vincente-Carbajosa, J. et al., *Proc. Natl. Acad. Sci. USA* 94:7685-7690, 1997.
Muller et al., *Plant Mol. Biol.*, 33(3):513-522, 1997.
Liu et al., *NCBI Accession No.* AY387493, 2003.
Nakase et al., GenBank Accession No. AB021736 Oryza sativa gene for bZIP protein, complete cds (1998).

(Continued)

*Primary Examiner*—Stuart F. Baum
(74) *Attorney, Agent, or Firm*—Susan J. Meyers Fitch; Peter J. Dehlinger; King & Spalding LLP

(57) ABSTRACT

The invention relates to transgenic plants that demonstrate enhanced expression of a plant transcription factor under the control of a seed specific promoter such that expression of the transcription factor activates transcription of a native or non-native coding sequence in the plant. The invention further relates to a method of generating such transgenic plants and methods for enhancing the level of expression of a selected heterologous protein in seeds of such transgenic plants.

4 Claims, 31 Drawing Sheets

OTHER PUBLICATIONS

Yamagata et al., GenBank Accession No. D11385 Oryza sativa mRNA for prolamin, complete cds (1992).

Schmidt et al., GenBank Accession No. M29411 Z. mays DNA binding protein opaque-2 (02) mRNA, complete cds (1990).

Vincente-Carbajosa et al., GenBank Accession No. U82230 Zea mays endosperm-specific prolamin box binding factor (PBF) mRNA, complete cds (1996).

Maddaloni etal., GenBank Accession No. X15544 Zea mays opaque-2 gene (1989).

* cited by examiner

```
        10         20         30         40         50         60         70
GGTACCCATC TAATACATTA ATAACAAGAG AGAGAATGGA TAATGCAATT ATTTATTTTT ATGGGAGGCT
CCATGGGTAG ATTATGTAAT TATTGTTCTC TCTCTTACCT ATTACGTTAA TAAATAAAAA TACCCTCCGA

        80         90        100        110        120        130        140
ATATTTTTAT CGGATTTTAG TAAATAACGG GGCAATTCGG TACTTAGGTA AAGCTACGTA TGACTATCGC
TATAAAAATA GCCTAAAATC ATTTATTGCC CCGTTAAGCC ATGAATCCAT TTCGATGCAT ACTGATAGCG

       150        160        170        180        190        200        210
TACCGCTACG GTAGTTGAAT TGGAATTCTT CGATAGCATC TGTTGTGTTG TTGCAGTTAG GGTACTTGAA
ATGGCGATGC CATCAACTTA ACCTTAAGAA GCTATCGTAG ACAACACAAC AACGTCAATC CCATGAACTT

       220        230        240        250        260        270        280
TAGCTCCAGC CGTGAAAACG AGGGGTTTTC GCAGGTTTTA TAGGATTGCC AAGTTAGACT AGGGCAATTC
ATCGAGGTCG GCACTTTTGC TCCCCAAAAG CGTCCAAAAT ATCCTAACGG TTCAATCTGA TCCCGTTAAG

       290        300        310        320        330        340        350
ATGTTCACGG TATTGTGTAG TATATGAAAA AGGAGATCTC CCAAACAATT TATAATTTTG TATAAGGGAG
TACAAGTGCC ATAACACATC ATATACTTTT TCCTCTAGAG GGTTTGTTAA ATATTAAAAC ATATTCCCTC

                                            >AT-rich_region_

       360        370        380        390        400        410        420
AAATCGAACT TGAGGTGTCT AATTCACCAA CCGAGCTACT CCCTCCGTTT CATATATGTA TATACATATA
TTTAGCTTGA ACTCCACAGA TTAAGTGGTT GGCTCGATGA GGGAGGCAAA GTATATACAT ATATGTATAT

       430        440        450        460        470        480        490
TACGTATATA TACGTATATA CACATATACG TATATACATA TATGGTATAT ACATATATAT ATATATATAT
ATGCATATAT ATGCATATAT GTGTATATGC ATATATGTAT ATACCATATA TGTATATATA TATATATATA

       500        510        520        530        540        550        560
ATATATATAT ATGTGTGTGT GTGTATGTGG GGTGGCAATG CTAAAAAGTT TTATAATATG AACGGATGAA
TATATATATA TACACACACA CACATACACC CCACCGTTAC GATTTTTCAA AATATTATAC TTGCCTACTT

       570        580        590        600        610        620        630
GTACTATCCA CTAAGTCCCT ATAGTTTTCT GGCACTGTGT AGTATACGAA TGCACAATTA TATCCATAAA
CATGATAGGT GATTCAGGGA TATCAAAAGA CCGTGACACA TCATATGCTT ACGTGTTAAT ATAGGTATTT

       640        650        660        670        680        690        700
ATTGATATTA TATATTCGTC GCGACGAAAA TAAAGACATA ATATTCGGTA TACCATTTAT CCACGATATA
TAACTATAAT ATATAAGCAG CGCTGCTTTT ATTTCTGTAT TATAAGCCAT ATGGTAAATA GGTGCTATAT

       710        720        730        740        750        760        770
TCTAAATTCC ACTGATATAT CTAAATTCCA CTTGATCCCT TTTATGGATA AATTCTGGAT AACAATTACT
AGATTTAAGG TGACTATATA GATTTAAGGT GAACTAGGGA AAATACCTAT TTAAGACCTA TTGTTAATGA

       780        790        800        810        820        830        840
ACCAGCAGTA TATCCTACTA TCAGCGCACT GCACACCAAA CTACCCTCAC CCAGTAGTTA CAAACGCATA
TGGTCGTCAT ATAGGATGAT AGTCGCGTGA CGTGTGGTTT GATGGGAGTG GGTCATCAAT GTTTGCGTAT
```

Fig. 2A

```
       850        860        870        880        890        900        910
TTTTGCCGTT AGTTAATTAT TATCCGGTAA AGAAGGTAAA GAAGATTGGT AGTAATCCAA AATTTTCCCA
AAAACGGCAA TCAATTAATA ATAGGCCATT TCTTCCATTT CTTCTAACCA TCATTAGGTT TTAAAAGGGT

       920        930        940        950        960        970        980
ACCCCAACCT CGGAACAAAA ACCGCGTAGT ATTTGTCGTA ACCAGGAGCA TCCGAGTCAT TAATTTACAC
TGGGGTTGGA GCCTTGTTTT TGGCGCATCA TAAACAGCAT TGGTCCTCGT AGGCTCAGTA ATTAAATGTG

                 >Transcription_start_site
>CAAG_site
                           |                                            |
       990       1000       1010       1020       1030       1040       1050
CCAAACACAA AAAATTAGCA GCACGCAGCC GCCTTCCCAA TCCTCTCCTC TCTCCTCTCC TCTTCTCCAA
GGTTTGTGTT TTTTAATCGT CGTGCGTCGG CGGAAGGGTT AGGAGAGGAG AGAGGAGAGG AGAAGAGGTT

      1060       1070       1080       1090       1100       1110       1120
GCGGCAATTC GCGCGAGGTT TTCTCCGATC AAACCCTCGA ATCCCCCCCT CGCGAATCCA TCGGAGGGTA
CGCCGTTAAG CGCGCTCCAA AAGAGGCTAG TTTGGGAGCT TAGGGGGGGA GCGCTTAGGT AGCCTCCCAT

      1130       1140       1150       1160           1170        1180
GCCCCGCGAT CCGCGTCGGC GAGAGCGGAT TCCGATTCCG CG ATG GAG CGG GTG TTC TCC GTG
CGGGGCGCTA GGCGCAGCCG CTCTCGCCTA AGGCTAAGGC GC TAC CTC GCC CAC AAG AGG CAC
                                               M   E   R   V   F   S   V>
                                             ____a___a__EXON1_____a___a___>

     1190        1200        1210         1220        1230        1240
GAG GAG ATC TCC GAC CCA TTC TGG GTC CCG CCT CCG CCG CCG CAG TCG GCG GCG GCG
CTC CTC TAG AGG CTG GGT AAG ACC CAG GGC GGA GGC GGC GGC GTC AGC CGC CGC CGC
 E   E   I   S   D   P   F   W   V   P   P   P   P   P   Q   S   A   A   A>
____a___a___a___a___a___a___a___a__EXON1_____a___a___a___a___a___a___a___a___>

        1250        1260        1270         1280        1290
GCC CAG CAG CAG GGC GGC GGC GGC GTG GCT TCG GGA GGT GGT GGT GGT GTA GCG GGG
CGG GTC GTC GTC CCG CCG CCG CCG CAC CGA AGC CCT CCA CCA CCA CCA CAT CGC CCC
 A   Q   Q   Q   G   G   G   G   V   A   S   G   G   G   G   G   V   A   G>
____a___a___a___a___a___a___a___a__EXON1_____a___a___a___a___a___a___a___a___>

1300        1310         1320        1330         1340        1350
GGC GGC GGC GGC GGG AAC GCG ATG AAC CGG TGC CCG TCG GAG TGG TAC TTC CAG AAG
CCG CCG CCG CCG CCC TTG CGC TAC TTG GCC ACG GGC AGC CTC ACC ATG AAG GTC TTC
 G   G   G   G   G   N   A   M   N   R   C   P   S   E   W   Y   F   Q   K>
____a___a___a___a___a___a___a___a__EXON1_____a___a___a___a___a___a___a___a___>

   1360        1370        1380        1390         1400        1410
TTT CTG GAG GAG GCG GTG CTC GAT AGC CCC GTC CCG AAC CCT AGC CCG AGG GCC GAA
AAA GAC CTC CTC CGC CAC GAG CTA TCG GGG CAG GGC TTG GGA TCG GGC TCC CGG CTT
 F   L   E   E   A   V   L   D   S   P   V   P   N   P   S   P   R   A   E>
____a___a___a___a___a___a___a___a__EXON1_____a___a___a___a___a___a___a___a___>
```

Fig. 2B

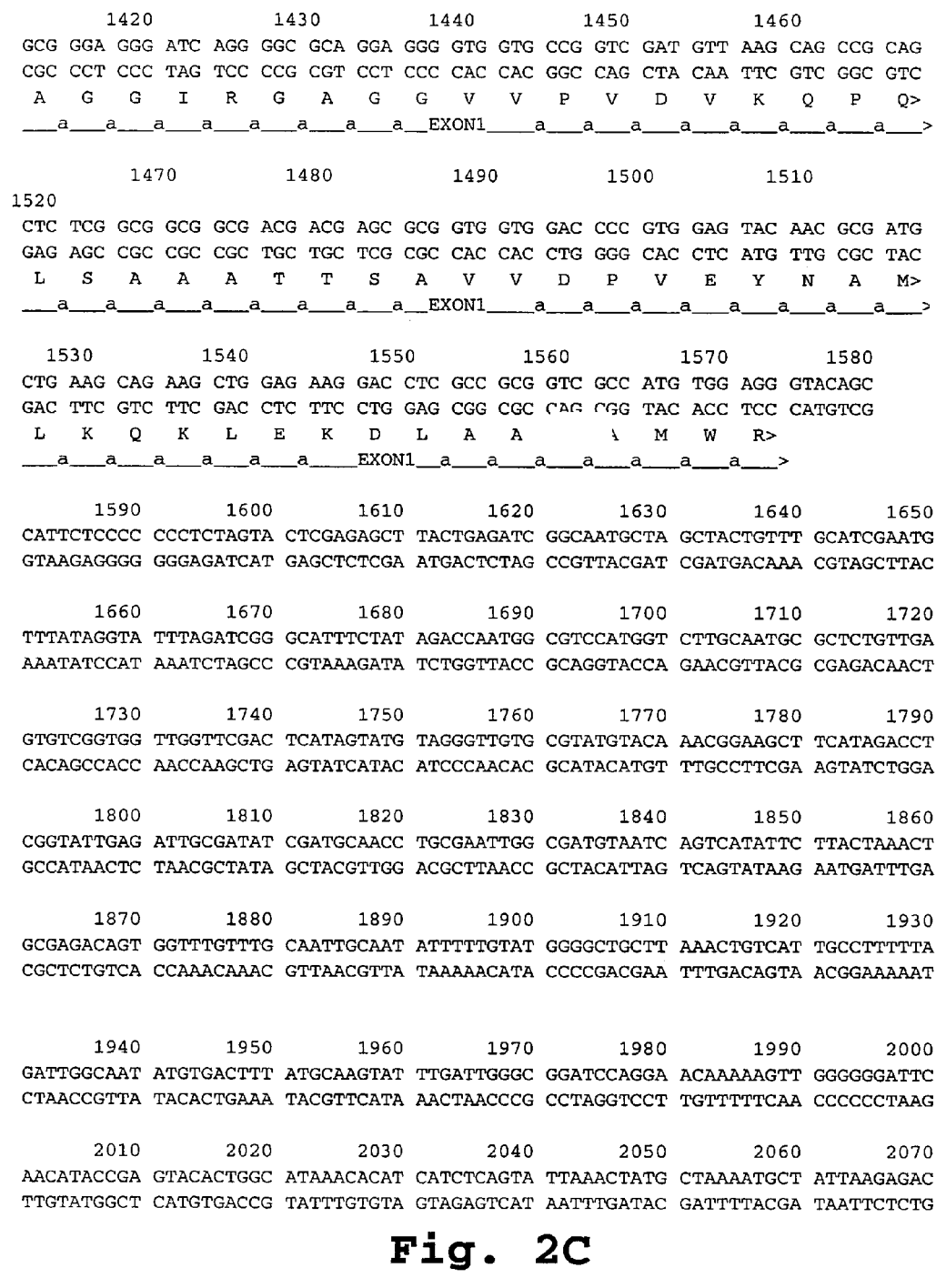

```
         1420        1430        1440        1450        1460
GCG GGA GGG ATC AGG GGC GCA GGA GGG GTG GTG CCG GTC GAT GTT AAG CAG CCG CAG
CGC CCT CCC TAG TCC CCG CGT CCT CCC CAC CAC GGC CAG CTA CAA TTC GTC GGC GTC
 A   G   G   I   R   G   A   G   G   V   V   P   V   D   V   K   Q   P   Q>
___a___a___a___a___a___a___a___a__EXON1____a___a___a___a___a___a___a___a___>

         1470        1480        1490        1500        1510
1520
CTC TCG GCG GCG GCG ACG ACG AGC GCG GTG GTG GAC CCC GTG GAG TAC AAC GCG ATG
GAG AGC CGC CGC CGC TGC TGC TCG CGC CAC CAC CTG GGG CAC CTC ATG TTG CGC TAC
 L   S   A   A   A   T   T   S   A   V   V   D   P   V   E   Y   N   A   M>
___a___a___a___a___a___a___a___a__EXON1____a___a___a___a___a___a___a___a___>

    1530        1540        1550        1560        1570        1580
CTG AAG CAG AAG CTG GAG AAG GAC CTC GCC GCG GTC GCC ATG TGG AGG GTACAGC
GAC TTC GTC TTC GAC CTC TTC CTG GAG CGG CGC CAG CGG TAC ACC TCC CATGTCG
 L   K   Q   K   L   E   K   D   L   A   A   V   A   M   W   R>
___a___a___a___a___a___a_____EXON1___a___a___a___a___a___a___a___>

    1590        1600        1610        1620        1630        1640        1650
CATTCTCCCC CCCTCTAGTA CTCGAGAGCT TACTGAGATC GGCAATGCTA GCTACTGTTT GCATCGAATG
GTAAGAGGGG GGGAGATCAT GAGCTCTCGA ATGACTCTAG CCGTTACGAT CGATGACAAA CGTAGCTTAC

    1660        1670        1680        1690        1700        1710        1720
TTTATAGGTA TTTAGATCGG GCATTTCTAT AGACCAATGG CGTCCATGGT CTTGCAATGC GCTCTGTTGA
AAATATCCAT AAATCTAGCC CGTAAAGATA TCTGGTTACC GCAGGTACCA GAACGTTACG CGAGACAACT

    1730        1740        1750        1760        1770        1780        1790
GTGTCGGTGG TTGGTTCGAC TCATAGTATG TAGGGTTGTG CGTATGTACA AACGGAAGCT TCATAGACCT
CACAGCCACC AACCAAGCTG AGTATCATAC ATCCCAACAC GCATACATGT TTGCCTTCGA AGTATCTGGA

    1800        1810        1820        1830        1840        1850        1860
CGGTATTGAG ATTGCGATAT CGATGCAACC TGCGAATTGG CGATGTAATC AGTCATATTC TTACTAAACT
GCCATAACTC TAACGCTATA GCTACGTTGG ACGCTTAACC GCTACATTAG TCAGTATAAG AATGATTTGA

    1870        1880        1890        1900        1910        1920        1930
GCGAGACAGT GGTTTGTTTG CAATTGCAAT ATTTTTGTAT GGGGCTGCTT AAACTGTCAT TGCCTTTTTA
CGCTCTGTCA CCAAACAAAC GTTAACGTTA TAAAAACATA CCCCGACGAA TTTGACAGTA ACGGAAAAAT

    1940        1950        1960        1970        1980        1990        2000
GATTGGCAAT ATGTGACTTT ATGCAAGTAT TTGATTGGGC GGATCCAGGA ACAAAAAGTT GGGGGGATTC
CTAACCGTTA TACACTGAAA TACGTTCATA AACTAACCCG CCTAGGTCCT TGTTTTTCAA CCCCCCTAAG

    2010        2020        2030        2040        2050        2060        2070
AACATACCGA GTACACTGGC ATAAACACAT CATCTCAGTA TTAAACTATG CTAAAATGCT ATTAAGAGAC
TTGTATGGCT CATGTGACCG TATTTGTGTA GTAGAGTCAT AATTTGATAC GATTTTACGA TAATTCTCTG
```

Fig. 2C

```
              2080       2090       2100       2110       2120       2130       2140
         CTTTAGCACC TCTTATCTTA TCAACCATGG TGAAAAAATT GAAGGGGGGA CTCAGGGGGG TATCCATGGG
         GAAATCGTGG AGAATAGAAT AGTTGGTACC ACTTTTTTAA CTTCCCCCCT GAGTCCCCCC ATAGGTACCC

              2150       2160       2170       2180       2190       2200       2210
         TCCGATGGGT GCAGGGGGGA CTGAGTCCCC CCTGCACCCA CGTTGAATCC GCCCTGGCAT GCGTATAAGC
         AGGCTACCCA CGTCCCCCCT GACTCAGGGG GGACGTGGGT GCAACTTAGG CGGGACCGTA CGCATATTCG

              2220       2230       2240       2250       2260       2270       2280
         TGTCACAGCC ATTTCTAGGT GCTTGTGCTT AGTTGGGTGA TGTCAGCTTA ATTTGTCTTT TCTATGTCGT
         ACAGTGTCGG TAAAGATCCA CGAACACGAA TCAACCCACT ACAGTCGAAT TAAACAGAAA AGATACAGCA

              2290       2300       2310       2320       2330       2340       2350
         CATCGATTTT CTAAGAAACG AAAAATAGCC TATTTATGTG CTCCAGAATT TGATGATCCC TGGCCCTTCA
         GTAGCTAAAA GATTCTTTGC TTTTTATCGG ATAAATACAC GAGGTCTTAA ACTACTAGGG ACCGGGAAGT

              2360       2370       2380       2390       2400       2410       2420
         TTTGCTGAAA TTAGCCTATT TGTTGGTTGC CCTTCAGTTT TTTCCCAGCT TATGTTGTTG CAATGTGTGG
         AAACGACTTT AATCGGATAA ACAACCAACG GGAAGTCAAA AAAGGGTCGA ATACAACAAC GTTACACACC

              2430       2440       2450       2460       2470       2480       2490
         CTATGCCTCG TTTTGTGCCC TATAATTTAT TATTTGCAAT TCATTTTTGT ACATGACTTA AAATGACACT
         GATACGGAGC AAAACACGGG ATATTAAATA ATAAACGTTA AGTAAAAACA TGTACTGAAT TTTACTGTGA

              2500       2510       2520       2530       2540       2550       2560
         AGAGCAACAT GCACTGATTG GTTATCCTAT AATCATTTAT GTAGTTCTGT TCATTTTATC ATGCTAGCTC
         TCTCGTTGTA CGTGACTAAC CAATAGGATA TTAGTAAATA CATCAAGACA AGTAAAATAG TACGATCGAG

              2570       2580       2590       2600       2610       2620
         ATGTCATTTT CATCTTCAG GCC TCT GGC ACA GTT CCA CCT GAG CGT CCT GGA GCT GGT TCA
         TACAGTAAAA GTAGAAGTC CGG AGA CCG TGT CAA GGT GGA CTC GCA GGA CCT CGA CCA AGT
                              A   S   G   T   V   P   P   E   R   P   G   A   G   S>
                         __b___b___b___b___b_____EXON2_b___b___b___b___b___b___>

              2630       2640       2650       2660       2670       2680
         TCC TTG CTG AAT GCA GAT GTT TCA CAC ATA GGC GCT CCT AAT TCC ATC GGA GGTACTTA
         AGG AAC GAC TTA CGT CTA CAA AGT GTG TAT CCG CGA GGA TTA AGG TAG CCT CCATGAAT
          S   L   L   N   A   D   V   S   H   I   G   A   P   N   S   I   G>
         __b___b___b___b___b___b___b___b__EXON2____b___b___b___b___b___b___b___>

              2690       2700       2710       2720       2730       2740       2750
         TCTTATCTGG TTACATTTTC AGATTGTTAT GAAACTACCC AAATATCCTG CACAATTGCA TGGGATTAAA
         AGAATAGACC AATGTAAAAG TCTAACAATA CTTTGATGGG TTTATAGGAC GTGTTAACGT ACCCTAATTT
```

Fig. 2D

```
      2760       2770       2780       2790       2800       2810       2820
TTTTAGTTTC TTTGAAATAG AAGTAGAGTT GTATTGCTGT CACGTCATCA AATAGTTCTG AAGCTATGAA
AAAATCAAAG AAACTTTATC TTCATCTCAA CATAACGACA GTGCAGTAGT TTATCAAGAC TTCGATACTT

      2830       2840       2850       2860       2870       2880       2890
TAAATAAGTT CCGCATTTGT TAGTGATTCT TTGAACATTA GAATTGTTAT GCTTAAGTAG ATAGGGTTAT
ATTTATTCAA GGCGTAAACA ATCACTAAGA AACTTGTAAT CTTAACAATA CGAATTCATC TATCCCAATA

      2900       2910       2920       2930       2940       2950       2960
GTTTGTTTGG AGTTCCCTTA AATCATTTCA TTGCTGACTG CCAGCTGGCA GGAGCATTTG TTGTTGCCTT
CAAACAAACC TCAAGGGAAT TTAGTAAAGT AACGACTGAC GGTCGACCGT CCTCGTAAAC AACAACGGAA

      2970       2980       2990       3000       3010       3020       3030
GACCATGAAT GAAGACCTTC CTGTTCTGAG TGCTCACAAG AAAACATATT TTGATTAATG CACCTTGAAT
CTGGTACTTA CTTCTGGAAG GACAAGACTC ACGAGTGTTC TTTTGTATAA AACTAATTAC GTGGAACTTA

      3040       3050       3060       3070       3080       3090       3100
CCTTAGGATC TTGCAAAGAT GGGCACTTAG CTTTAGAATT GAGTAGTACT TAAATAGCTG TTGTTATCAT
GGAATCCTAG AACGTTTCTA CCCGTGAATC GAAATCTTAA CTCATCATGA ATTTATCGAC AACAATAGTA

      3110       3120       3130       3140       3150       3160       3170
GATTTGTCCT GTAGTGAAAT GTCGACAAAA CAGGAATGCT ACTTTTGACT TCTGATATTT CATGCCTGGC
CTAAACAGGA CATCACTTTA CAGCTGTTTT GTCCTTACGA TGAAAACTGA AGACTATAAA GTACGGACCG

      3180       3190       3200         3210          3220         3230
TTTACTTATG CTCTGTTTGG AACATGGGCA CATATCA GGC AAT GCT ACT CCA GTT CAA AAC ATG
AAATGAATAC GAGACAAACC TTGTACCCGT GTATAGT CCG TTA CGA TGA GGT CAA GTT TTG TAC
                                          G   N   A   T   P   V   Q   N   M>
                                        ____c___c___c__EXON3 ___c___c___c___>

  3240          3250        3260        3270          3280        3290
CTA AGT GGC CCA AGT GGG GGA TCG GGC TCA CAG TTG GTA CAG AAT GTT GAT GTC CTT
GAT TCA CCG GGT TCA CCC CCT AGC CCG AGT GTC AAC CAT GTC TTA CAA CTA CAG GAA
 L   S   G   P   S   G   G   S   G   S   Q   L   V   Q   N   V   D   V   L>
___c___c___c___c___c___c___c___c__EXON3 ___c___c___c___c___c___c___c___c___>

     3300         3310        3320        3330         3340
GTA AAG CAG CCC ACC AGC TCT TCA TCA AGG GAG CAG TCA GAT GAT GAT GAC ATG AAG
CAT TTC GTC GGG TGG TCG AGA AGT AGT TCC CTC GTC AGT CTA CTA CTA CTG TAC TTC
 V   K   Q   P   T   S   S   S   S   R   E   Q   S   D   D   D   D   M   K>
___c___c___c___c___c___c___c___c__EXON3 ___c___c___c___c___c___c___c___c___>

3350       3360          3370        3380        3390         3400
GGA GAA GCT GAG ACC ACT GGA ACT GCA AGA CCT GCT GAT CAA AGA TTA CAA CGA
CCT CTT CGA CTC TGG TGA CCT TGA CGT TCT GGA CGA CTA GTT TCT AAT GTT GCT
 G   E   A   E   T   T   G   T   A   R   P   A   D   Q   R   L   Q   R>
___c___c___c___c___c___c___c____EXON3 _c___c___c___c___c___c___c___c___>
```

Fig. 2E

```
     3410       3420       3430       3440       3450       3460       3470
AGGTGATC ATTCATTGCT TCCTTGTAAT ATAGATTCTG TACATAATTA ACCTACCTCG TCATGCATGC
TCCACTAG TAAGTAACGA AGGAACATTA TATCTAAGAC ATGTATTAAT TGGATGGAGC AGTACGTACG

      3480       3490       3500       3510       3520       3530       3540
ATGTGTCCTA TTTTCACCTT AGCCCTTTCA GTTGGATTTC CACTTTCATC CGGTAGCCTT TCAGTTTCCT
TACACAGGAT AAAAGTGGAA TCGGGAAAGT CAACCTAAAG GTGAAAGTAG GCCATCGGAA AGTCAAAGGA

      3550       3560       3570       3580       3590       3600       3610
ATTGCATCGC ATATATGATC TTTTACCTAC CATATTAGTT CTCTGTGTGC CATACTCAGT GCTTAGTGTC
TAACGTAGCG TATATACTAG AAAATGGATG GTATAATCAA GAGACACACG GTATGAGTCA CGAATCACAG

      3620       3630       3640       3650       3660       3670       3680
TCGAGCAAGA GAGGAATTTG TATGGCTATT ACACGTAGCA CTTTGCTCTC TACTTGTTTA TTGACATAAG
AGCTCGTTCT CTCCTTAAAC ATACCGATAA TGTGCATCGT GAAACGAGAG ATGAACAAAT AACTGTATTC

      3690       3700       3710       3720       3730       3740       3750
CAATTTGGGA TGAATTAAAT CTGAGTTCAC ATCATATTCC TTATGTCACA AGTTTCTGAA ACCGATTGTA
GTTAAACCCT ACTTAATTTA GACTCAAGTG TAGTATAAGG AATACAGTGT TCAAAGACTT TGGCTAACAT

      3760       3770       3780       3790       3800       3810       3820
TCTAGTATCT GGTTGATGCA CCCCCATCTT GGATTTGCAA ATCAAAGTTA TACTCCCTAG AGAGCTTTAC
AGATCATAGA CCAACTACGT GGGGGTAGAA CCTAAACGTT TAGTTTCAAT ATGAGGGATC TCTCGAAATG

      3830       3840       3850       3860       3870       3880       3890
CTTTCATAAA GCAATTACCC CAATAAACCA CGGATTTGAT AGCTATTGAC TATGATTACC AGAATTCATT
GAAAGTATTT CGTTAATGGG GTTATTTGGT GCCTAAACTA TCGATAACTG ATACTAATGG TCTTAAGTAA

      3900       3910       3920       3930       3940       3950       3960
TGGCAGCTAT TTTCTCAATT TAAGTTTGGT ATTAGTCTCA GTTGGCTGTA AAATAATGTC ACGGTAGGGT
ACCGTCGATA AAAGAGTTAA ATTCAAACCA TAATCAGAGT CAACCGACAT TTTATTACAG TGCCATCCCA

      3970       3980       3990       4000       4010       4020       4030
ACATGTATGT GCAGCATACA AGGTATGGGT GAGTTATGAT ATGGACAGTG TGTACACCCC ACATTTGCTC
TGTACATACA CGTCGTATGT TCCATACCCA CTCAATACTA TACCTGTCAC ACATGTGGGG TGTAAACGAG

      4040       4050       4060       4070       4080       4090       4100
ACTAAAATCA AAATATTCAA ACGTCACGTG ATGATATGGT GGATTGCATT ATACCTTGTA TTGTTTATTA
TGATTTTAGT TTTATAAGTT TGCAGTGCAC TACTATACCA CCTAACGTAA TATGGAACAT AACAAATAAT

      4110       4120       4130       4140       4150       4160       4170
TGTTACTTGT GCTAGACAAT AATATAGGCT GTTCTTTTGG GTGATTTTGT ATGAAGATGT TGAGCAAGCA
ACAATGAACA CGATCTGTTA TTATATCCGA CAAGAAAACC CACTAAAACA TACTTCTACA ACTCGTTCGT

      4180       4190       4200         4210         4220         4230
CTTCTCGATA TAATGCTAGT TTTGTTGACC TGTTCC AGG AAG CAA TCC AAT CGG GAG TCA GCC
GAAGAGCTAT ATTACGATCA AAACAACTGG ACAAGG TCC TTC GTT AGG TTA GCC CTC AGT CGG
                                         R   K   Q   S   N   R   E   S   A>
                                        ___d___d___d__EXON4_____d___d___d___>
```

Fig. 2F

```
    4240        4250        4260        4270        4280        4290
AGG CGC TCA AGA AGC AGA AAG GCA GCT CAC TTG AAT GAG CTG GAG GCA CAG GTGTGA
TCC GCG AGT TCT TCG TCT TTC CGT CGA GTG AAC TTA CTC GAC CTC CGT GTC CACACT
 R   R   S   R   S   R   K   A   A   H   L   N   E   L   E   A   Q>
___d___d___d___d___d___d___d__EXON4____d___d___d___d___d___d___d___>

     4300       4310       4320       4330       4340       4350       4360
TAGTTCACAT AGTTATTTTC GATAAGACAT AAAATCCTAA ATTACTGGCT ACTGACTTCA GTTATGGATT
ATCAAGTGTA TCAATAAAAG CTATTCTGTA TTTTAGGATT TAATGACCGA TGACTGAAGT CAATACCTAA

     4370         4380        4390        4400        4410        4420
TACTTGTTAC AG GTA TCG CAA TTA AGA GTC GAG AAC TCC TCG CTG TTA AGG CGT CTT GCT
ATGAACAATG TC CAT AGC GTT AAT TCT CAG CTC TTG AGG AGC GAC AAT TCC GCA GAA CGA
              V   S   Q   L   R   V   E   N   S   S   L   L   R   R   L   A>
             ___e___e___e___e___e___e____EXON5__e___e___e___e___e___e___e___>

       4430        4440        4450        4460        4470
GAT GTT AAC CAG AAG TAC AAT GAT GCT GCT GTT GAC AAT AGA GTG CTA AAA GCA GAT
CTA CAA TTG GTC TTC ATG TTA CTA CGA CGA CAA CTG TTA TCT CAC GAT TTT CGT CTA
 D   V   N   Q   K   Y   N   D   A   A   V   D   N   R   V   L   K   A   D>
___e___e___e___e___e___e___e___e__EXON5____e___e___e___e___e___e___e___e___>

4480        4490        4500       4510       4520       4530       4540
GTT GAG ACC TTG AGA GCA AAG GT ATGCTATATA TGCCTTTTGC AATATGCATC CCATGGATTG
CAA CTC TGG AAC TCT CGT TTC CA TACGATATAT ACGGAAAACG TTATACGTAG GGTACCTAAC
 V   E   T   L   R   A   K>
___e___e__EXON5____e___e___>

     4550       4560       4570       4580       4590       4600       4610
CTACTTTGGC TTGTTTCAAA CTTTCAACGT GACTTGTGTA CCCTGTTATT AGAAGAATAA TCCCGCCTAC
GATGAAACCG AACAAAGTTT GAAAGTTGCA CTGAACACAT GGGACAATAA TCTTCTTATT AGGGCGGATG

     4620       4630       4640       4650       4660       4670       4680
CATTATACTC TATAAATCAC CATTTGGCCA GTCCAAACAT GATTATTAAA TCAGGTCAAT CTGAACATTG
GTAATATGAG ATATTTAGTG GTAAACCGGT CAGGTTTGTA CTAATAATTT AGTCCAGTTA GACTTGTAAC

     4690       4700       4710        4720        4730        4740
AAATGTATCA AAAATTCGCA GGTG AAG ATG GCA GAG GAC TCG GTG AAG CGG GTG ACA GGC
TTTACATAGT TTTTAAGCGT CCAC TTC TAC CGT CTC CTG AGC CAC TTC GCC CAC TGT CCG
                            K   M   A   E   D   S   V   K   R   V   T   G>
                           ___f___f___f___f____EXON6__f___f___f___f___f___>

       4750        4760        4770        4780        4790
ATG AAC GCG TTG TTT CCC GCC GCT TCT GAT ATG TCA TCC CTC AGC ATG CCA TTC AAC
TAC TTG CGC AAC AAA GGG CGG CGA AGA CTA TAC AGT AGG GAG TCG TAC GGT AAG TTG
 M   N   A   L   F   P   A   A   S   D   M   S   S   L   S   M   P   F   N>
___f___f___f___f___f___f___f___f__EXON6____f___f___f___f___f___f___f___f___>
```

Fig. 2G

```
4800       4810       4820       4830       4840       4850
AGC TCC CCA TCT GAA GCA ACG TCA GAC GCT GCT GTT CCC ATC CAA GAT GAC CCG AAC
TCG AGG GGT AGA CTT CGT TGC AGT CTG CGA CGA CAA GGG TAG GTT CTA CTG GGC TTG
 S   S   P   S   E   A   T   S   D   A   A   V   P   I   Q   D   D   P   N>
___f___f___f___f___f___f___f___f__EXON6____f___f___f___f___f___f___f___f___>

  4860       4870       4880       4890       4900       4910
AAT TAC TTC GCT ACT AAC AAC GAC ATC GGA GGT AAC AAC AAC TAC ATG CCC GAC ATA
TTA ATG AAG CGA TGA TTG TTG CTG TAG CCT CCA TTG TTG TTG ATG TAC GGG CTG TAT
 N   Y   F   A   T   N   N   D   I   G   G   N   N   N   Y   M   P   D   I>
___f___f___f___f___f___f___f___f__EXON6____f___f___f___f___f___f___f___f___>

     4920       4930       4940       4950       4960
CCT TCT TCG GCT CAG GAG GAC GAG GAC TTC GTC AAT GGC GCT CTG GCT GCC GGC AAG
GGA AGA AGC CGA GTC CTC CTG CTC CTG AAG CAG TTA CCG CGA GAC CGA CGG CCG TTC
 P   S   S   A   Q   E   D   E   D   F   V   N   G   A   L   A   A   G   K>
___f___f___f___f___f___f___f___f__EXON6____f___f___f___f___f___f___f___f___>

       4970       4980       4990       5000       5010
5020
ATT GGC CGG CCA GCC TCG CTG CAG CGG GTG GCG AGC CTG GAG CAT CTC CAG AAG AGG
TAA CCG GCC GGT CGG AGC GAC GTC GCC CAC CGC TCG GAC CTC GTA GAG GTC TTC TCC
 I   G   R   P   A   S   L   Q   R   V   A   S   L   E   H   L   Q   K   R>
___f___f___f___f___f___f___f___f__EXON6____f___f___f___f___f___f___f___f___>

 5030       5040       5050       5060       5070       5080
ATG TGC GGT GGG CCG GCT TCG TCT GGG TCG ACG TCC TGA GACCGA AACCCAGAGC
TAC ACG CCA CCC GGC CGA AGC AGA CCC AGC TGC AGG ACT CTGGCT TTGGGTCTCG
 M   C   G   G   P   A   S   S   G   S   T   S   *>
___f___f___f___f___f__EXON6____f___f___f___f___f___>

      5090       5100       5110       5120       5130       5140       5150
TGCTTCGGTT CTGAAAGACA CTGCGAGCAG GAAATGATGA TTGGACAGGC GTAGACATTG CTAATGCTGT
ACGAAGCCAA GACTTTCTGT GACGCTCGTC CTTTACTACT AACCTGTCCG CATCTGTAAC GATTACGACA

      5160       5170       5180       5190       5200       5210       5220
GAGGTTGATG ATTGTTGGTC GTCGTCGTCG TCATTGTGCA TTCTTTGTAA GGGACACCTC TTAGTACCCT
CTCCAACTAC TAACAACCAG CAGCAGCAGC AGTAACACGT AAGAAACATT CCCTGTGGAG AATCATGGGA

      5230       5240       5250       5260       5270       5280       5290
CTTCTTCTAA GGGACTTAGT ACCCCTTGTG GATCTCATCG TCCTAAATAC TATACACATT AGCCAAATGT
GAAGAAGATT CCCTGAATCA TGGGGAACAC CTAGAGTAGC AGGATTTATG ATATGTGTAA TCGGTTTACA

>terminator
                                                                          |
      5300       5310       5320       5330       5340       5350       5360
TCATTGGTGT GATGGCGTCG TCCCTAATTT GAACGACTGA TTTCAGGCAG CTGCTATGCT ATCATTCAAT
AGTAACCACA CTACCGCAGC AGGGATTAAA CTTGCTGACT AAAGTCCGTC GACGATACGA TAGTAAGTTA
```

Fig. 2H

```
      5370       5380       5390       5400       5410       5420       5430
AATATTTTGA TCGATGCTTC CTCTTGTCTT TTGCTCTTAA GCAACCAAGC ATAAAGATAT CACTACCTTT
TTATAAAACT AGCTACGAAG GAGAACAGAA AACGAGAATT CGTTGGTTCG TATTTCTATA GTGATGGAAA

      5440       5450       5460       5470       5480       5490       5500
TGAGCTGTTC ATTTGAAGTG CAAAGCTAAG CTCAATATCT CAGGTGTTCA TTTGAAGTTT AAAGGTGAAC
ACTCGACAAG TAAACTTCAC GTTTCGATTC GAGTTATAGA GTCCACAAGT AAACTTCAAA TTTCCACTTG

      5510       5520       5530       5540       5550       5560       5570
TGATAACAAA CGTCAGGCTA TGGTGAATGA AGGGACGTGT ACATCCCTAA TACATGTCAT TTTCATAATC
ACTATTGTTT GCAGTCCGAT ACCACTTACT TCCCTGCACA TGTAGGGATT ATGTACAGTA AAAGTATTAG

      5580       5590       5600       5610       5620       5630       5640
AAATTAGTTG ATGCATTTTC ACCCAGAATC CCATCACAGT TCATCATACA AGCAAGTGTA GTTATTAATG
TTTAATCAAC TACGTAAAAG TGGGTCTTAG GGTAGTGTCA AGTAGTATGT TCGTTCACAT CAATAATTAC

      5650       5660       5670       5680       5690       5700       5710
GTAAATTTTT CGTTTAGAGA AAAAAAAAGG AAGCCTTATA TAAGATTCAC CGGTGGGGTG TGAACAATAA
CATTTAAAAA GCAAATCTCT TTTTTTTTCC TTCGGAATAT ATTCTAAGTG GCCACCCCAC ACTTGTTATT

      5720       5730       5740       5750       5760       5770       5780
TCAATGAATG AGATCGCATC CCGTAAGGGC AGCCTAGCTA GACAAAAATG CATAAAACTC CGTATACCAA
AGTTACTTAC TCTAGCGTAG GGCATTCCCG TCGGATCGAT CTGTTTTTAC GTATTTTGAG GCATATGGTT

      5790       5800       5810       5820       5830       5840       5850
CCACAACAAC GCTTGCGCAC GCGCTCAAAT GGCAGCGACT TCATCGCTTT CGCGGGCAAG AAACGAATCA
GGTGTTGTTG CGAACGCGTG CGCGAGTTTA CCGTCGCTGA AGTAGCGAAA GCGCCCGTTC TTTGCTTAGT

      5860       5870       5880       5890       5900       5910       5920
AGTGATACAT TGGCAGGGAA CCACCAAAAG AAGGCCATCC AATCCAATCC ACTCCAACGC GGCATGGAAG
TCACTATGTA ACCGTCCCTT GGTGGTTTTC TTCCGGTAGG TTAGGTTAGG TGAGGTTGCG CCGTACCTTC

      5930       5940       5950       5960       5970       5980       5990
ACAAGACAGA TGATTCACAG CTATCTTCTG CTTCTACAAG TTTGATACTT TGTACTGTCC TTTCAGGGAA
TGTTCTGTCT ACTAAGTGTC GATAGAAGAC GAAGATGTTC AAACTATGAA ACATGACAGG AAAGTCCCTT

      6000       6010       6020       6030       6040       6050       6060
AAAAGAGCAT CAGATTAGTC TGATCTCGGG CGCGTTGAGT TCTTGTGGGA GATCTTGTTG TGGAGTGGCA
TTTTCTCGTA GTCTAATCAG ACTAGAGCCC GCGCAACTCA AGAACACCCT CTAGAACAAC ACCTCACCGT

      6070       6080       6090       6100       6110       6120       6130
GGAGTGACGA TCGGCTGCCC CGTTTTCTTC TACCGAAACA TCGCCAGTAA AGAAGCCAAA AAGACAATAA
CCTCACTGCT AGCCGACGGG GCAAAAGAAG ATGGCTTTGT AGCGGTCATT TCTTCGGTTT TTCTGTTATT

      6140       6150       6160       6170       6180       6190       6200
TACGGCAATG GGGATCGCCC ATCTGCATAA AACATTGCAT GACGGAACTG ATTAATACAA GAATGACATG
ATGCCGTTAC CCCTAGCGGG TAGACGTATT TTGTAACGTA CTGCCTTGAC TAATTATGTT CTTACTGTAC

      6210       6220
TAAGCTGATA ATTACGCGTG CAAGCTT
ATTCGACTAT TAATGCGCAC GTTCGAA
```

Fig. 2I

```
        10         20         30         40         50         60         70         80         90
AAGCTTGCAT GCCTGCAGGG AGGAGAGGGG AGAGATGGTG AGAGAGGAGG AAGAAGAGGA GGGGTGACAA TGATATGTGG GCCATGTGGC
                                                                    >Reb_site1
                                                                                     |
       100        110        120        130        140        150        160        170        180
CCCCACCATT TTTTAATTCA TTCTTTTGTT GAAACTGACA TGTGGGTCCC ATGAGAATTA TTATTTTTCG GATCGAATT GCCACGTAAGC

                                       >Reb_site1  >reb_site2
                                                |          |
       190        200        210        220        230        240        250        260        270
GCTACGTCAA TGCTACGTCA GATGAAGACC GAGTCAAATT AGCCACGTAAG CGCCACGTCAG CCAAAACC ACCATCCAAA CCGCCGAGGG

       280        290        300        310        320        330        340        350        360
ACCTCATCTG CACTGGTTTT GATAGTTGAG GGACCCGTTG TATCTGGTTT TTCGATTGAA GGACGAAAAT CAAATTTGTT GACAAGTTAA

       370        380        390        400        410        420        430        440        450
GGGACCTTAA ATGAACTTAT TCCATTTCAA AATATTCTGT GAGCCATATA TCCGTGGGCT TCCAATCCTC CTCAAATTAA AGGGCCTTTT

       460        470        480        490        500        510        520        530        540
TAAAATAGAT AATTGCCTTC TTTCAGTCAC CCATAAAAGT ACAAAACTAC TACCAACAAG CAACATGCGC AGTTACACAC ATTTTCTGCA

       550        560        570        580        590        600        610        620        630
CATTTCCACC ACGTCACAAA GAGCTAAGAG TTATCCCTAG GACAATCTCA TTAGTGTAGA TACATCCATT AATCTTTTAT CAGAGGCAAA

       640        650        660        670        680        690        700        710        720
CGTAAAGCCG CTCTTTATGA CAAAAATAGG TGACACAAAA GTGTTATCTG CCACATACAT AACTTCAGAA ATTACCCAAC ACCAAGAGAA

       730        740        750        760        770        780        790        800        810
AAATAAAAAA AAATCTTTTT GCAAGCTCCA AATCTTGGAA ACCTTTTTCA CTCTTTGCAG CATTGTACTC TTGCTCTTTT TCCAACCGAT

       820        830        840        850        860        870        880        890        900
CCATGTCACC CTCAAGCTTC TACTTGATCT ACACGAAGCT CACCGTGCAC ACAACCATGG CCACAAAAAC CCTATAAAAC CCCATCCGAT

       910        920        930        940        950        960        970        980        990
CGCCATCATC TCATCATCAG TTCATCACCA ACAAACAAAA GAGGAAAAAA AACATATACA CTTCTAGTGA TTGTCTGATT GATCATCAAT

      1000       1010       1020       1030       1040       1050       1060
CTAGAGGATC CCCGGGTGGT CAGTCCCTT ATG
                             Gus Start site
```

Fig. 4

```
       10        20        30        40        50        60        70        80        90       100
CTGCAGGGAGGAGAGGGGAGAGATGGTGAGAGAGGAGGAAGAAGAGGAGGGGTGACAATGATATGTGGGCCATGTGGCCCCCACCATTTTTAATTCATT

                                                  ACGT core     ACGT core     ACGT core
      110       120       130       140       150       160       170       180       190       200
CTTTTGTTGAAACTGACATGTGGGTCCCATGAGAATTATTATTTTTCGGATCGAATTGCCACGTAAGCGCTACGTCAATGCTACGTCAGATGAAGACCGA

     ACGT core     ACGT core
      210       220       230       240       250       260       270       280       290       300
GTCAAATTAGCCACGTAAGCGCCACGTCAGCCAAAACCACCATCCAAACCGCCGAGGGACCTCATCTGCACTGGTTTTGATAGTTGAGGGACCCGTTGTA

      310       320       330       340       350       360       370       380       390       400
TCTGGTTTTTCGATTGAAGGACGAAAATCAAATTTGTTGACAAGTTAAGGGACCTTAAATGAACTTATTCCATTTCAAAATATTCTGTGAGCCATATATC

      410       420       430       440       450       460       470       480       490       500
CGTGGGCTTCCAATCCTCCTCAAATTAAAGGGCCTTTTTAAAATAGATAATTGCCTTCTTTCAGTCACCCATAAAAGTACAAAACTACTACCAACAAGCA

                                       ACGT core
      510       520       530       540       550       560       570       580       590       600
ACATGCGCAGTTACACACATTTTCTGCACATTTCCACCACGTCACAAAGAGCTAAGAGTTATCCCTAGGACAATCTCATTAGTGTAGATACATCCATTAA

             ACGT core
               prolaminbox
      610       620       630       640       650       660       670       680       690       700
TCTTTTATCAGAGGCAAACGTAAAGCCGCTCTTTATGACAAAAATAGGTGACACAAAAGTGTTATCTGCCACATACATAACTTCAGAAATTACCCAACAC

                                                            prolaminbox
      710       720       730       740       750       760       770       780       790       800
CAAGAGAAAAATAAAAAAAAATCTTTTTGCAAGCTCCAAATCTTGGAAACCTTTTTCACTCTTTGCAGCATTGTACTCTTGCTCTTTTTCCAACCGATCC

                                                                TATA_box
      810       820       830       840       850       860       870       880       890       900
ATGTCACCCTCAAGCTTCTACTTGATCTACACGAAGCTCACCGTGCACACAACCATGGCCACAAAAACCCTATAAAACCCCATCCGATCGCCATCATCTC

txn_start_site
      910       920       930       940       950       960       970       980
ATCATCAGTTCATCACCAACAAACAAAAGAGGAAAAAAAACATATACACTTCTAGTGATTGTCTGATTGATCATCAATCTAGA
```

Fig. 9 prolaminbox (30)

10 20 30 40 50 60 70 80 90 100
CTGCAGGCCAGGGAAAGACAATGGACATGCAAAGAGGTAGGGGCAGGGAAGAAACACTTGGAGATCATAGAAGAACATAAGAGGTTAAACATAGGAGGGC prolaminbox (168)

110 120 130 140 150 160 170 180 190 200
ATAATGGACAATTAAATCTACATTAATTGAACTCATTTGGGAAGTAAACAAAATCCATATTCTGGTGTAAATCAAACTATTTGACGCGGATTTACTAAGA 210 220 230 240 250 260 270 280 290 300
TCCTATGTTAATTTTAGACATGACTGGCCAAAGGTTTCAGTTAGTTCATTTGTCACGGAAAGGTGTTTTCATAAGTCCAAAACTCTACCAACTTTTTTGC

ACGT core (301) GCN_motif (326) GCN_motif (347)

310 320 330 340 350 360 370 380 390 400
ACGTCATAGCATAGATAGATGTTGTGAGTCATTGGATAGATATTGTGAGTCAGCATGGATTTGTGTTGCCTGGAAATCCAACTAAATGACAAGCAACAAA prolaminbox (441)

410 420 430 440 450 460 470 480 490 500
ACCTGAAATGGGCTTTAGGAGAGATGGTTTATCAATTTACATGTTCCATGCAGGCTACCTTCCACTACTCGACATGGTTAGAAGTTTTGAGTGCCGCATA 510 520 530 540 550 560 570 580 590 600
TTTGCGGAAGCAATGGCACTACTCGACATGGTTAGAAGTTTTGAGTGCCGCATATTTGCGGAAGCAATGGCTAACAGATACATATTCTGCCAAACCCCAA

ACGT core (697)

610 620 630 640 650 660 670 680 690 700
GAAGGATAATCACTCCTCTTAGATAAAAAGAACAGACCAATGTACAAACATCCACACTTCTGCAAACAATACACCAGAACTAGGATTAAGCCCATTACGT 710 720 730 740 750 760 770 780 790 800
GGCTTTAGCAGACCGTCCAAAAATCTGTTTTGCAAGCACCAATTGCTCCTTACTTATCCAGCTTCTTTTGTGTTGGCAAACTGCCCTTTTCCAACCGATT

TATA-box (883)

810 820 830 840 850 860 870 880 890 900
TTGTTTCTTCTCACGCTTTCTTCATAGGCTAAACTAACCTCGGCGTGCACACAACCATGTCCTGAACCTTCACCTCGTCCCTATAAAAGCCCATCCAACC txn_start_site (915)

910 920 930 940 950 960 970
TTCACAATCTCATCATCACCCACAACACCGAGCACCCCAATCTACAGATCAATTCACTGACAGTTCACTGATCTAGA

Fig. 10

SEQUENCE LISTING

<160> NUMBER OF SEQ ID NOS: 40

<210> SEQ ID NO 1
<211> LENGTH: 24

-continued

<212> TYPE: DNA
<213> ORGANISM: Artificial Sequence
<220> FEATURE:
<223> OTHER INFORMATION: primer

<400> SEQUENCE: 1
ctgatatgtg cccatgttcc aaac 24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ccttgctgaa tgcagatgtt tcac 24

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
gttagtctgc agtgtaagtg tagcttc 27

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
atggttgtct agattttgtg ggactgaac 29

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
acagacagct gcagagatat ggattttcta ag 32

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
ggaactctct agagctattt gtacttgctt atg 33

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7

-continued tccgagctgc agtaatggat acctagt 27

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
gtagtttcta gagctattag cagttgc 27

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
cggtgctgca gatgggttgg gaaccct 27

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
atgatctaga ttgctctggg acatagat 28

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
aattcctgca gcatcggctt aggtgta 27

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
tgatctagat tgttgttgga ttctact 27

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
ggcgcctgca gggaggagag gggagagat 29

<210> SEQ ID NO 14
<211> LENGTH: 29
<212> TYPE: DNA
<213> ORGANISM: Artificial Sequence -continued
<220> FEATURE:
<223> OTHER INFORMATION: primer

<400> SEQUENCE: 14
accttgctct agattgatga tcaatcaga 29

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
cgtcgtctct gcaggccagg gaaagacaat g 31

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
cgcttatcta gatcagtgaa ctgtcagtg 29

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
ttctgggatc caagatgcct accgagg 27

<210> SEQ ID NO 18
<211> LENGTH: 27
<212> TYPE: DNA
<213> ORGANISM: Artificial Sequence
<220> FEATURE:
<223> OTHER INFORMATION: primer

<400> SEQUENCE: 18
ggggtcggat ccgagatggg catggac 27

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
agtggggatc ctaagccgag gccgcaac 28

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
gctaggggat cctggtgcat aggtagca 28

-continued

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
cggcaacagg attcaatct 19

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ccatccaatc caatccactc caac 24

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
aggcgattaa gttgggtaac g 21

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
cctagccaaa gtcttcgagc ggtg 24

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
gcgatgttgt cttgcagc 18

<210> SEQ ID NO 26
<211> LENGTH: 779
<212> TYPE: DNA
<213> ORGANISM: Oryza sativa

<400> SEQUENCE: 26
ttctgtagta cagacaaaac taaaagtaat gaaagaagat gtggtgttag aaaaggaaac 60
aatatcatga gtaatgtgtg agcattatgg gaccacgaaa taaaaagaac attttgatga 120
gtcgtgtatc ctcgatgagc ctcaaaagtt ctctcacccc ggataagaaa cccttaagca 180
atgtgcaaag tttgcattct ccactgacat aatgcaaaat aagatatcat cgatgacata 240
gcaactcatg catcatatca tgcctctctc aacctattca ttcctactca tctacataag 300
tatcttcagc taaatgttag aacataaacc cataagtcac gtttgatgag tattaggcgt 360

-continued

```
gacacatgac aaatcacaga ctcaagcaag ataaagcaaa atgatgtgta cataaaactc    420

cagagctata tgtcatattg caaaaagagg agagcttata agacaaggca tgactcacaa    480

aaattcactt gcctttcgtg tcaaaaagag gagggcttta cattatccat gtcatattgc    540

aaaagaaaga gagaaagaac aacacaatgc tgcgtcaatt atacatatct gtatgtccat    600

cattattcat ccacctttcg tgtaccacac ttcatatatc ataagagtca cttcacgtct    660

ggacattaac aaactctatc ttaacattta gatgcaagag cctttatctc actataaatg    720

cacgatgatt tctcattgtt tctcacaaaa agcattcagt tcattagtcc tacaacaac     779
```

<210> SEQ ID NO 27
<211> LENGTH: 672
<212> TYPE: DNA
<213> ORGANISM: Oryza sativa

<400> SEQUENCE: 27

```
aattccttct acatcggctt aggtgtagca acacgacttt attattatta ttattattat     60

tattattatt ttacaaaaat ataaaataga tcagtccctc accacaagta gagcaagttg    120

gtgagttatt gtaaagttct acaaagctaa tttaaaagtt attgcattaa cttatttcat    180

attacaaaca agagtgtcaa tggaacaatg aaaaccatat gacatactat aattttgttt    240

ttattattga aattatataa ttcaaagaga ataaatccac atagccgtaa agttctacat    300

gtggtgcatt accaaaatat atatagctta caaaacatga caagcttagt ttgaaaaatt    360

gcaatcctta tcacattgac acataaagtg agtgatgagt cataatatta tttttcttgc    420

tacccatcat gtatatatga tagccacaaa gttactttga tgatgatatc aaagaacatt    480

tttaggtgca cctaacagaa tatccaaata atatgactca cttagatcat aatagagcat    540

caagtaaaac taacactcta aagcaaccga tgggaaagca tctataaata gacaagcaca    600

atgaaaatcc tcatcatcct tcaccacaat tcaaatatta tagttgaagc atagtagtag    660

aatccaacaa ca                                                        672
```

<210> SEQ ID NO 28
<211> LENGTH: 879
<212> TYPE: DNA
<213> ORGANISM: Oryza sativa

<400> SEQUENCE: 28

```
aagcttgcgc gcggaatacg gtggtggaga tgggttggga accctggatt ccaaacacag     60

cccaagtcta tccaaaatgt ttagacaaga aaatacgtaa caagttggtt tacagaaata    120

gcaattagat caatcctgca ctacaagtag agtaaagtgg tgatttctct taaatctctc    180

gaatggtgat ttaagaattc agtgcaaacc aaatccttgc tataatcaaa tgttcggtac    240

cccatcaacg gaacaataaa aagcgcctgg ctaccataat tttgtcattc ttcttcaatt    300

tgtaatttaa gatgcatgag gccacacgac cttaatgttc aacgtgtcat gcattagtga    360

aataatagct cacaaaacgc aacaaatata gctagataac ggttgcaatc cttaccaaac    420

taacgtataa agtgagcgat tagtcatatc attatctccc gcctgctaac catcgtgtac    480

accatccgat ccaaaaatga caacttctag ggatgaacct ggacaaggtt tagggtttag    540

ggatgaatct ggacaatgat tgttcaggtt catccctaga tgttgctttc tccttacggg    600

acggagggag tatatgtgat ggacacaaaa gttactttca tgatgaaagg aaaggggatt    660

tgttggggca ctaatagaac atctgtccaa atggcatgac tcacttatat cctaatagga    720
```

-continued

```
catccaagaa aaactaacac tctaaagcaa ccgatgagga attgaaagaa aatacgtgcc    780

accgcatcta taaatggaca agcgcaatgg aaaccctcct catcgttcac acagttcaag    840

cattatacag caaaatagaa agatctatgt cccagagca                           879
```

<210> SEQ ID NO 29
<211> LENGTH: 883
<212> TYPE: DNA
<213> ORGANISM: Oryza sativa

<400> SEQUENCE: 29

```
ctgcagggag gagaggggag agatggtgag agaggaggaa gaagaggagg ggtgacaatg     60

atatgtgggc catgtggccc ccaccatttt ttaattcatt cttttgttga aactgacatg    120

tgggtcccat gagaattatt atttttcgga tcgaattgcc acgtaagcgc tacgtcaatg    180

ctacgtcaga tgaagaccga gtcaaattag ccacgtaagc gccacgtcag ccaaaaccac    240

catccaaacc gccgagggac ctcatctgca ctggttttga tagttgaggg acccgttgta    300

cgtgggcttc caatcctcct caaattaaag ggccttttta aaatagataa ttgccttctt    360

tcagtcaccc ataaaagtac aaaactacta ccaacaagca acatgcgcag ttacacacat    420

tttctgcaca tttccaccac gtcacaaaga gctaagagtt atccctagga caatctcatt    480

agtgtagata catccattaa tcttttatca gaggcaaacg taaagccgct ctttatgaca    540

aaaataggtg acacaaaagt gttatctgcc acatacataa cttcagaaat tacccaacac    600

caagagaaaa ataaaaaaaa atctttttgc aagctccaaa tcttggaaac ctttttcact    660

ctttgcagca ttgtactctt gctcttttc caaccgatcc atgtcaccct caagcttcta    720

cttgatctac acgaagctca ccgtgcacac aaccatggcc acaaaaaccc tataaaaccc    780

catccgatcg ccatcatctc atcatcagtt catcaccaac aaacaaaaga ggaaaaaaaa    840

catatacact tctagtgatt gtctgattga tcatcaatct aga                      883
```

<210> SEQ ID NO 30
<211> LENGTH: 877
<212> TYPE: DNA
<213> ORGANISM: Tricticum aestivum

<400> SEQUENCE: 30

```
ctgcaggcca gggaaagaca atggacatgc aaagaggtag gggcagggaa gaaacacttg     60

gagatcatag aagaacataa gaggttaaac ataggagggc ataatggaca attaaatcta    120

cattaattga actcatttgg gaagtaaaca aaatccatat tctggtgtaa atcaaactat    180

ttgacgcgga tttactaaga acgtcatagc atagatagat gttgtgagtc attggataga    240

tattgtgagt cagcatggat ttgtgttgcc tggaaatcca actaaatgac aagcaacaaa    300

acctgaaatg ggctttagga gagatggttt atcaatttac atgttccatg caggctacct    360

tccactactc gacatggtta gaagttttga gtgccgcata tttgcggaag caatggcact    420

actcgacatg gttagaagtt ttgagtgccg catatttgcg gaagcaatgg ctaacagata    480

catattctgc caaaccccaa gaaggataat cactcctctt agataaaaag aacagaccaa    540

tgtacaaaca tccacacttc tgcaaacaat acaccagaac taggattaag cccattacgt    600

ggctttagca gaccgtccaa aaatctgttt tgcaagcacc aattgctcct tacttatcca    660

gcttcttttg tgttggcaaa ctgccctttt ccaaccgatt ttgtttcttc tcacgctttc    720

ttcataggct aaactaacct cggcgtgcac acaaccatgt cctgaacctt cacctcgtcc    780

ctataaaagc ccatccaacc ttcacaatct catcatcacc cacaacaccg agcaccccaa    840
```

-continued

```
tctacagatc aattcactga cagttcactg atctaga                          877


<210> SEQ ID NO 31
<211> LENGTH: 1362
<212> TYPE: DNA
<213> ORGANISM: Zea mays

<400> SEQUENCE: 31

atggagcacg tcatctcaat ggaggagatc ctcgggccct tctgggagct gctaccaccg     60

ccagcgccag agccagagcg agagcagcct ccggtaaccg gcatcgtcgt cggcagtgtc    120

atagacgttg ctgctgctgg tcatggtgac ggggacatga tggatcagca gcacgccaca    180

gagtggacct ttgagaggtt actagaagag gaggctctga cgacaagcac accgccgccg    240

gtggtggtgg tgccgaactc ttgttgctca ggcgccctaa atgctgaccg gccgccggtg    300

atggaagagg cggtaactat ggcgcctgcg gcggtgagta gtgccgtagt aggtgacccc    360

atggagtaca atgccatact gaggaggaag ctggaggagg acctcgaggc cttcaaaatg    420

tggagggcgg actccagtgt tgtgacctca gatcaacgtt ctcaaggctc aaacaatcac    480

actggaggta gcagcatcag gaataatcca gtgcagaaca agctgatgaa cggcgaagat    540

ccaatcaaca ataaccacgc tcaaactgca ggccttggcg tgaggcttgc tactagctct    600

tcctcgagag atccttcacc atcagacgaa gacatggacg gagaagtaga gattctgggg    660

ttcaagatgc ctaccgagga aagagtgagg aaaaaggaat ccaatagaga atcagccaga    720

cgctcgagat acaggaaagc cgctcacctg aaagaactgg aagaccaggt agcacagcta    780

aaagccgaga attcttgcct gctgaggcgc attgccgctc tgaaccagaa gtacaacgac    840

gctaacgtcg acaacagggt gctgagagcg gacatggaga ccctaagagc taaggtgaag    900

atgggagagg actctctgaa gcgggtgata gagatgagct catcagtgcc gtcgtccatg    960

cccatctcgg cgccgacccc cagctccgac gctccagtgc cgccgccgcc tatccgagac   1020

agcatcgtcg gctacttctc cgccacagcc gcagacgacg atgcttcggt cggcaacggt   1080

ttcttgcgac tgcaagctca tcaagagcct gcatccatgg tcgtcggtgg aactctgagc   1140

gccacagaga tgaaccgagt agcagcagcc acgcattgcg cgggggccat ggagctcatc   1200

cagacggcga tgggatccat gccgccgacc tccgcctccg gatctacacc gccgccgcag   1260

attatgagct gctgggtcca aatggggcca tacacatgga catgtattag gcactgcggg   1320

tttcgtgatc gctgggaaca ttttatttgc aggcgtcgct ga                      1362


<210> SEQ ID NO 32
<211> LENGTH: 1314
<212> TYPE: DNA
<213> ORGANISM: Zea mays

<400> SEQUENCE: 32

atggagcacg tcatctcaat ggaggagatc ctcgggccct tctgggagct gctaccaccg     60

ccagcgccag agccagagcg agagcagcct ccggtaaccg gcatcgtcgt cggcagtgtc    120

atagacgttg ctgctgctgg tcatggtgac ggggacatga tggatcagca gcacgccaca    180

gagtggacct ttgagaggtt actagaagag gaggctctga cgacaagcac accgccgccg    240

gtggtggtgg tgccgaactc ttgttgctca ggcgccctaa atgctgaccg gccgccggtg    300

atggaagagg cggtaactat ggcgcctgcg gcggtgagta gtgccgtagt aggtgacccc    360

atggagtaca atgccatact gaggaggaag ctggaggagg acctcgaggc cttcaaaatg    420
```

-continued tggagggcgg cctccagtgt tgtgacctca gatcaacgtt ctcaaggctc aaacaatcac 480
actggaggta gcagcatcag gaataatcca gtgcagaaca agctgatgaa cggcgaagat 540
ccaatcaaca ataaccacgc tcaaactgca ggccttggcg tgaggcttgc tactagctct 600
tcctcgagag atccttcacc atcagacgaa gacatggacg gagaagtaga gattctgggg 660
ttcaagatgc ctaccgagga aagagtgagg aaaagaaagg aatccaatag agaatcagcc 720
agacgctcga gatacaggaa agccgctcac ctgaaagaac tggaagacca ggtagcacag 780
ctaaaagccg agaattcttg cctgctgagg cgcattgccg ctctgaacca gaagtacaac 840
gacgctaacg tcgacaacag ggtgctgaga gcggacatgg agaccctaag agctaaggtg 900
aagatgggag aggactctct gaagcgggtg atagagatga gctcatcagt gccgtcgtcc 960
atgcccatct cggcgccgac ccccagctcc gacgctccag tgccgccgcc gcctatccga 1020
gacagcatcg tcggctactt ctccgccaca gccgcagacg acgatgcttc ggtcggcaac 1080
ggtttcttgc gactgcaagc tcatcaagag cctgcatcca tggtcgtcgg tggaactctg 1140
agcgccacag agatgaaccg agtagcagca gccacgcatt gcgcgggggc catggagcac 1200
atccagacgg cgatgggatc catgccgccg acctccgcct ccggatctac accgccgccg 1260
caggattatg agctgctggg tccaaatggg gccatacaca tggacatgta ttag 1314

<210> SEQ ID NO 33
<211> LENGTH: 466
<212> TYPE: DNA
<213> ORGANISM: Oryza sativa

<400> SEQUENCE: 33
tcctgcaaca atgaagatca ttttcgtctt tgctctcctt gctattgctg catgcagcgc 60
cactgcgcag tttgatgttt taggtcaaaa tattaggcaa tatcaggtgc agtcgcctct 120
cctgctacag caacaggtgc ttagcccata taatgagttc gtaaggcagc agtatagcat 180
tgcggcaagc accttcttgc aatcagctgc gtttcaactg agaaacaacc aagtcttgca 240
acagctcagg ctggtggcgc aacaatctca ctaccaggac attaacgttg tccaggccat 300
agcgcaccag ctacacctcc agcagtttgg caatctctac attgaccgga atctggctca 360
agctcaagca ctgttggctt ttaacttgcc atctacatat ggtatctacc cttggtccta 420
tagtgcaccc gatagcatta ccacccttgg cggtgtcttg tactga 466

<210> SEQ ID NO 34
<211> LENGTH: 997
<212> TYPE: DNA
<213> ORGANISM: Zea mays

<400> SEQUENCE: 34
ggaaagatcc atggacatga tctccggcag cactgcagca acatcaacac cccacaacaa 60
ccaacaggcg gtgatgttgt catcccccat tataaaggag gaagctaggg acccaaagca 120
gacacgagcc atgccccaaa taggtggcag tggggagcgt aagccgaggc cgcaactacc 180
tgaggcgctc aagtgcccac gctgcgactc caacaacacc aagttttgct actacaacaa 240
ttatagcatg tcacaaccac gctacttttg caaggcttgc cgccgctatt ggacacatgg 300
tggtaccctc cgcaatgtcc ccattggtgg tgggtgtcgc aagaacaaac atgcctctag 360
atttgtcttg ggctctcaca cctcatcgtc ctcatctgct acctatgcac cattatcccc 420
tagcaccaac gctagctcta gcaatatgag catcaacaaa catatgatga tggtgcctaa 480
catgacgatg cctaccccaa cgacaatggg cttattccct aatgtgctcc caacacttat 540

-continued

```
gccgacaggt ggaggcgggg gctttgactt cactatggac aaccaacata gatcattgtc    600

cttcacacca atgtctctac ctagccaggg gccagtgcct atgctggctg caggagggag    660

tgaggcaaca ccgtctttcc tagagatgct gagaggaggg atttttcatg gtagtagtag    720

ctataacaca agtctcacga tgagtggtgg caacaatgga atggacaagc cattttcgct    780

gccatcatat ggtgcaatgt gcacaaatgg gttgagtggc tcaaccacta atgatgccag    840

acaactggtg gggcctcagc aggataacaa ggccatcatg aagagcagta ataacaacaa    900

tggtgtatca ttgttgaacc tctactggaa caagcacaac aacaacaaca acaacaacaa    960

caacaacaac aacaacaaca acaacaaggg acaataa                             997
```

<210> SEQ ID NO 35
<211> LENGTH: 6227
<212> TYPE: DNA
<213> ORGANISM: Oryza sativa

<400> SEQUENCE: 35

```
ggtacccatc taatacatta ataacaagag agagaatgga taatgcaatt atttattttt     60

atgggaggct atatttttat cggattttag taaataacgg ggcaattcgg tacttaggta    120

aagctacgta tgactatcgc taccgctacg gtagttgaat tggaattctt cgatagcatc    180

tgttgtgttg ttgcagttag ggtacttgaa tagctccagc cgtgaaaacg aggggttttc    240

gcaggtttta taggattgcc aagttagact agggcaattc atgttcacgg tattgtgtag    300

tatatgaaaa aggagatctc ccaaacaatt tataattttg tataagggag aaatcgaact    360

tgaggtgtct aattcaccaa ccgagctact ccctccgttt catatatgta tatacatata    420

tacgtatata tacgtatata cacatatacg tatatacata tatggtatat acatatatat    480

atatatatat atatatatat atgtgtgtgt gtgtatgtgg ggtggcaatg ctaaaaagtt    540

ttataatatg aacggatgaa gtactatcca ctaagtccct atagttttct ggcactgtgt    600

agtatacgaa tgcacaatta tatccataaa attgatatta tatattcgtc gcgacgaaaa    660

taaagacata atattcggta taccatttat ccacgatata tctaaattcc actgatatat    720

ctaaattcca cttgatccct tttatggata aattctggat aacaattact accagcagta    780

tatcctacta tcagcgcact gcacaccaaa ctaccctcac ccagtagtta caaacgcata    840

ttttgccgtt agttaattat tatccggtaa agaaggtaaa gaagattggt agtaatccaa    900

aattttccca accccaacct cggaacaaaa accgcgtagt atttgtcgta accaggagca    960

tccgagtcat taatttacac ccaaacacaa aaaattagca gcacgcagcc gccttcccaa   1020

tcctctcctc tctcctctcc tcttctccaa gcggcaattc gcgcgaggtt ttctccgatc   1080

aaaccctcga atccccccct cgcgaatcca tcggagggta gccccgcgat ccgcgtcggc   1140

gagagcggat tccgattccg cgatggagcg ggtgttctcc gtggaggaga tctccgaccc   1200

attctgggtc ccgcctccgc cgccgcagtc ggcggcggcg gcccagcagc agggcggcgg   1260

cggcgtggct tcgggaggtg gtggtggtgt agcgggggc ggcggcggcg ggaacgcgat    1320

gaaccggtgc ccgtcggagt ggtacttcca gaagtttctg gaggaggcgg tgctcgatag   1380

ccccgtcccg aaccctagcc cgagggccga agcgggaggg atcaggggcg caggaggggt   1440

ggtgccggtc gatgttaagc agccgcagct ctcggcggcg gcgacgacga gcgcggtggt   1500

ggaccccgtg gagtacaacg cgatgctgaa gcagaagctg gagaaggacc tcgccgcggt   1560

cgccatgtgg agggtacagc cattctcccc ccctctagta ctcgagagct tactgagatc   1620
```

-continued

```
ggcaatgcta gctactgttt gcatcgaatg tttataggta tttagatcgg gcatttctat   1680
agaccaatgg cgtccatggt cttgcaatgc gctctgttga gtgtcggtgg ttggttcgac   1740
tcatagtatg tagggttgtg cgtatgtaca aacggaagct tcatagacct cggtattgag   1800
attgcgatat cgatgcaacc tgcgaattgg cgatgtaatc agtcatattc ttactaaact   1860
gcgagacagt ggtttgtttg caattgcaat atttttgtat ggggctgctt aaactgtcat   1920
tgccttttta gattggcaat atgtgacttt atgcaagtat ttgattgggc ggatccagga   1980
acaaaaagtt ggggggattc aacataccga gtacactggc ataaacacat catctcagta   2040
ttaaactatg ctaaaatgct attaagagac ctttagcacc tcttatctta tcaaccatgg   2100
tgaaaaaatt gaagggggga ctcagggggg tatccatggg tccgatgggt gcagggggga   2160
ctgagtcccc cctgcaccca cgttgaatcc gccctggcat gcgtataagc tgtcacagcc   2220
atttctaggt gcttgtgctt agttgggtga tgtcagctta atttgtcttt tctatgtcgt   2280
catcgatttt ctaagaaacg aaaaatagcc tatttatgtg ctccagaatt tgatgatccc   2340
tggcccttca tttgctgaaa ttagcctatt tgttggttgc ccttcagttt tttcccagct   2400
tatgttgttg caatgtgtgg ctatgcctcg ttttgtgccc tataatttat tatttgcaat   2460
tcatttttgt acatgactta aaatgacact agagcaacat gcactgattg gttatcctat   2520
aatcatttat gtagttctgt tcattttatc atgctagctc atgtcatttt catcttcagg   2580
cctctggcac agttccacct gagcgtcctg gagctggttc atccttgctg aatgcagatg   2640
tttcacacat aggcgctcct aattccatcg gaggtactta tcttatctgg ttacattttc   2700
agattgttat gaaactaccc aaatatcctg cacaattgca tgggattaaa ttttagtttc   2760
tttgaaatag aagtagagtt gtattgctgt cacgtcatca aatagttctg aagctatgaa   2820
taaataagtt ccgcatttgt tagtgattct ttgaacatta gaattgttat gcttaagtag   2880
atagggttat gtttgtttgg agttccctta aatcatttca ttgctgactg ccagctggca   2940
ggagcatttg ttgttgcctt gaccatgaat gaagaccttc ctgttctgag tgctcacaag   3000
aaaacatatt ttgattaatg caccttgaat ccttaggatc ttgcaaagat gggcacttag   3060
ctttagaatt gagtagtact taaatagctg ttgttatcat gatttgtcct gtagtgaaat   3120
gtcgacaaaa caggaatgct acttttgact tctgatattt catgcctggc tttacttatg   3180
ctctgtttgg aacatgggca catatcaggc aatgctactc cagttcaaaa catgctaagt   3240
ggcccaagtg ggggatcggg ctcacagttg gtacagaatg ttgatgtcct tgtaaagcag   3300
cccaccagct cttcatcaag ggagcagtca gatgatgatg acatgaaggg agaagctgag   3360
accactggaa ctgcaagacc tgctgatcaa agattacaac gaaggtgatc attcattgct   3420
tccttgtaat atagattctg tacataatta acctacctcg tcatgcatgc atgtgtccta   3480
ttttcacctt agccctttca gttggatttc cactttcatc cggtagcctt tcagtttcct   3540
attgcatcgc atatatgatc ttttacctac catattagtt ctctgtgtgc catactcagt   3600
gcttagtgtc tcgagcaaga gaggaatttg tatggctatt acacgtagca ctttgctctc   3660
tacttgttta ttgacataag caatttggga tgaattaaat ctgagttcac atcatattcc   3720
ttatgtcaca agtttctgaa accgattgta tctagtatct ggttgatgca cccccatctt   3780
ggatttgcaa atcaaagtta tactccctag agagctttac ctttcataaa gcaattaccc   3840
caataaacca cggatttgat agctattgac tatgattacc agaattcatt tggcagctat   3900
tttctcaatt taagtttggt attagtctca gttggctgta aaataatgtc acggtagggt   3960
acatgtatgt gcagcataca aggtatgggt gagttatgat atggacagtg tgtacacccc   4020
```

-continued

```
acatttgctc actaaaatca aaatattcaa acgtcacgtg atgatatggt ggattgcatt   4080
ataccttgta ttgtttatta tgttacttgt gctagacaat aatataggct gttcttttgg   4140
gtgattttgt atgaagatgt tgagcaagca cttctcgata taatgctagt tttgttgacc   4200
tgttccagga agcaatccaa tcgggagtca gccaggcgct caagaagcag aaaggcagct   4260
cacttgaatg agctggaggc acaggtgtga tagttcacat agttattttc gataagacat   4320
aaaatcctaa attactggct actgacttca gttatggatt tacttgttac aggtatcgca   4380
attaagagtc gagaactcct cgctgttaag gcgtcttgct gatgttaacc agaagtacaa   4440
tgatgctgct gttgacaata gagtgctaaa agcagatgtt gagaccttga gagcaaaggt   4500
atgctatata tgccttttgc aatatgcatc ccatggattg ctactttggc ttgtttcaaa   4560
ctttcaacgt gacttgtgta ccctgttatt agaagaataa tcccgcctac cattatactc   4620
tataaatcac catttggcca gtccaaacat gattattaaa tcaggtcaat ctgaacattg   4680
aaatgtatca aaaattcgca ggtgaagatg gcagaggact cggtgaagcg ggtgacaggc   4740
atgaacgcgt tgtttcccgc cgcttctgat atgtcatccc tcagcatgcc attcaacagc   4800
tccccatctg aagcaacgtc agacgctgct gttcccatcc aagatgaccc gaacaattac   4860
ttcgctacta acaacgacat cggaggtaac aacaactaca tgcccgacat accttcttcg   4920
gctcaggagg acgaggactt cgtcaatggc gctctggctg ccggcaagat tggccggcca   4980
gcctcgctgc agcgggtggc gagcctggag catctccaga agaggatgtg cggtgggccg   5040
gcttcgtctg ggtcgacgtc ctgagaccga aacccagagc tgcttcggtt ctgaaagaca   5100
ctgcgagcag gaaatgatga ttggacaggc gtagacattg ctaatgctgt gaggttgatg   5160
attgttggtc gtcgtcgtcg tcattgtgca ttctttgtaa gggacacctc ttagtaccct   5220
cttcttctaa gggacttagt accccttgtg gatctcatcg tcctaaatac tatacacatt   5280
agccaaatgt tcattggtgt gatggcgtcg tccctaattt gaacgactga tttcaggcag   5340
ctgctatgct atcattcaat aatattttga tcgatgcttc ctcttgtctt ttgctcttaa   5400
gcaaccaagc ataaagatat cactaccttt tgagctgttc atttgaagtg caaagctaag   5460
ctcaatatct caggtgttca tttgaagttt aaaggtgaac tgataacaaa cgtcaggcta   5520
tggtgaatga agggacgtgt acatccctaa tacatgtcat tttcataatc aaattagttg   5580
atgcattttc acccagaatc ccatcacagt tcatcataca agcaagtgta gttattaatg   5640
gtaaattttt cgtttagaga aaaaaaaagg aagccttata taagattcac cggtggggtg   5700
tgaacaataa tcaatgaatg agatcgcatc ccgtaagggc agcctagcta gacaaaaatg   5760
cataaaactc cgtataccaa ccacaacaac gcttgcgcac gcgctcaaat ggcagcgact   5820
tcatcgcttt cgcgggcaag aaacgaatca agtgatacat tggcagggaa ccaccaaaag   5880
aaggccatcc aatccaatcc actccaacgc ggcatggaag acaagacaga tgattcacag   5940
ctatcttctg cttctacaag tttgatactt tgtactgtcc tttcagggaa aaaagagcat   6000
cagattagtc tgatctcggg cgcgttgagt tcttgtggga gatcttgttg tggagtggca   6060
ggagtgacga tcggctgccc cgttttcttc taccgaaaca tcgccagtaa agaagccaaa   6120
aagacaataa tacggcaatg gggatcgccc atctgcataa aacattgcat gacggaactg   6180
attaatacaa gaatgacatg taagctgata attacgcgtg caagctt                 6227
```

<210> SEQ ID NO 36
<211> LENGTH: 10
<212> TYPE: DNA

-continued

<213> ORGANISM: Oryza sativa
<220> FEATURE:
<221> NAME/KEY: misc_feature
<222> LOCATION: (8)
<223> OTHER INFORMATION: n=a or c

<400> SEQUENCE: 36 gccacgtnag 10

<210> SEQ ID NO 37
<211> LENGTH: 10
<212> TYPE: DNA
<213> ORGANISM: Oryza sativa

<400> SEQUENCE: 37
gccacgtaag 10

<210> SEQ ID NO 38
<211> LENGTH: 10
<212> TYPE: DNA
<213> ORGANISM: Oryza sativa

<400> SEQUENCE: 38
gccacgtcag 10

<210> SEQ ID NO 39
<211> LENGTH: 1022
<212> TYPE: DNA
<213> ORGANISM: Oryza sativa

<400> SEQUENCE: 39
aagcttgcat gcctgcaggg aggagagggg agagatggtg agagaggagg aagaagagga 60
ggggtgacaa tgatatgtgg gccatgtggc ccccaccatt ttttaattca ttcttttgtt 120
gaaactgaca tgtgggtccc atgagaatta ttatttttcg gatcgaattg ccacgtaagc 180
gctacgtcaa tgctacgtca gatgaagacc gagtcaaatt agccacgtaa gcgccacgtc 240
agccaaaacc accatccaaa ccgccgaggg acctcatctg cactggtttt gatagttgag 300
ggacccgttg tatctggttt ttcgattgaa ggacgaaaat caaatttgtt gacaagttaa 360
gggaccttaa atgaacttat tccatttcaa aatattctgt gagccatata tccgtgggct 420
tccaatcctc ctcaaattaa agggcctttt taaaatagat aattgccttc tttcagtcac 480
ccataaaagt acaaaactac taccaacaag caacatgcgc agttacacac attttctgca 540
catttccacc acgtcacaaa gagctaagag ttatccctag gacaatctca ttagtgtaga 600
tacatccatt aatcttttat cagaggcaaa cgtaaagccg ctctttatga caaaaatagg 660
tgacacaaaa gtgttatctg ccacatacat aacttcagaa attacccaac accaagagaa 720
aaataaaaaa aaatcttttt gcaagctcca aatcttggaa accttttca ctctttgcag 780 cattgtactc ttgctctttt tccaaccgat ccatgtcacc ctcaagcttc tacttgatct 840
acacgaagct caccgtgcac acaaccatgg ccacaaaaac cctataaaac cccatccgat 900
cgccatcatc tcatcatcag ttcatcacca acaaacaaaa gaggaaaaaa aacatataca 960
cttctagtga ttgtctgatt gatcatcaat ctagaggatc cccgggtggt cagtccctta 1020
tg 1022

<210> SEQ ID NO 40
<211> LENGTH: 10
<212> TYPE: DNA
<213> ORGANISM: Artificial Sequence -continued

```
<220> FEATURE:
<223> OTHER INFORMATION: Opaque 2 box

<400> SEQUENCE: 40

tccacgtaga                                                              10
```

PLANT TRANSCRIPTION FACTORS AND ENHANCED GENE EXPRESSION

This application is a continuation of U.S. application Ser. No. 09/847,232, filed May 2, 2001, now abandoned, which claims priority to U.S. Provisional Application Ser. Nos. 60/201,182, filed May 2, 2000, now abandoned, and 60/266,920, filed Feb. 6, 2001, now abandoned, all of which are expressly incorporated by reference herein.

REFERENCE TO SEQUENCE LISTING, TABLE OR COMPUTER PROGRAM

A "Sequence Listing" has been submitted with this application in the form of a text file, created 21 May 2008, and named "50665-8018.US02-SEQLISTcorr.TXT" (28,672 bytes), the contents of which are incorporated herein by reference in their entirety.

FIELD OF THE INVENTION

The invention relates to transgenic plants which demonstrate enhanced expression of one or more plant transcription factors, expressed under the control of a seed specific promoter. The invention further relates to methods for producing transgenic plants which exhibit enhanced expression of one or more plant transcription factors and the use of the plants to enhance the expression level of a heterologous protein in the seeds of such transgenic plants.

REFERENCES

Abe, et al., Agric. Biol. Chem. 53, 2969-2973, 1989.
Albani et al., Plant Cell 9: 171-184, 1997.
Alber and Kawasaki, *Mol. and Appl. Genet.* 1:419-434, 1982.
Aukerman et al., *Genes Dev.* 5: 310-320, 1991.
Ausubel, et al., CURRENT PROTOCOLS IN MOLECULAR BIOLOGY, John Wiley & Sons, New York, N.Y., (c) 1987, 1988, 1989, 1990, 1993.
Brandt, et al., *Carlsberg Res. Commun.* 50, 333-345, 1985
Bronstein, et al., *Biotechniques* 17: 172, 1994.
Burr and Burr, *J. Mol. Biol.* 154, 33-49, 1982.
Chen, L., Zhang S., Beachy R. N. & Fauquet C. M., *Plant Cell Reports* 18, 25-31. 1998.
Christensen A. H. and Quail P. H., *Transgenic Research* 5, 213-218, 1996
Conlan R. S., Hammond-Kosack M., and Bevan M., *Plant Journal* 19, 173-181, 1999.
Crossway, *Mol. Gen. Genet,* 202:179-185, 1985.
Dellaporta S. L., Wood J., Kicks J. B., *Plant Mol. Biol. Rep.* 1, 19-20, 1983.
Depicker, et al., *Mol. Appl. Genet.* 1:561-573, 1982.
deWet J R, et al., *Mol. Cell. Biol.* 7: 725-737, 1987.
Entwistle, Carlsberg Res. Commun. 53 (4), 247-258, 1988.
Forde, B. G. et al., *Nucl. Acids Res.* 13:7327-7339, 1985.
Fraley, et al., *Proc Natl Acad Sci USA* 79:1859-1863, 1982.
Fraley, et al., *Proc Natl Acad Sci USA* 80:4803, 1983.
From, et al., *Proc. Nat Acad Sci USA* 82:5824, 1985.
Gelvin, S. B. et al., eds. PLANT MOLECULAR BIOLOGY MANUAL, 1990.
Gielen, et al., *EMBO J.* 3:835-846, 1984
Giroux and Hannah, *Mol Gen Genet.* 243(4):400-8, 1994.
Halford, et al., *Biochim. Biophys. Acta* 950 (3), 435-440, 1988.
Hammond-Kosack et al., EMBO J. 12: 545-554, 1993.
Hartings et al., EMBO J. 8, 2795-2801, 1989.
Holdsworth M. J., Munoz-Blanco J., Hammond-Kosack M., Colot V., Schuch W. and Bevan M. W., *Plant Molecular Biology* 29, 711-720, 1995.
Horsch, et al., *Science* 233:496-498, 1984.
Hwang et al., *Plant Mol. Biol.* 36(3):331-41, 1998.
Kim, S. Y. and Wu, R., *Nucleic Acids Res.* 18 (23), 6845-6852, 1990.
Klein, et al., *Nature* 327:70-73, 1987
Klemsdal, et al., *Mol Gen Genet.* 228(1-2):9-16, 1991.
Knudsen and Müller, *Planta* 185:330-336, 1991).
Kreis, M et al., *J. Mol. Biol.* 183, 499-502, 1985.
Kreis, et al., *Eur. J. Biochem.* 169 (3), 517-525, 1987.
Landschulz et al., *Science* 240, 1759-1764, 1988.
Langridge et al., *Planta* 156,166-170, 1982.
Lavery et al., *Proc Natl Acad Sci USA.* 94(13):6831-6, 1997.
Lee et al., *Biochem. Genet.* 14, 641-650, 1976.
Liang and Pardee, *Methods Mol. Biol.* 85:3-11 1997.
Liu Q., Kasuga M., Sakuma Y., Abe H., Miura S., Yamaguchi-Shinozaki K. and Shinozaki K., *Plant Cell* 10, 1391-1406, 1998.
Maniatis, et al., MOLECULAR CLONING: A LABORATORY MANUAL, 2nd Edition, 1989.
McElroy, D., Zhang, W. G., Cao, J. & Wu, R. *Plant Cell* 2, 163-171, 1990.
Mena M., VicenteCarbajosa J., Schmidt R. J. and Carbonero P., *Plant Journal* 16, 53-62, 1998.
Mertz et al., *Science* 145, 279-280, 1964.
Montana Menal et al., *The Plant Journal* 16(1), 53-62, 1998)
Motto et al., *Mol Gen. Genet.* 212, 488-494, 1988.
Motto et al, *Plant Mol Cell Biol.* 6, 87-114, 1989.
Müller and Knudsen, *Plant J.* 4:343-355, 1993.
Müller et al. *J. Plant Physiol* 145, 606-613, 1995.
Murphy and Dalby, *Cereal Chem.* 48, 336-349, 1971.
Nagel, et al., *FEMS Microbiol. Lett* 67:325, 1990.
Nakase, et al., *Plant Mol. Biol.* 32 (4), 621-630, 1996.
Nakase M et al, *Plant Mol Biol* 33(3):513-22, 1997.
Neuberg et al, *Nature* 338, 589-590, 1989.
Okita, T. W., et al, *J. Biol. Chem.* 264 (21), 12573-12581, 1989.
Onate, L. Vicente-Carbajosa J., Lara P., Diaz I. and Carbonero, P., *Journal of Biological Chemistry* 274, 9175-9182, 1999.
Pedersen et al., *Biochemistry* 19, 1644-1650, 1980.
Sambrook J., F. E. F. and Manitiates T., Molecular Cloning, Cold Spring Harbor Laboratory, Cold Spring Harbor, 1989.
Schell, *Science* 237:1176-1183, 1987
Schmidt et al, *Science* 238, 960-963, 1987.
Schmidt et al, *Proc. Natl. Acad. Sci. USA* 87, 46-50, 1990.
Schmidt R et al, *The Plant Cell,* 4:689-700, 1992.
Schwechheimer C. and Bevan M., *Trends in Plant Science* 3, 378-383, 1998.
Schwechheimer C., Zourelidou M. and Bevan M. W., Annual Review of Plant Physiology and Plant Molecular Biology 49, 127-150, 1998.
Shaw et al., *Plant Physiol* 106(4):1659-65 1994.
Sorensen, et al, *Mol Gen. Genet.* 250 (6), 750-760, 1996.
Takaiwa, F. et al, *FEBS Lett.* 221, 43-47, 1987.
Takaiwa, F. and Oono, K. Jpn. J. *Genet.* 66 (2), 161-171, 1991.
Takaiwa, F et al, *Plant Mol. Biol.* 16 (1), 49-58, 1991a.
Takaiwa, F et al, *Plant Mol. Biol.* 17 (4), 875-885, 1991 b.
Thompson J A, et al, *Plant Sci.* 47: 123-133, 1986.
Turner and Tjian, *Science* 243, 1689-1694, 1989.
Vinson et al., *Science* 246, 911-916, 1989.
Vicente-Carbajosa J, et al., Proc. Natl. Acad. Sci. USA 94: 7685-7690, 1997.

37. Vicente-Carbajosa J, et al., *Plant J.* 13: 629-640, 1998.
Wang, Z. D., et al, *Gene* 223, 321-332, 1998.
Wen T N, et al., *Plant Physiol* 101:1115-1116, 1993.
Wolf N, *Mol. Gen. Genet.* 234 (1), 33-42, 1992.
Xu J., et al, *Proc. Nat. Acad. Sci. U.S.A.* 95, 5661-5666, 1998.
Yang D., et al, *Theoretical and Applied Genetics* 95, 1147-1154, 1997.
Yunes J. A., et al, *Plant Cell* 6, 237-249, 1994.

BACKGROUND OF THE INVENTION

Attempts to control gene activity and/or increase the production of recombinant proteins in plants have been made using high level constitutive promoters, inducible promoters, tissue-specific promoters and developmental stage-specific promoters.

Systems for regulatable expression of genes have been reported in the literature and are generally based on modifying the activity of transcriptional regulatory proteins or by the use exogenous inducers (i.e., compounds) that specifically interact with a particular transcriptional regulatory protein. In either case, the result is to modify promoter activity by affecting the binding of transcriptional regulatory proteins to their DNA binding site and thereby controlling promoter activity for a given gene.

In addition, significant research efforts have been directed to constructing improved expression vectors, modifications of promoters and modifications of 5' and 3' untranslated sequences, with the goal of increasing the expression level of heterologous protein coding sequences. The regulated expression of transgenes in plants such that expression takes place in a manner that does not result in harm to the plant is the focus of extensive research.

Cereal seed storage proteins are a primary source of proteins in the diet of humans and agricultural animals worldwide. The bulk of cereal seed storage proteins are produced solely in the endosperm, a highly specialized tissue devoted to starch and protein biosynthesis and storage. Accordingly, cereal seed storage proteins are an attractive target for the regulated expression of transgenes and a need exists for effective strategies to enhance and regulate gene expression in seed tissues of cereal plants.

SUMMARY OF THE INVENTION

The invention provides transgenic seed crops with improved capacity to produce peptides or polypeptides by the regulated expression of transgenes in the seeds of such crops.

More specifically, the invention provides transgenic monocot plants which comprise the heterologous nucleic acid coding sequence for one or more plant transcription factors operably linked to a seed specific promoter, wherein expression of the transcription factor(s) in a plant cell is effective to activate transcription of a gene operably linked to a seed specific promoter with which the one or more transcription factors interact.

The promoter with which the transcription factor interacts may be derived from the same or a different species from plant in which it is expressed.

The seed specific promoter may be a native or heterologous seed-specific promoter. In some cases, the transcription factor also activates its own promoter.

In one aspect, the transgenic monocot plant comprises the coding sequence for more than one plant transcription factor, each of which is operably linked to a seed specific promoter. The operably linked seed specific promoters may be the same or different.

In a related aspect, the same transcription factor is expressed under the control of two or more different seed-specific promoters, which may result in expression in different seed tissues.

In yet another related aspect, the invention provides transgenic plants that contain the heterologous nucleic acid coding sequence for more than one transcription factor, wherein expression of the transcription factors results in an additive enhancement of expression of a gene operably linked to a seed-specific promoter with which the transcription factors interact.

Preferred transcription factors include opaque 2 (O2), prolamin box factor (PBF), and the rice endosperm bZIP protein (Reb).

Preferred seed-specific promoters include the Gt1, Glb, Bx7, RP6 and PG5a promoters, having the sequence presented as SEQ ID NO:26, SEQ ID NO:29, SEQ ID NO:30, SEQ ID NO:27 and SEQ ID NO:28, respectively.

Preferred plants include rice, corn, barley and wheat.

The invention further provides methods for producing transgenic monocot plants and seeds comprising the heterologous nucleic acid coding sequence for one or more plant transcription factor(s) operably linked to a seed specific promoter. Such transgenic plants may also include the coding sequence for a selected heterologous protein operably linked to a seed-specific promoter that is responsive to the plant transcription factor(s), such that the transgenic plant exhibits enhanced expression of the selected heterologous protein.

The invention also includes a method for producing a transgenic plant that expresses a selected heterologous protein by crossing a transgenic plant that expresses the heterologous nucleic acid coding sequence for one or more plant transcription factors operably linked to a seed specific promoter with a transgenic plant containing a heterologous protein coding sequence under the control of a seed-specific promoter that is responsive to the one or more plant transcription factors.

In yet another aspect, the invention provides a method of making a seed-specific promoter responsive to a transcription factor to which it does not respond in its native state, a modified seed-specific promoter prepared by the method and a transgenic plant comprising such a modified seed-specific promoter.

BRIEF DESCRIPTION OF THE FIGURES

FIGS. 1A-F illustrate cereal seed morphology, wherein: FIG. 1A provides a schematic depiction of cereal seed morphology; FIG. 1B a schematic depiction of the life cycle of the cereal seed; FIG. 1C is an image of GUS (β-glucuronidase) expression in the endosperm of the seed (production in starch); FIG. 1D is an image of GUS expression in the embryo of the seed (production in germ); FIG. 1E is an image of GUS expression in the alleurone of the seed (production in bran); and FIG. 1F is an image of GUS expression during germination (production in malt).

FIGS. 2A-I are a double-stranded depiction of the DNA sequence of the rice (*Oryza sativa*) bZIP protein (SEQ ID NO: 35), designated ("Reb"). The gene sequence of 6.227 kb consists of 5 introns and 6 exons flanked by 1.2 kb of the 5' promoter and 1.2 kb of the 3' region.

FIG. 4 is a single-stranded depiction of a portion of the DNA sequence of the Glb promoter (SEQ ID NO: 39) with putative Reb binding sites indicated.

FIG. 9 depicts the DNA sequence of the rice (*Oryza sativa*) globulin promoter (SEQ ID NO: 29), ("Glb") with putative binding sites for the O2 transcription factor and the prolamin box indicated in the figure.

FIG. 10 depicts the DNA sequence of the wheat Bx7 promoter (SEQ ID NO: 30) with putative binding sites for the O2 transcription factor and the prolamin box indicated in the figure.

FIG. 16A is a diagram that shows the construct API266 (native-Reb), the primer positions and the size of the 522 bp amplified fragment, where one primer was designed based on the vector sequence and the other using the Reb terminator.

FIG. 16B (Reb) is a diagram that shows the construct API264 (Glb-lys), the primer positions and the size of the 278 bp amplified fragment. The primers hybridize to an internal sequence of the human lysozyme gene.

FIG. 16C presents the results of PCR analysis of native-Reb/Glb-Lys co-transformed plants where arrows mark the 522 bp fragment of the Reb/vector region and the 278 bp fragment derived from the internal sequence of the human lysozyme gene.

DETAILED DESCRIPTION OF THE INVENTION

I. Definitions

Figure 1A:
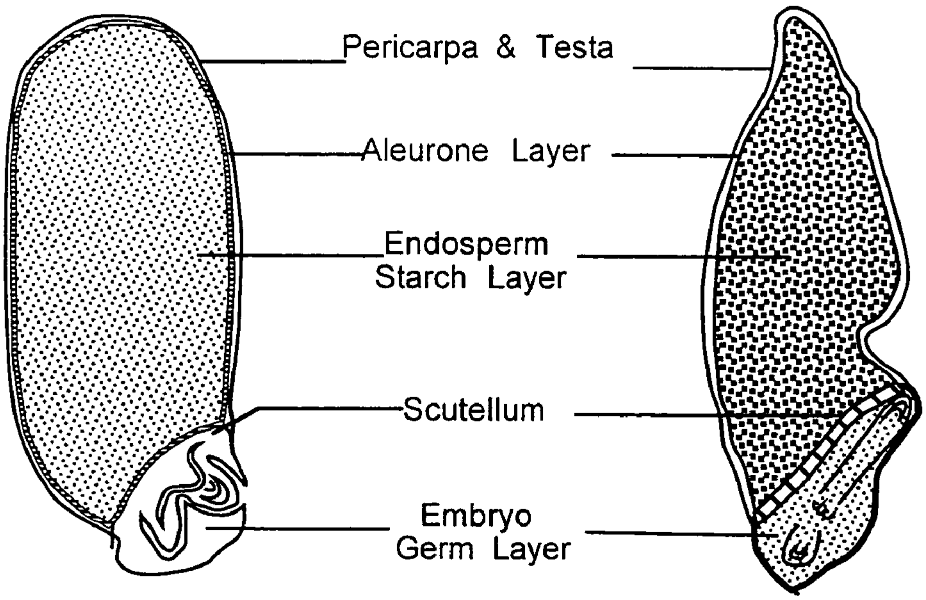

Unless otherwise indicated, all technical and scientific terms used herein have the same meaning as they would to one skilled in the art of the present invention. Practitioners are particularly directed to Sambrook et al., 1989 and Ausubel F M et at, 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

An "isolated polynucleotide" or an "isolated DNA segment" having a sequence which encodes a plant transcription factor is a polynucleotide which contains the coding sequence of the plant transcription factor (i) in isolation, (ii) in combination with additional coding sequences, such as fusion protein or signal peptide, in which the plant transcription factor coding sequence is the dominant coding sequence, (iii) in combination with non-coding sequences, such as control elements, such as promoter and terminator elements, effective for expression of the coding sequence in plant cells, and/or (iv) in a vector or host environment in which the plant transcription factor coding sequence is a heterologous gene.

As used herein, the term "plasmid" refers to a circular double-stranded (ds) DNA construct used as a cloning vector, and which forms an extrachromosomal self-replicating genetic element in many bacteria and some eukaryotes.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "promoter" refers to a nucleic acid sequence that functions to direct transcription of a distal gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid sequence is "heterologous" with respect to a control sequence (i.e. promoter or enhancer) when it does not function in nature to regulate the same gene the expression of which it is currently regulating. Generally, heterologous nucleic acid constructs are introduced into the cell or part of the genome in which they are present, and have been added to the cell, by transfection, microinjection, electroporation, or the like. The sequences may contain a control sequence/DNA coding sequence combination that is the same as, or different from a control sequence/DNA coding sequence combination found in the native plant.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

The term "gene", may be used interchangeably herein with the term "nucleic acid coding sequence", and the term "structural gene" which means a DNA coding region.

As used herein, the term "fragment," when referring to a gene sequence means a polynucleotide having a nucleic acid sequence which is the same as part of, but not all of, the nucleic acid sequence of the full length gene. The fragment preferably includes at least 15 contiguous bases of the gene, preferably at least 20-30 bases. With reference to interaction with a transcription factor, the sequence must be of sufficient length to interact with the transcription factor.

As used herein, the terms "transformed", "stably transformed" or "transgenic" with reference to a plant cell means the plant cell has a non-native (heterologous) nucleic acid sequence integrated into its genome which is maintained through one or more generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "effector", refers to plant transcription factors that "effect" the transcription of genes having the appropriate response sequence.

As used herein, the term "promoter" refers to a sequence of DNA that functions to direct transcription of a gene which is operably linked thereto. A promoter may or may not include additional control sequences (also termed "transcriptional and translational regulatory sequences"), involved in expression of a given gene product. In general, transcriptional and translational regulatory sequences include, but are not limited to, promoter sequences, ribosomal binding sites, transcriptional start and stop sequences, translational start and stop sequences, and enhancer or activator sequences. The promoter may be homologous or heterologous to the cell in which it is found.

As used herein, the terms "regulatable promoter" and "inducible promoter" may be used interchangeably and refer to any promoter the activity of which is affected by a cis or trans acting factor.

As used herein, the terms "transcriptional regulatory protein", "transcriptional regulatory factor" and "transcription factor" may be used interchangeably and refer to a cytoplasmic or nuclear protein that binds a DNA response element and thereby transcriptionally regulates the expression of an associated gene or genes. Transcription factors generally bind directly to a DNA response sequence or element, however in some cases may bind indirectly to another protein, which in turn binds to or is bound to the DNA response element.

As used herein, the terms "response sequence" and "response element" refer to the binding site or sequence for a transcriptional regulatory protein (transcription factor) which may be the part of, overlapping, or adjacent to, a promoter sequence.

As used herein, a "plant cell" refers to any cell derived from a plant, including undifferentiated tissue (e.g., callus) as well as plant seeds, pollen, progagules and embryos.

As used herein, the term "mature plant" refers to a fully differentiated plant.

As used herein, the terms "native" and "wild-type" relative to a given plant trait or phenotype refers to the form in which that trait or phenotype is found in the same variety of plant in nature.

As used herein, the term "plant" includes reference to whole plants, plant organs (for example, leaves, stems, roots, etc.), seeds, and plant cells and their progeny. Plant cell, as used herein includes, without limitation, seeds, suspension cultures, embryos, meristematic regions, callus tissue, leaves roots shoots, gametophytes, sporophytes, pollen, and microspores. The class of plants which can be used in the methods of the present invention is generally as broad as the class of higher plants amenable to transformation techniques, including both monocotyledenous and dicotyledenous plants.

As used herein, the term "transgenic plant" refers to a plant comprising within its genome a heterologous DNA segment. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

II. Methods and Compositions of the Invention

The invention provides transgenic plant cells and transgenic plants which express one or more recombinant transcription factors, wherein expression of the one or more transcription factors is correlated with increased expression of a gene under the control of a promoter with which one or more of the transcription factors interacts.

In activating transcription of a nucleic acid coding sequence, the recombinant transcription factors described herein may interact with (1) a native seed-specific promoter or (2) a non-native, recombinant or heterologous seed-specific promoter. In either case, all or part of the seed-specific promoter sequence is operably linked to a native nucleic acid coding sequence or a heterologous nucleic acid coding sequence (e.g., a transgene) and may be from the same or a different species from that of the plant in which it is present. The transgene may be a reporter gene, such as luciferase or GUS, or a gene encoding a recombinant protein that is expressed in the plant.

Figure 1B:
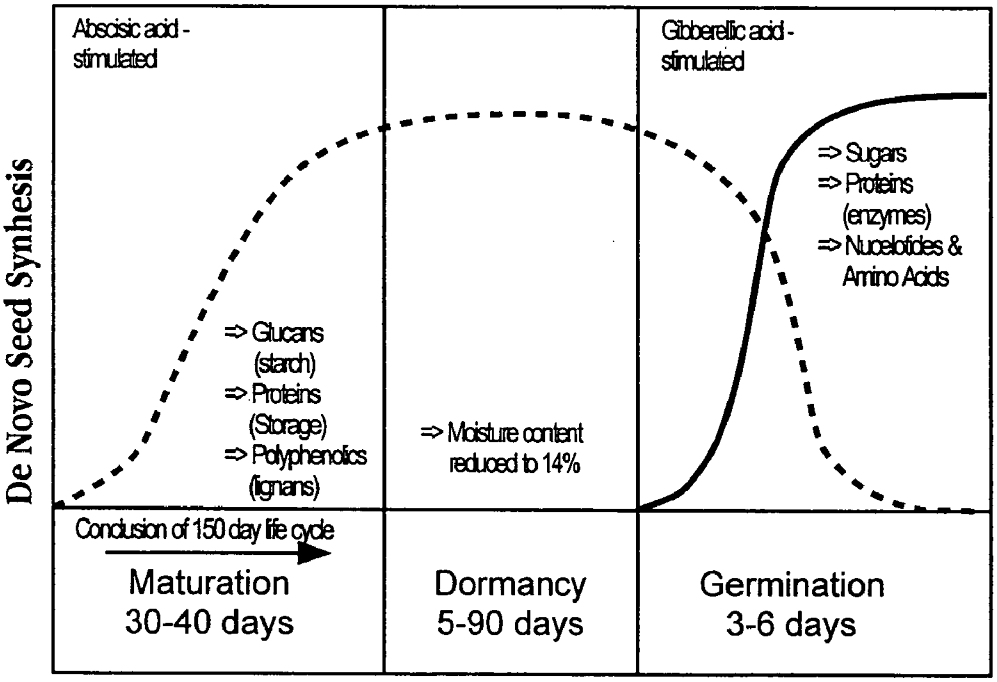
Figure 1C:
Figure 1D:
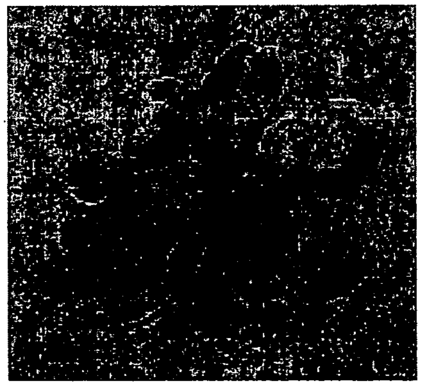
Figure 1E:
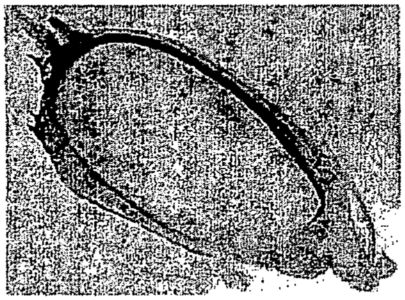
Figure 1F:
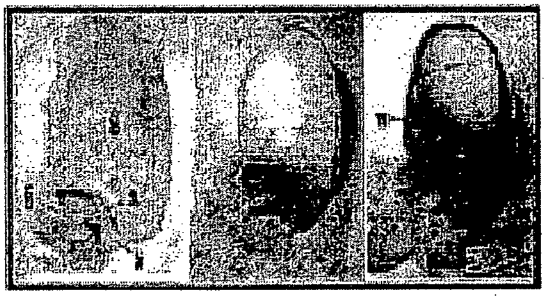

In one preferred approach, temporal expression of the recombinant protein takes place and is detected in particular seed tissues due to expression under the control of a promoter which directs tissue-preferential or tissue-specific expression. See FIG. 1A which illustrates various tissues of a cereal seed, FIG. 1B which outlines the life cycle of a cereal seed and FIGS. 1C-E which illustrate tissue-specific expression in the endosperm, embryo and alleurone tissues.

In practicing the invention, a plant cell may be transformed with one or more vectors, each comprising the coding sequence for one or more plant transcription factors, each operably linked to a tissue specific promoter, wherein the tissue specific promoters may be the same or different. It will be understood by those of skill in the art that once expressed a recombinant transcription factor may act on the promoter which is regulating expression of the transcription factor itself in addition to acting on one or more other promoters.

In one preferred embodiment, the plant transcription factor is expressed under the control of a seed specific promoter, which generally promotes selective expression in the endosperm, alleurone or embryo of a seed. In some cases, the transcription factor is expressed under the control of two or more different seed tissue-specific promoters at the same time in the same plant.

In a related embodiment, two or more transcription factors are expressed in the same cell and act in concert (in an additive, synergistic or inhibitory manner) to modulate expression of the gene to which they are operably linked. For example, when the opaque 2 (O2) and prolamin box binding factor (PBF) transcription factors are co-expressed, transcription is activated in an additive manner. (See, e.g., FIGS. 12B, 13B and 14B.)

In addition, when two or more transcription factors are expressed in the same cell, one transcription factor may activate expression of the other transcription factor.

In another preferred embodiment, a heterologous nucleic acid coding sequence for a first transcription factor under the control of a first seed specific promoter, and a heterologous nucleic acid coding sequence for a second transcription factor under the control of a second seed-specific promoter, are introduced into a plant cell. In such cases, the nucleic acid construct comprising the second transcription factor and the second seed specific promoter, may be in the same or a different vector from the nucleic acid construct comprising the first transcription factor and the first seed specific promoter.

Figure 12A:
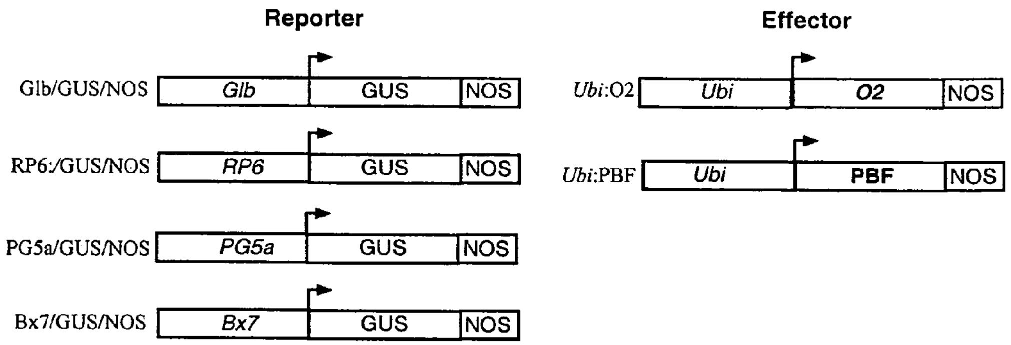
FIG. 12A illustrates reporter (Glb/GUS/NOS, RP6/GUS/NOS, PG5a/GUS/NOS and Bx7/GUS/NOS) and effector (Ubi:O2 and Ubi:PBF) plasmids used in transient expression assays.
Figure 12B:
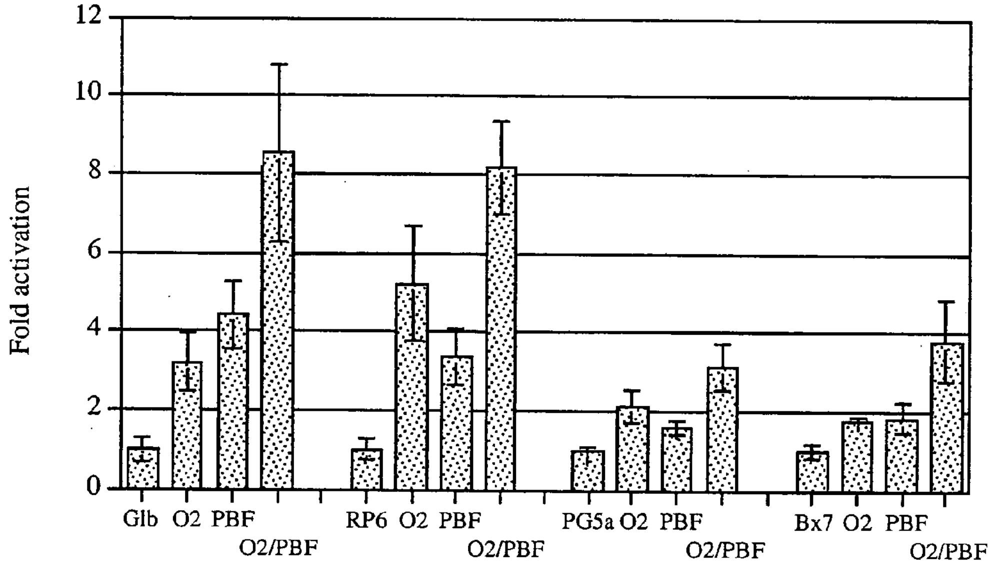
FIG. 12B presents the results of transient expression assays following particle bombardment of rice immature endosperms, where O2 and/or PBF were either: (1) independently expressed under the control of the (ubiquitin) Ubi promoter, Ubi:O2 and Ubi:PBF, respectively or (2) the Ubi:O2 and Ubi:PBF constructs were individually co-bombarded with Glb/GUS/NOS, RP6/GUS/NOS, PG5a/GUS/NOS or Bx7/GUS/NOS. All results are given relative to the GUS/LUX ratio of the Glb/GUS/NOS, RP6/GUS/NOS, PG5a/GUS/NOS or Bx7/GUS/NOS construct, respectively. Error bars represent the standard deviation of the mean value from at least five independent particle bombardments.
Figure 13A:
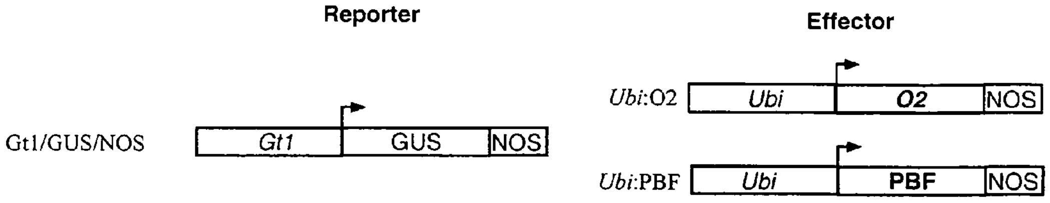
FIG. 13A is a schematic diagram of a reporter (Gt1/GUS/NOS) and effector (Ubi:O2 and Ubi:PBF) constructs used in transient expression assays.
Figure 13B:
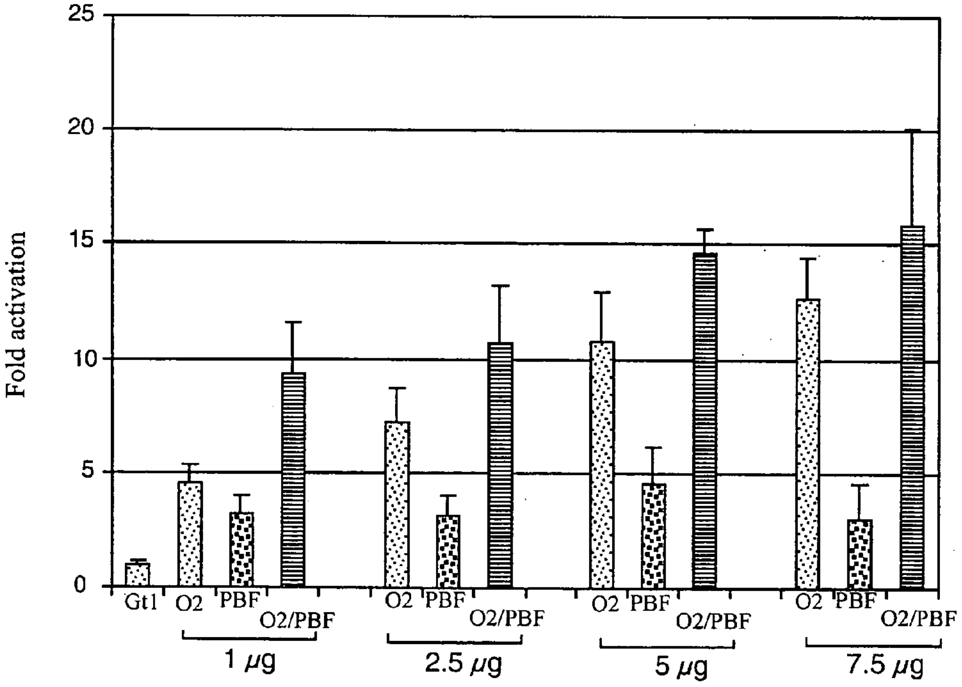
FIG. 13B presents the results of transient expression assays following particle bombardment of rice immature endosperms where O2 and PBF were either independently expressed under the control of the (ubiquitin) Ubi promoter, Ubi:O2 or Ubi:PBF, respectively; or the Ubi:O2 and Ubi:PBF constructs were individually co-bombarded with Gt1/GUS/NOS. All results are given relative to the GUS/LUX ratio of Gt1/GUS/NOS construct. Error bar represents the standard deviation of the mean value for at least five independent particle bombardments.
Figure 14A:
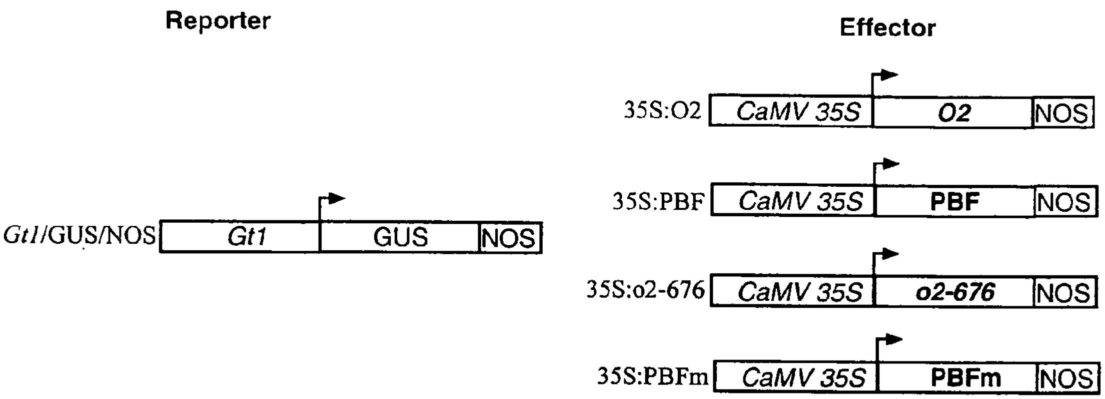
FIG. 14A is a schematic diagram of the reporter (Gt1/GUS/NOS) and effector (35S:O2, 35S:PBF, 35S: o2-676 and 35S:PBFm) constructs used in the transient expression assay.
Figure 14B:
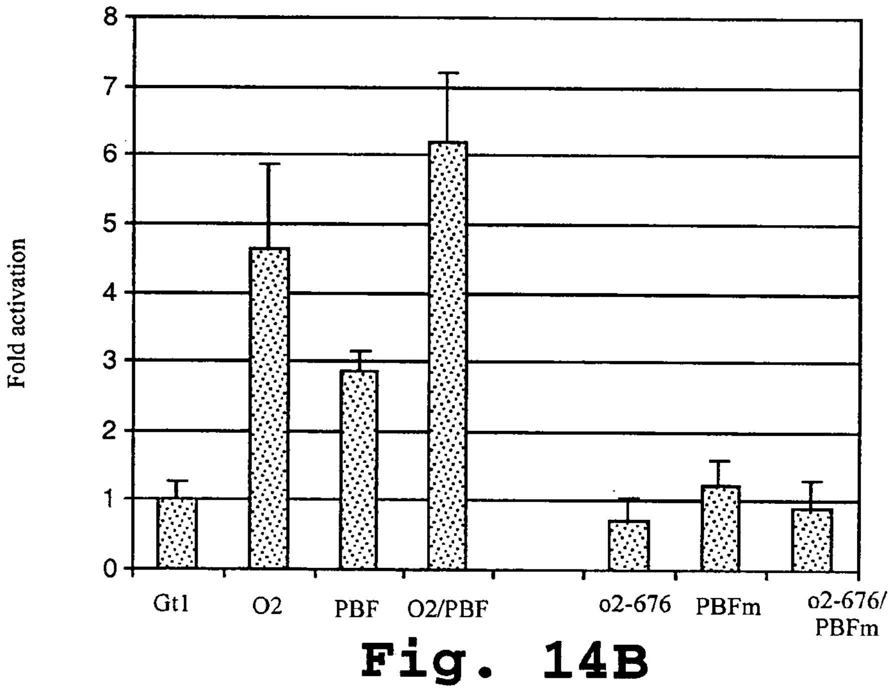
FIG. 14B presents the results of transient expression assays following particle bombardment of rice immature endosperms, with O2, PBF, o2-676 and PBFm expressed under the control of the 35S promoter (35S:O2), (35S:PBF); (35S: o2-676); and (35S:PBFm), respectively. In addition, the activation based on co-bombard of the combination of O2 plus PBF with Gt1/GUS/NOS was evaluated, as was the combination of o2-676 plus PBFm with Gt1/GUS/NOS. The pAHC18 (Ubi/LUC/NOS) plasmid was used as an internal control for all experiments. All results are given relative to the GUS/LUX ratio of Gt1/GUS/NOS construct. Error bar represents the standard deviation of the mean value for at least five independent particle bombardments.

It is preferred that expression of two or more transcription factors in the same plant results in a level of transgene expression which is greater than the expression of each transcription factor alone, when the transgene is under the control of a promoter with which the transcription factors interact. In other words, as exemplified herein, the level of expression observed when a transgene is expressed under the control of a promoter with which both the O2 and PBF transcription factors interact is greater than that the expression level observed due to either transcription factor alone. In this case the observed effect was additive, as shown in FIGS. 12B, 13B and 14B. It is within the scope of the present invention that any combination of two or more plant transcription factors be expressed in the same plant at the same time and result in a level of transgene expression that is additive or greater, when the transgene is under the control of a promoter with which the transcription factors interact.

In some cases a native promoter is non-responsive to a particular transcription factor. The present invention provides a method for modification of such a promoter to contain a response sequence or element with which the transcription factor may interact, as exemplified herein by the modification of the rice glutelin-1 (Gt-1) promoter to contain a 98 bp Reb upstream activation sequence (UAS fragment containing 3 copies of GCCACGT(C/A)AG (SEQ ID NO:36) amplified from the Glb promoter) inserted at position −630 bp distal to the TATA box of the Gt1 promoter in order to generate Gt1+UAS-GUS. The invention further provides seed specific promoters that have been modified to include the response sequence for a transcription factor not found in the native form of the promoter, wherein the modified seed specific promoter may be activated interaction with the transcription factor.

Transgenic plant cells transformed with a selected heterologous protein coding sequence under the control of a seed-specific promoter that is responsive to one or more transcription factors expressed in the cell are also provided by the invention. In some cases, a heterologous protein coding sequence is expressed under the control of two or more different seed-specific promoters at the same time in the same plant cell.

In one preferred aspect, the present invention provides transgenic plants wherein a plant transcription factor which interacts with one or more seed specific promoters is expressed in a monocot plant, resulting in a favorable modification in the production of native proteins expressed under the control of the seed specific promoter. For example, a transgenic plant may be constructed comprising the heterologous coding sequence for the O2 transcription factor, which upon expression interacts with any of a number of native seed specific promoters in the plant (e.g., a Glb promoter or a Bx7 promoter), resulting in enhanced expression of genes operably linked to the O2 responsive promoters.

In another preferred aspect, the invention provides methods for producing transgenic plant cells and transgenic plants that express a selected heterologous protein coding sequence under the control of a seed-specific promoter. In one approach, such plants are obtained by co-transformation of plant progenitor cells with one or more expression vectors effective to express (1) one or more plant transcription factors, and (2) a heterologous protein coding sequence under the control of one or more seed-specific promoters responsive to the one or more plant transcription factors. Following transformation, transformant are selected and regenerated to produce transgenic plants.

In another approach, transgenic plant lines, e.g., rice, wheat or barely, are developed and genetic crosses carried out using conventional plant breeding techniques. In one exemplary approach, a first stable transgenic plant line is generated where the plants express a transcription factor, e.g., O2, PBF or Reb, under the control of a seed-specific promoter. A number of such lines may be generated with varying levels of transcription factor expression. In practicing the method, these plants are crossed with a parental transgenic rice, corn, barley or wheat line that expresses a heterologous protein coding sequence (e.g., a recombinant protein) under the control of a seed-specific promoter that is responsive to the transcription factor expressed in the first plant line. Plants derived from the resulting cross (F2) have a higher expression level of the heterologous protein in one or more particular seed tissues, than a corresponding non-transgenic plant.

III. Plant Transcription Factors

Transcription factors are capable of sequence-specific interaction with a gene sequence or gene regulatory sequence. The interaction may be direct sequence-specific binding in that the transcription factor directly contacts the gene or gene regulatory sequence or indirect sequence-specific binding mediated by interaction of the transcription factor with other proteins. In some cases, the binding and/or effect of a transcription factor is influenced (in an additive, synergistic or inhibitory manner) by another transcription factor.

The gene or gene regulatory region and transcription factor may be derived from the same type of plant (e.g., the same species or genus) or a different type of plant.

The binding of a transcription factor to a gene sequence or gene regulatory sequence may be evaluated by a number of assays routinely employed by those of skill in the art, for example, sequence-specific binding may be evaluated directly using a label or through gel shift analysis.

The present invention involves the use of the maize Opaque 2 (O2) and prolamin box binding factor (PBF) together with the rice Reb protein as transcriptional activators of monocot storage protein genes.

A. Opaque 2

Zeins are the prolamin class of seed storage proteins that accumulate to high levels in mature seeds of maize (Mertz et al., 1964; Murphy et al., 1971; Lee et al., 1976). Several mutations are known to affect the accumulation of 22- and 19-kD zein proteins (reviewed in Motto et al., 1989). One of these mutations, Opaque 2 (O2), causes a severe reduction in the levels of zein gene transcripts encoding polypeptides of the 22-kD size class (Pedersen et al., 1980; Burr et al., 1982; Langridge et al., 1982). This reduction in zein protein accumulation causes the affected kernels to take on the characteristic "opaque" appearance that distinguishes the O2 phenotype from the normally translucent, vitreous endosperm of wild-type seed.

The O2 gene has been cloned (Schmidt et al., 1987; Motto et al., 1988). The subsequent isolation and sequencing of the O2 cDNA (Hartings et al., 1989; Schmidt et al., 1990) indicated that the O2 locus gene product contains a leucine-zipper DNA binding motif (Landschulz et al., 1988), which consists of a heptameric repeat of leucines (the "zipper"), responsible for dimer formation, adjacent to a cluster of positively charged amino acids (the "basic" motif), which are responsible for sequence-specific recognition of the target DNA (Neuberg et al., 1989; Turner et al., 1989). Proteins such as O2 that have a basic domain followed by a leucine-zipper DNA binding motif have been designated "bZIP proteins" (Vinson et al., 1989).

It has previously been shown that O2 is capable of binding to the promoter of 22-kD zein genes (Schmidt et al., 1990) and that the bZIP domain in O2 mediates this binding (Aukerman et al., 1991). DNA footprinting was used to identify the O2 binding site as 5'-TCCACGTAGA-3' (SEQ ID NO:40) (designated the "O2 box"). The site is located in the −300 region relative to the translation start and lies about 20 bp downstream of the highly conserved zein gene sequence motif known as the "prolamin box".

The results of gel shift assays using the O2 protein and extracts of endosperm indicate binding to the O2 target sequence. Additional studies have shown that O2 activates transcription from promoters derived from closely related zein genes when the promoters contain the O2 target sequence (Schmidt R et al., 1992). Gel mobility shift assays have indicated that O2 can bind partial "O2 box" sequences and that only the ACGT core sequence may be required for some degree of binding. However, a single base substitution in the O2 target site has been shown to be sufficient to inhibit DNA binding (Schmidt R et al., 1992).

A comparison of the O2 target sequence to upstream regions of the rice Glb promoter sequence indicates at least 3 potential O2 binding sites found in the −210 region (CCACGTA), the −220 region (CCACGT), and the −160 region (CCACGTA) (FIG. 9.) Similar sites have been identified in the wheat Bx7 promoter, shown in FIG. 10.

The nucleic acid sequence for the Opaque2 transcription factor may be found for example at GenBank Accession Nos. X15544 (opaque2 gene) and M29411 (opaque2 cDNA). In experiments carried out to demonstrate the present invention, the Opaque2 transcription factor coding sequence was cloned into expression vectors under the control of the rice glutelin-1 (Gt-1) and the maize ubiquitin promoters (Example 3).

The transient expression of O2 was shown to enhance the expression of GUS under the control of the rice Gt1, Globulin and wheat Bx7 promoters by approximately 10-fold (Example 3).

Further studies with the O2 protein suggested that O2 interacts in vivo with other endosperm proteins to bind zein gene promoters. A highly conserved 7-bp sequence (TGTAAAG) referred to as the Prolamin box (P-box) cis-element lies just 20 nucleotides upstream of the O2-box. This 7-bp sequence is referred to as the Prolamin box (P-box) due to its presence in the prolamins of corn, barley, wheat, oats, and sorghum (Forde et al., 1985).

B. Prolamin Box Binding Factor (PBF)

In general, in cereals, nitrogen and sulfur are stored mainly in a group of proteins called the prolamins, which are synthesized only in the endosperm under tissue-specific and temporal transcriptional control. The barley prolamins, called hordeins, are structurally similar to the prolamins from other grass species and it has been observed that putative regulatory elements in the barley hordein gene promoters are conserved (Forde B. G. et al., 1985; Kreis M. et al., 1985).

The P-box has been shown to be conserved in both its nucleotide sequence and in its position (about −300 bp) relative to the translation initiation codon of zein and other prolamin genes [VicenteCarbajosa, 1997; Müller et al., 1995; Albani et al., 1997; Forde et al., 1985; Hammond-Kosack et al., 1993].

A protein, named prolamin-box binding factor or PBF, was cloned in maize and found to bind to the P-box. PBF was shown to contain the highly conserved CYS2-CYS2 zinc finger motif characteristic of the DOF (DNA binding with One Finger) class of DNA-binding proteins (reviewed by Yanagisawa, 1996).

A barley PBF homologue, designated as BPBF (Barley Prolamin-Box Binding Factor) was isolated from a barley endosperm library (Montana Menal et al., 1998). An exemplary barley PBF (BPBF) coding sequence may be found at GenBank Accession Number AJ000991 (barley cDNA). The rice PBF and maize PBF coding sequences may be found for example at GenBank Accession numbers D11385 (rice cDNA) and ZMU82230 (maize cDNA). The rice PBF and maize PBF coding sequences were cloned into an expression vector under the control of the rice glutelin-1 (Gt-1) promoter (FIG. 11A, barley; FIG. 11B, maize).

The promoter regions from the rice glutelin genes Gt1, Gt3, GluB-1 and GluB-2; the rice prolamin genes RP6 and PG5a; the rice globulin gene Glb and the wheat glutelin gene, Bx7 were PCR amplified and cloned into the GUS reporter cassette of pBI221, as detailed in Example 3.

Transcription factor ("effector") plasmids were prepared with the O2 and PBF coding sequences under the control of the CaMV 35S promoter, the maize ubiquitin or the rice glutelin Gt1 promoter (SEQ ID NO:26). Transient assays using rice endosperm were carried out as described in Example 2, to evaluate the effector activity of the O2 and PBF transcription factors on GUS expression of heterologous nucleic acid constructs. Co-transfection with heterologous nucleic acid constructs comprising O2 and PBF, respectively, resulted in an additive increase in transactivation of the promoters from rice storage protein genes including Gt1, Gt3, GluB-1 and GluB-2; the rice prolamin genes RP6 and PG5a; the rice globulin gene Glb and the wheat glutelin gene, Bx, as summarized in Table 2, suggesting that the maize O2 and PBF proteins can act singly or additively as effective stimulators of heterologous storage protein promoters in developing rice seed (See Example 3.). An additive increase in transactivation was observed by co-bombardment of both effector plasmids and was observed in all the promoters of storage protein genes that were tested, while the responsiveness of non-storage protein genes like rice actin and CaMV35S to O2 and PBF was insignificant (Example 3).

When assayed in developing rice endosperm cells, both O2 and PBF were shown to individually increase transcription of a GUS reporter under the control of the rice glutelin gene, Gt1, however, mutant forms of O2 and PBF, defective in DNA binding, did not function as transcriptional activators. In addition, co-bombardment of Gt1/GUS/NOS with plasmids expressing the DNA binding domains for O2 and PBF in antisense orientation resulted in expression of Gt1/GUS/NOS that was below background levels.

C. Reb

In cereals bZIP proteins have been identified as transcriptional factors for genes encoding storage proteins in the endosperm [VicenteCarbajosa, 1998; Schmidt, 1992; Conlan, 1999; Holdsworth, 1995; Liu, 1998; Mena, 1998; Onate, 1999; Schwechheimer, 1998; Schwechheimer, 1998; Wang, 1998; Yunes, 1994]. The basic amino acid containing domain of bZIP proteins has been demonstrated to bind to a recognition nucleotide sequence in the promoter, while their leucine repeat domain interacts with the transcriptional machinery leading to a dramatic increase in transcription initiation of the storage protein-encoding gene in the endosperm of the cereal grain. [See, e.g., Mena, 1998 and Schmidt, 1992].

Nakase et al., 1997, have described a cloned bZIP protein gene from rice, named Reb for rice endosperm bZIP protein. Reb was demonstrated to bind specifically to the sequences GCCACGTAAG (SEQ ID NO:37) and GCCACGTCAG (SEQ ID NO:38) in the distal part of the rice globulin (Glb) gene promoter, however, its function as a transcriptional activator or suppressor was not described. The complete coding sequence for Reb, isolated from rice endosperm may be found at GenBank Accession number ABO21736. (Nakase et al., 1997.)

Figure 3:
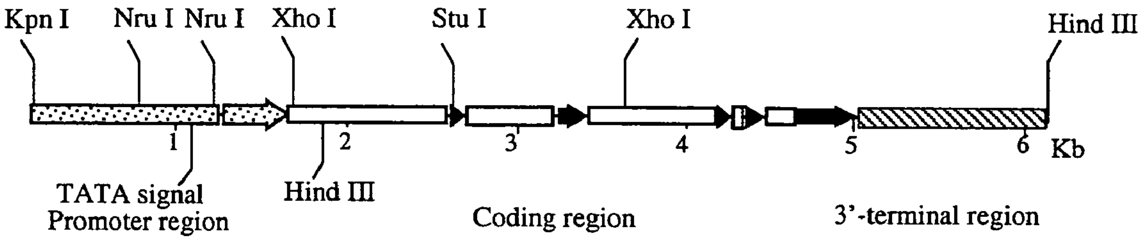
FIG. 3 presents a restriction map of the rice Reb gene isolated from BAC clone 42B9.
Figure 5A:
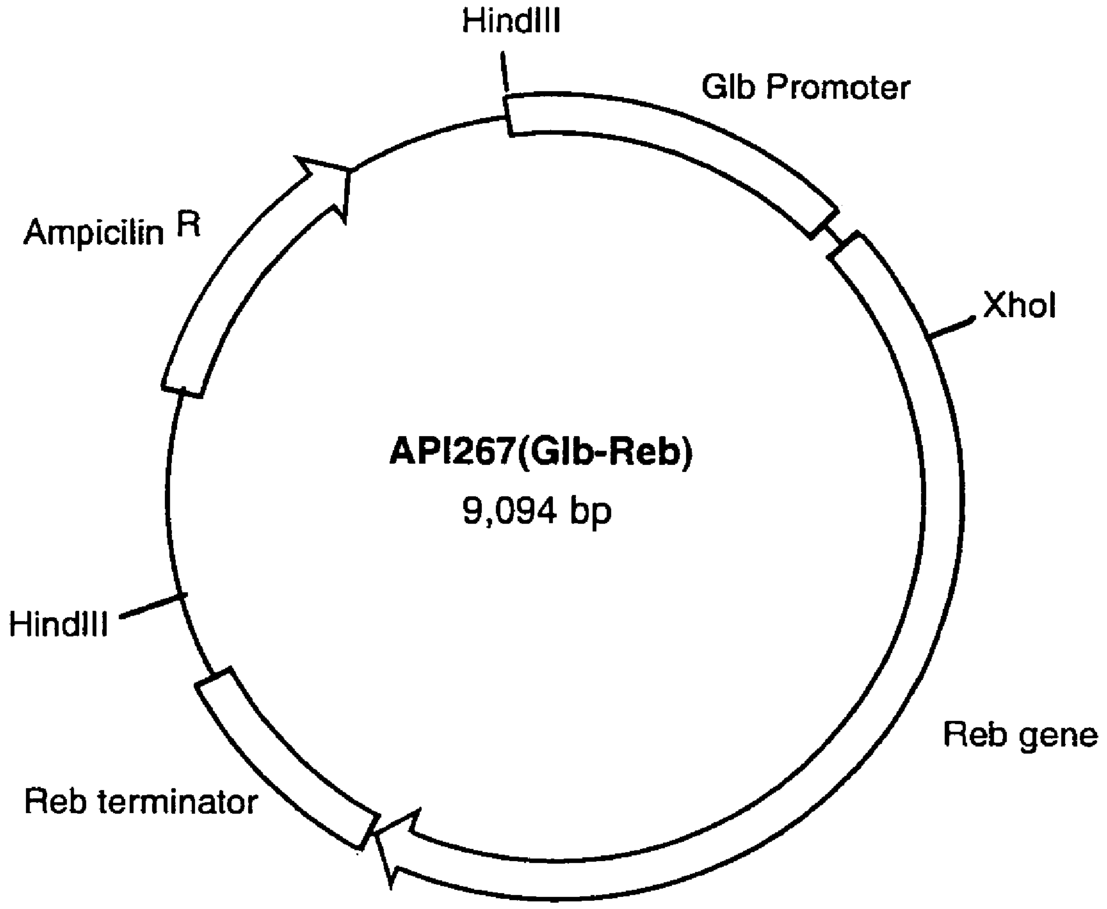
FIGS. 5A-C present a schematic diagram of 3 plasmids which contain the Reb coding sequence under the control of (A) the globulin promoter (Glb), (B) the actin promoter (Act) and (C) the native Reb promoter.
Figure 5B:
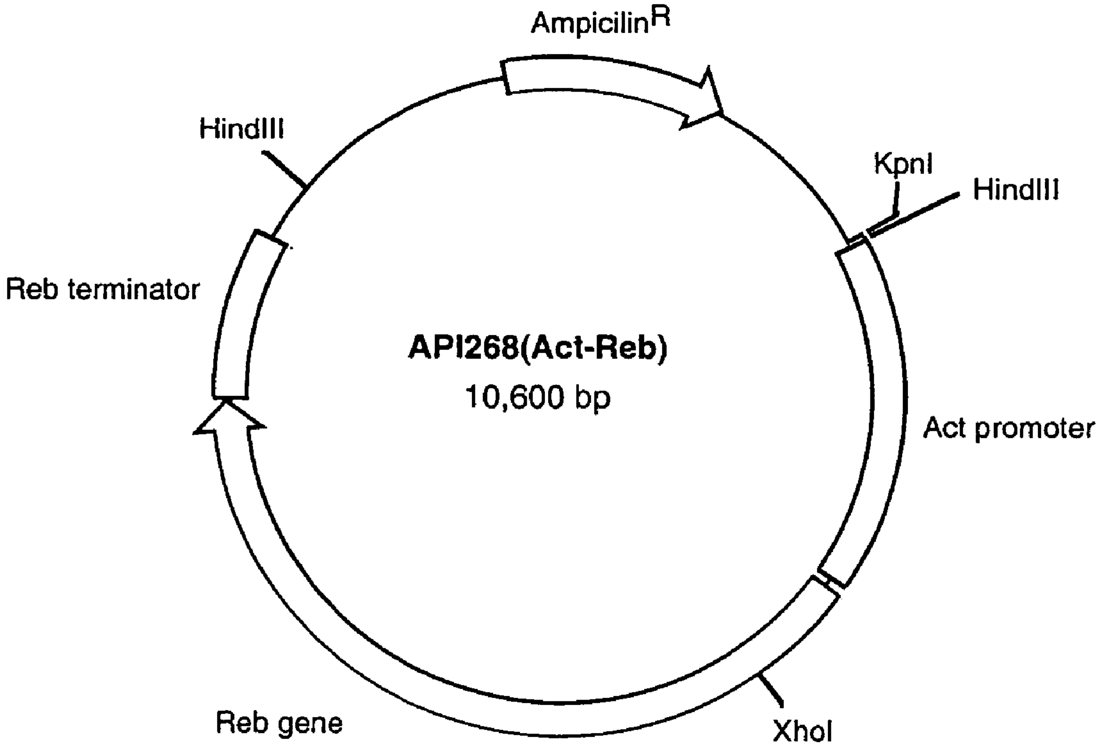
Figure 5C:
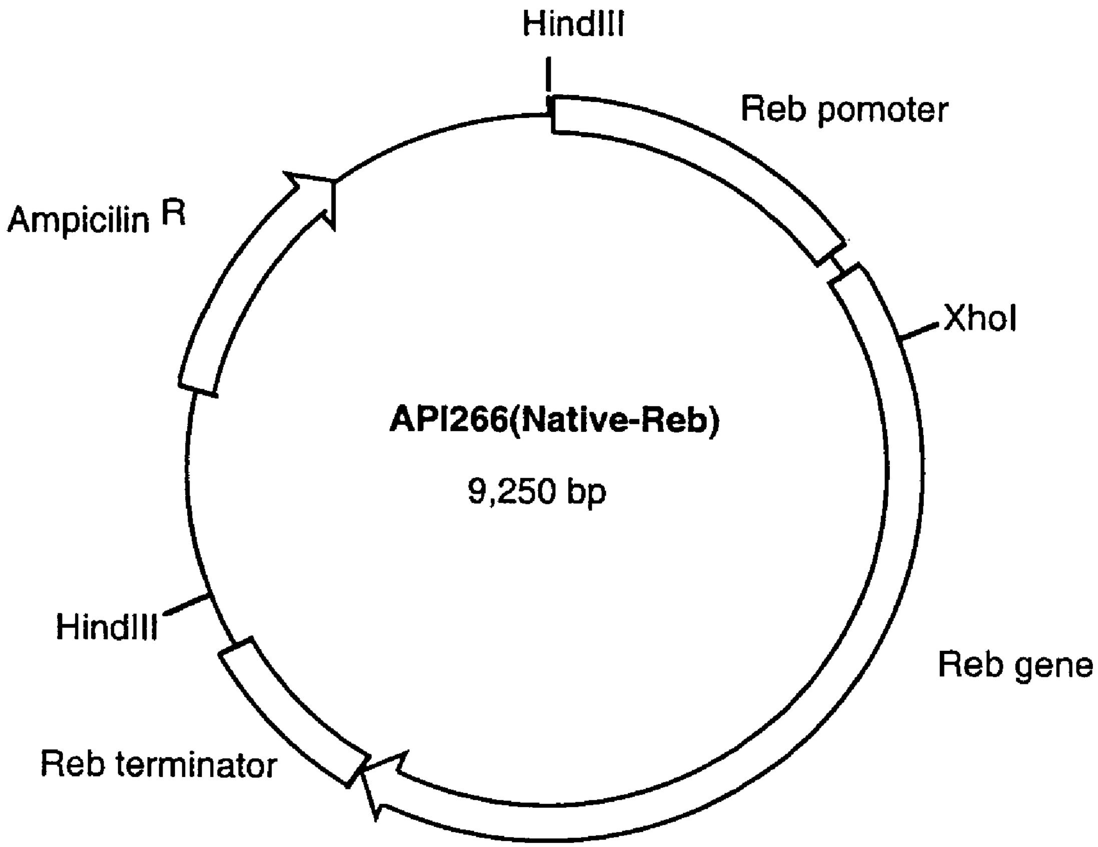

Reb was cloned from a rice BAC library and the function of the Reb gene explored. FIGS. 2A-I present a double-stranded depiction of the DNA sequence of the rice (*Oryza sativa*) Reb bZIP protein. The Reb gene sequence of 6.227 kb consists of 5 introns and 6 exons flanked by 1.2 kb of the 5' promoter and 1.2 kb of the 3' region (FIG. 3). Effector constructs containing the Reb gene together with the native Reb promoter and fusion genes linking Reb to the globulin (Glb) gene promoter, the rice actin (Act) promoter or the native Reb promoter were prepared and used to identify Reb as a transcriptional activator. (See FIGS. 5A-C.)

Individual plasmids carrying the rice globulin (Glb) gene promoter fused to the GUS reporter gene and the rice glutelin 1 (Gt-1) gene promoter fused to the GUS reporter gene, respectively were constructed using standard molecular biological techniques and used for transient expression assays, as detailed in Example 2.

The endosperms of rice spikelets (7-9 days after pollination, DAP) of M2O2 (*Oryza sativa Japonica* subsp.) collected from greenhouse grown plants were bombarded with gold particles coated with DNA consisting of a mixture of the reporter gene, effector gene, and an internal control gene, typically at a molar ratio of 1:1:1. After bombardment, the immature endosperms were incubated, harvested and analyzed for GUS expression.

Figure 6A:
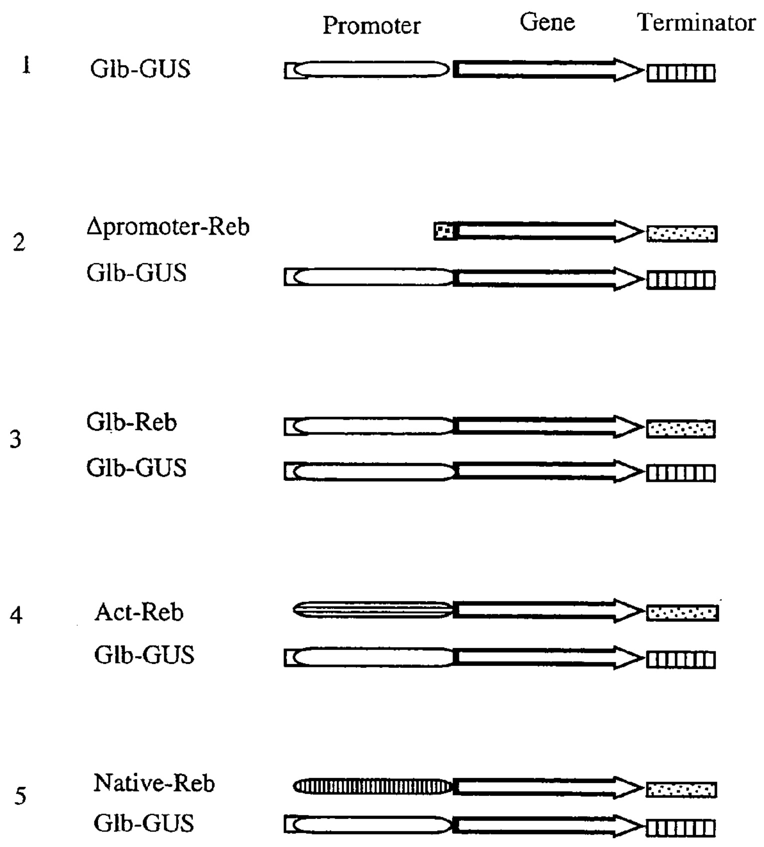
FIG. 6A presents a schematic diagram of the plasmid constructs used for transient assays illustrating the transactivation function of the Reb gene towards the Glb promoter where (1) is a GUS reporter construct with GUS expressed under the control of the Glb promoter (Glb-GUS-Nos); (2) is a null promoter construct (Δpromoter-Reb-Term) where the cells were co-bombarded with the Glb-GUS reporter gene construct; (3) is an Reb expression construct with Reb expressed under the control of the Glb promoter (Glb-Reb-Term), where the cells were co-bombarded with the Glb-GUS-Nos reporter gene construct; (4) is an Reb expression construct with Reb expressed under the control of the Actin promoter (Act-Reb-Term) where the cells were co-bombarded with the Glb-GUS-Nos reporter gene construct; and (5) is an Reb expression construct with Reb expressed under the control of the native Reb promoter (Native-Reb-Term), where the cells were co-bombarded with the Glb-GUS-Nos reporter gene construct.
Figure 6B:
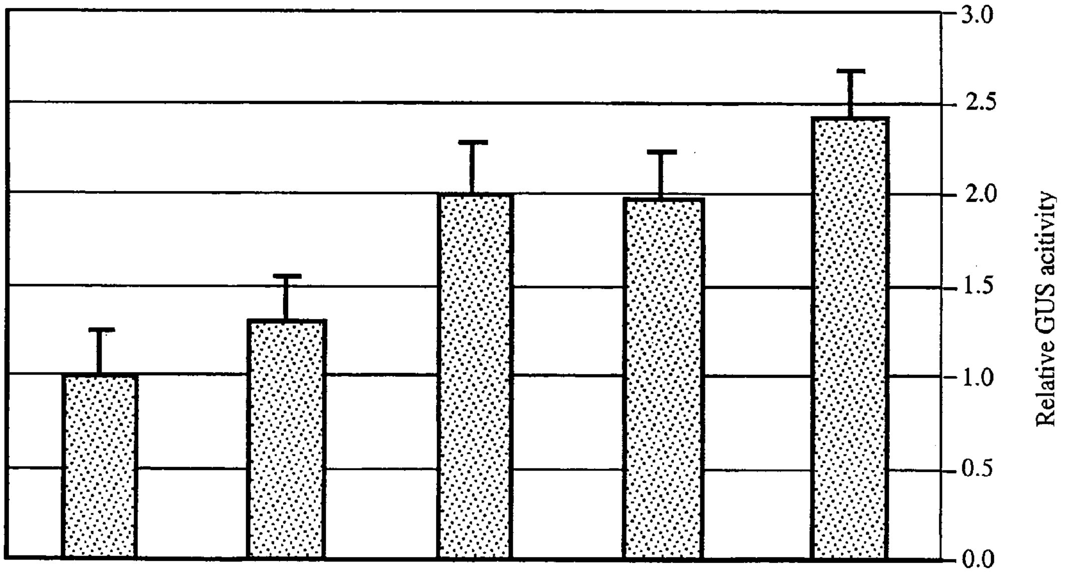
FIG. 6B illustrates the relative GUS activity as measured in transient expression assays using the effector/reporter combinations shown in FIG. 6A.

The results shown in FIG. 6B indicate that GUS expression was increased when Reb was expressed under the control of the globulin promoter, the actin promoter or the native Reb promoter (FIGS. 5A-C) suggesting that Reb is effective to an activate expression mediated by Glb promoter.

The upstream activation sequence (UAS) for Reb was identified using a band-shift assay (Nakase et al., 1997). The Glb promoter sequence which contains the UAS and the Gt-1 promoter which does not, were used to demonstrate transcriptional activation by Reb through the UAS by loss-of-function and gain-of-function experiments (Example 2).

The results described in Examples 1 and 2 show that (1) Reb is a transcriptional activator; (2) Reb specifically activates the Glb promoter but not gluletin (Gt-1) gene family promoters; and (3) Reb interacts with an approximately 100 bp upstream activation sequence (UAS) containing the motifs GCCACGTCAG (SEQ ID NO:38) and GCCACGTAAG (SEQ ID NO:37) (GCCACGT(A/C)AG) (SEQ ID NO:36) of the Glb promoter, as confirmed by loss-of-function and gain-of-function experiments.

IV. Heterologous Nucleic Acid Constructs

A. Constructs for Expression of a Transcription Factor in a Plant Cell

A heterologous nucleic acid construct or expression vector designed for operation in plants comprising the coding sequence for a plant transcription factor may be used to transiently or stably transform a plant, e.g. a monocot plant. An exemplary heterologous nucleic acid construct or expression vector designed for operation in plants, includes (i) a promoter (transcriptional regulatory region) induced in particular seed tissue ("seed-specific"), (ii) the coding sequence for a plant transcription factor operably linked to the promoter, (iii) companion sequences upstream and downstream which are of plasmid or viral origin and provide necessary characteristics to the vector to permit the vector to move the DNA from bacteria to the desired plant host; (iv) a selectable marker sequence; and (v) a transcriptional termination region generally at the opposite end of the vector from the transcription initiation regulatory region. Suitable transformation vectors for the preparation of such constructs are known in the art and many are commercially available.

Vector components may also include a signal sequence. The desired recombinant protein or polypeptide may be produced directly, or as a fusion polypeptide with a heterologous polypeptide, which may be a signal sequence or other polypeptide having a specific cleavage site at the N-terminus of the mature protein or polypeptide. Included in heterologous nucleic acid constructs for use in the methods of the invention are signal sequences that allow processing and translocation of the protein, as appropriate. The heterologous nucleic acid construct typically lacks any sequence that might result in the binding of the desired protein to a membrane.

In some cases, the recombinant protein may be produced as a precursor protein, which may be further processed in the plant cell culture or following extraction from the plant.

B. Expression Vector Components

1. Seed-Specific Promoters

The transcription regulatory or promoter region of the chimeric gene or heterologous nucleic acid construct is preferably a seed-specific promoter, for example, a promoter capable of directing expression of a gene product under its control, which is specific to the seed embryo, alleurone, outer layer of the endosperm or center of the endosperm; or a promoter capable of directing expression of a gene product under its control, which is specific to starch or protein synthesis.

Exemplary preferred promoters include a glutelin (Gt-1) promoter which effects gene expression in the outer layer of the endosperm and a globulin (Glb) promoter which effects gene expression in the center of the endosperm. Promoter sequences for regulating transcription of operably linked coding sequences include naturally-occurring promoters, or regions thereof capable of directing seed-specific transcription, and hybrid promoters, which combine elements of more than one promoter. Methods for construction of hybrid promoters are well known in the art.

In some cases, the promoter is derived from the same plant species as the plant in which the nucleic acid construct is to be introduced. Promoters for use in the invention are typically derived from cereals such as rice, barley, wheat, oat, rye, millet, triticale or sorghum.

Alternatively, a seed-specific promoter from one type of monocot may be used regulate transcription of a gene coding sequence from a different monocot or a non-cereal monocot. Numerous types of appropriate expression vectors, and suitable regulatory sequences are known in the art for a variety of plant host cells. In general, the transcriptional and translational regulatory sequences may include, but are not limited to, promoter sequences, ribosomal binding sites, transcriptional start and stop sequences, translational start and stop sequences, and enhancer or activator sequences.

Effective seed-inducible or seed-regulated transcriptional initiation regions (e.g., promoters) may be isolated from various seed tissues and/or at various stages of seed development by a variety of techniques routinely used by those of skill in the art, including, but not limited to: (1) conventional hybridization techniques using known coding sequences from a different species, tissue and/or developmental stage, followed by walking upstream to identify the associated transcriptional initiation sequence; (2) subtractive hybridization (Lee, et al., 1991), (3) differential display (Liang et al., 1997), and (4) selective amplification via biotin- and restriction-mediated enrichment, SABRE (Lavery et al., 1997).

Promoters from seed tissue specific genes such as those described in Müller et al., 1993, are suitable for use in the chimeric gene constructs described herein. More specifically, representative seed-associated promoters for use in the invention include the promoters from the rice glutelin multigene family, Gt1, Gt2, Gt3, GluA-3, and GluB-1. Promoter regions for these genes are described, for example, in Takaiwa, et al., 1987 (rice glutelin gene, GenBank Accession Nos. D26365 and D26364), Takaiwa, et al., 1991 (rice GluA-3 gene, GenBank Accession No. X54313), Takaiwa, et al., 1991a (rice glutelin gene, GenBank Accession No. Y00687), Takaiwa, et al, 1991 b (rice Glu-B gene, GenBank Accession No. X54193; rice GluB-2 gene, GenBank Accession No. X54192); rice GluB-1 gene (GenBank Accession No. X54314); Okita, et al., 1989 (rice Gt2 gene, GenBank Accession No. L36819 M28157); rice Gt3 gene, (GenBank Accession No. M28158); rice Gt1 gene (GenBank Accession No. M28156); rice glutelin gene (GenBank Accession Nos. D26363, D26366+D26367, D26368 and D26369); Abe, et al., 1989 (rice prepro-glutelin gene, GenBank Accession No. D00584); Kim and Wu, 1990 (rice glutelin gene, GenBank Accession No. X52153). In general, these promoters are active during seed development and direct endosperm-specific expression (Takaiwa et al., 1991a, 1991b; Okita et al., 1989; Abe et al., 1989; Kim and Wu, 1990).

Other suitable seed-associated promoters include the promoter regions from the rice prolamin gene (GenBank Accession No. D73384; Nakase et al., 1996); the barley B22EL8 gene promoter, which directs expression in immature aleurone layers (Klemsdal et al, 1991); the promoter for the barley LTp gene (GenBank Accession No. X57270); the barley β-amylase (Kreis et al., 1987; GenBank Accession No. X52321 and M36599) and β-glucanase gene promoters (Wolf 1992) e.g., the barley Glb gene promoter (GenBank Accession No. X56775); the barley CMd gene promoter (Halford et al., 1988; GenBank Accession No. X13198), and promoters from the barley hordein gene family of seed storage proteins, e.g., B-, C-, and D-hordein genes (Sorensen, et al., 1996 and references therein), Brandt, et al., 1985 (hordein B1 gene promoter, GenBank Accession No. X87232), Entwistle, 1988 (barley hordein C promoter, GenBank Accession No. M36941), and Müller et al., 1993 (barley hor1-17 gene, GenBank Accession No. X60037). Hordein gene promoters such as the Hor3 gene promoter (Sorensen et al, 1996; GenBank Accession No. X84368) direct the specific expression of the corresponding genes in the endosperm. Additional seed-induced promoters for use in the invention are the maize zein gene promoter and promoters from wheat glutenin genes. Representative wheat glutenin gene sequences as sources for promoters for use in practicing the present invention include GenBank Accession Nos. U86O28, U86O29, and U86O30.

Seed-associated corn promoters also find use in the present invention. For example, the corn O2-opaque 2 gene promoter (Schmidt et al., 1987, GenBank Accession No. M29411); the corn Sh2-shrunken 2 gene promoter (Shaw et al., 1994, GenBank Accession No. S48563); the Bt2-brittle 2 gene promoter; and the Zp1 zein gene promoter (Burr et al., 1982), all of which induce endosperm-specific expression. Additional examples include the Agp1 and Agp2 gene promoters (Giroux et al., 1994), which are embryo-specific promoters. The sequences of the above-described promoters, and/or the structural sequences from which such promoters may obtained, are expressly incorporated by reference herein.

Any of the above promoters may also be obtained from an alternative monocot species. For example, a promoter such as the Gt1 gene promoter from rice may be isolated from other cereal-derived nucleic acid containing extracts, e.g., wheat, oat, or the like, using conventional hybridization techniques known in the art.

2. Coding Sequence

The heterologous nucleic acid constructs described herein may comprise the coding sequence for a plant transcription factor, as further described above for O2, PBF, BPBF and Reb. (See, also Example 1.)

Alternatively, the heterologous nucleic acid constructs described herein may comprise a heterologous protein or transgene coding sequence. Exemplary heterologous protein coding sequences include, but are not limited to, the coding sequence for a human milk protein e.g., lactoferrin or lysozyme.

3. Expression Vector Components

Expression vectors or heterologous nucleic acid constructs, designed for operation in plants, comprise companion sequences upstream and downstream from the expression cassette. The companion sequences are of plasmid or viral origin and provide necessary characteristics to the vector to permit the vector to move DNA from bacteria to the plant host, such as, sequences containing an origin of replication and a selectable marker. Typical secondary hosts include bacteria and yeast.

In one embodiment, the secondary host is *E. coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The transcriptional termination region may be taken from a gene where it is normally associated with the transcriptional initiation region or may be taken from a different gene. Exemplary transcriptional termination regions include the NOS terminator from *Agrobacterium* Ti plasmid and the rice α-amylase gene terminator.

Polyadenylation signals (Alber et al., 1982) may also be added to the expression cassette to optimize high levels of transcription and proper transcription termination, respectively. Polyadenylation sequences include but are not limited to the *Agrobacterium* octopine synthetase signal (Gielen et al., 1984) or the nopaline synthase of the same species (Depicker et al, 1982).

Suitable selectable markers for selection in plant cells include, but are not limited to, antibiotic resistance genes, such as, kanamycin (nptII), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed is one that allows for selection of transformed cells as compared to cells lacking the DNA that has been introduced. Preferably, the selectable marker gene is one that facilitates selection at the tissue culture stage, e.g., a kanamycin, hygromycin or ampicillin resistance gene.

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

In general, a selected nucleic acid sequence is inserted into an appropriate restriction endonuclease site or sites in the vector. Standard methods for cutting, ligating and *E. coli* transformation, known to those of skill in the art, are used in constructing vectors for use in the present invention. Generally, vectors for use in practicing the present invention are constructed using methods known to those skilled in the art. See generally, Maniatis et al., 1989; Ausubel et al., (c) 1987, 1988, 1989, 1990, 1993, and Gelvin, S. B., et al., 1990, all three of which are expressly incorporated by reference, herein.

V. Generation of Transgenic Plants

A. Plants

The plants used in practicing the invention are generally of monocot origin, particularly the members of the taxonomic family known as the Gramineae. This family includes all members of the grass family of which the edible varieties are known as cereals or grains. The cereals include a wide variety of species such as wheat (*Triticum* sps.), rice (*Oryza* sps.), barley (*Hordeum* sps.), oats (*Avena* sps.), rye (*Secale* sps.), corn (*Zea* sps.), and millet (*Pennisettum* sps.). In one embodiment of the invention, preferred family members are rice, wheat and barley.

Plant cells or tissues derived from the members of the family may be transformed with expression vectors (i.e., plasmid DNA into which the gene of interest has been inserted) using a variety of standard techniques (e.g., microparticle bombardment, electroporation, protoplast fusion or infection with *Agrobacterium*).

Transgenic plant cells obtained as a result of such transformation express the coding sequence for a plant transcription factor such as Reb, O2 or PBF. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art.

In one embodiment of the invention, transgenic plant lines, e.g., rice, corn, wheat or barely, are developed and genetic crosses carried out using conventional plant breeding techniques. In one example of this approach, a first stable transgenic plant line is generated where the plants express a transcription factor, e.g., O2, PBF or Reb, under the control of a seed-specific promoter. A number of such lines may be generated with varying levels of transcription factor expression. The plants are crossed with a second transgenic plant line that expresses a heterologous protein coding sequence (e.g., a recombinant protein) under the control of a seed-specific promoter that is responsive to the transcription factor expressed in the first plant line. The resulting cross (F2) has a higher expression level of the heterologous protein in one or more particular seed tissues, dependent upon the promoter used.

B. Transformation of Plant Cells

Vectors useful in the practice of the present invention may be microinjected directly into plant cells by use of micropipettes to mechanically transfer the nucleic acid construct or cassette (Crossway, 1985). Such nucleic acid constructs or cassettes may also be transferred into the plant cell using polyethylene glycol. In addition, high velocity ballistic penetration by small particles with the nucleic acid either within the matrix of small beads or particles, or on the surface may also be used for introduction of nucleic acid sequences into plant cells. (See, e.g., Klein et al., 1987 and Knudsen et al., 1991).

Additional methods for introduction of nucleic acid sequences into plant cells include fusion of protoplasts with other entities, either minicells, cells, lysosomes or other fusible forms for introduction of nucleic acid sequences into plant cells with lipid surfaces (Fraley et al, 1982); and electroporation (From et al., 1985). In this technique, electrical impulses of high field strength reversibly permeabilize biomembranes allowing the introduction of plasmids into plant cells or protoplasts. Electroporated plant protoplasts will reform the cell wall, divide, and form plant callus.

Another preferred method of introducing a nucleic acid construct into plant cells is to infect a plant cell, explant, meristem or seed with *Agrobacterium*, in particular *Agrobacterium tumefaciens*. A nucleic acid construct comprising such a sequence of interest can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., 1984; Fraley et al., 1983; Schell, 1987).

Standard *Agrobacterium* binary vectors are known to those of skill in the art and many are commercially available. Expression vectors typically include polyadenylation sites, translation regulatory sequences (e.g., translation start sites), introns and splice sites, enhancer sequences (which can be inducible, tissue specific or constitutive), and may further include 5' and 3' regulatory and flanking sequences.

An exemplary binary vector suitable for use in practicing the invention include at least one T-DNA border sequence (left, right or both); restriction endonuclease sites for the addition of one or more heterologous nucleic acid coding sequences [adjacent flanking T-DNA border sequence(s)]; a heterologous nucleic acid coding sequence (i.e., the sequence encoding a protein or polypeptide of interest), operably linked to appropriate regulatory sequences and to the directional T-DNA border sequences; a selectable marker-encoding nucleotide sequence which is functional in plant cells, operably linked to a promoter effective to express the selectable marker encoding sequence; a termination element for the selectable marker-encoding nucleotide sequence; a heterologous Ti-plasmid promoter; a nucleic acid sequence which facilitates replication in a secondary host (e.g., an *E. coli* origin of replication) and a nucleic acid sequence for selection in the secondary host, i.e., *E. coli.*

In one aspect of the invention, an *Agrobacterium* binary plant transformation vector is introduced into a disarmed strain of *A. tumefaciens* by electroporation (Nagel, et al., 1990), followed by co-cultivation with plant cells, to transfer the heterologous nucleic acid construct(s) into plant cells. Upon infection by *Agrobacterium tumefaciens*, the heterologous DNA sequence is stably integrated into the plant genome in one or more locations.

In a further aspect of the invention, transgenic plants are produced using *Agrobacterium* T-DNA vectors or microprojectile bombardment, where a heterologous nucleic acid coding sequence is integrated into the plant genome and traditional breeding is used to generate transgenic seed stock and transgenic plants.

Suitable selectable markers for selection in plant cells are described above and the particular marker gene employed is one which allows for selection of transformed cells as compared to cells lacking the DNA which has been introduced. Preferably, the selectable marker gene is one which facilitates selection at the tissue culture stage, e.g., a kanamycin, hygromycin or ampicillin resistance gene.

Transformed explant cells are screened for the ability to be cultured in selective media having a threshold concentration of selective agent. Explants that can grow on the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plant cells with expression of modified native or non-native plant genes and regeneration of transgenic plants, which can produce a recombinant protein or polypeptide of interest.

The expression of a recombinant protein or polypeptide can be confirmed using any of a number of standard analytical techniques such as Western blot, ELISA, PCR, HPLC, NMR, or mass spectroscopy.

VI. Utility

The results presented herein suggest that the expression of the cDNA for the maize transcription factor cDNA encoding opaque 2 (O2) and/or the prolamin box binding factor (PBF) find utility in the enhanced gene expression of a coding sequence under the control of a promoter with which the transcription factor interacts. An approximately 10 fold enhancement of expression is observed when O2 or PBF is expressed under the control of a rice Gt1, Globulin or wheat Bx7 promoter. The results also suggest the utility of co-expression of the O2 and PBF transacting factors for further enhancement of gene expression and that co-expression of one or more transcription factors together with a heterologous protein coding sequence under the control of a promoter responsive to the one or more transcription factors may facilitate enhanced recombinant protein expression.

Such co-expression may be accomplished by development of transgenic plant lines which express one or more transcription factors together with the heterologous protein coding sequence or by genetic crosses of plant lines which express individual transcription factors with plant lines that express the heterologous protein coding sequence.

Accordingly, the expression of specific transcription factors in transgenic plants, as described herein, provides a means to increase the expression of recombinant proteins in cereal grains.

All publications, patents and patent applications are herein expressly incorporated by reference in their entirety to the same extent as if each individual publication, patent or patent application was specifically and individually indicated to be incorporated by reference in its entirety.

The following examples illustrate but are not intended in any way to limit the invention.

Example 1

Plant Transcription Factors

A. Cloning of the Reb Gene from a Rice BAC Library

Reb was cloned from a rice BAC library. The Reb gene including the introns, promoter and 3'-UTR region is 6,227 bp long, comprises 6 exons and 5 introns and is flanked by a 1.2 kb 5' promoter and a 1.2 kb 3'-terminator region. The function of the Reb gene was explored using effector constructs containing the Reb gene together with the native Reb promoter and fusion genes linking Reb to the rice actin (Act) or globulin (Glb) gene promoters. (See FIG. 6A-B.)

PCR primers were designed based on the Reb gene sequence provided in Nakase, 1997 and used to screen a rice bacterial artificial chromosome (BAC) library [Yang, 1997] using a screening strategy for tri-dimensional DNA pools of the BAC library as described by Xu, 1998.

PCR was carried out with 100 ng pooled BAC DNA, 10 mM Tris (pH 8.3), 1.5 mM $MgCl_2$, 50 mM KCl, 0.5 μM dNTP and employed a program of denaturing at 94° C. for 5 min followed by 30 cycles of 94° C. for 45 seconds, 60° C. for 45 seconds and 72° C. for 1 min, using a forward primer (5'-CTGATATGTGCCCATGTTCCAAAC-3'; SEQ ID NO:1) and a reverse primer (5'-CCTTGCTGAATGCAGATGTTTCAC-3'; SEQ ID NO:2). The plasmid DNA of a positive BAC clone was prepared as described [Yang, 1997], the BAC DNA digested with HindIII and the presence of the Reb gene confirmed by Southern analysis [Sambrook J., 1989].

The Reb gene was retrieved from the BAC by subcloning two fragments into the pBluescript KS+ vector (Stratagene, CA). First, the promoter and partial coding region was obtained as a KpnI-HindIII fragment, followed by a second step where a HindIII fragment containing the remaining coding region and the 3' terminator region was obtained by shutgun cloning. The two fragments were ligated at the internal HindIII site generating an intact Reb gene and the complete Reb gene was generated by ligating a 1,775 bp fragment containing the promoter and the 5' coding region, to a 4,452 bp fragment containing the 3' coding and terminator region.

The Reb DNA was sequenced with an automatic DNA sequencer (ABI 371) which revealed 5 introns, 6 exons, 1.16 kb of the 5' promoter sequence and 1.2 kb of the 3' region totaling 6,227 bp. (FIG. 2A-I). A comparison of the open reading frame of the isolated Reb gene with the Reb cDNA gene found at GenBank Accession No. ABO21737 revealed 99.97% DNA sequence similarity and 99.99% amino acid similarity resulting from two amino acid changes: $Ile_{165}$→Asn and $Glu_{215}$→Lys. These differences are likely to be due to polymorphisms among rice varieties.

B. Opaque2 (O2) and Prolamin Box Factor (PBF)

Figure 11A:
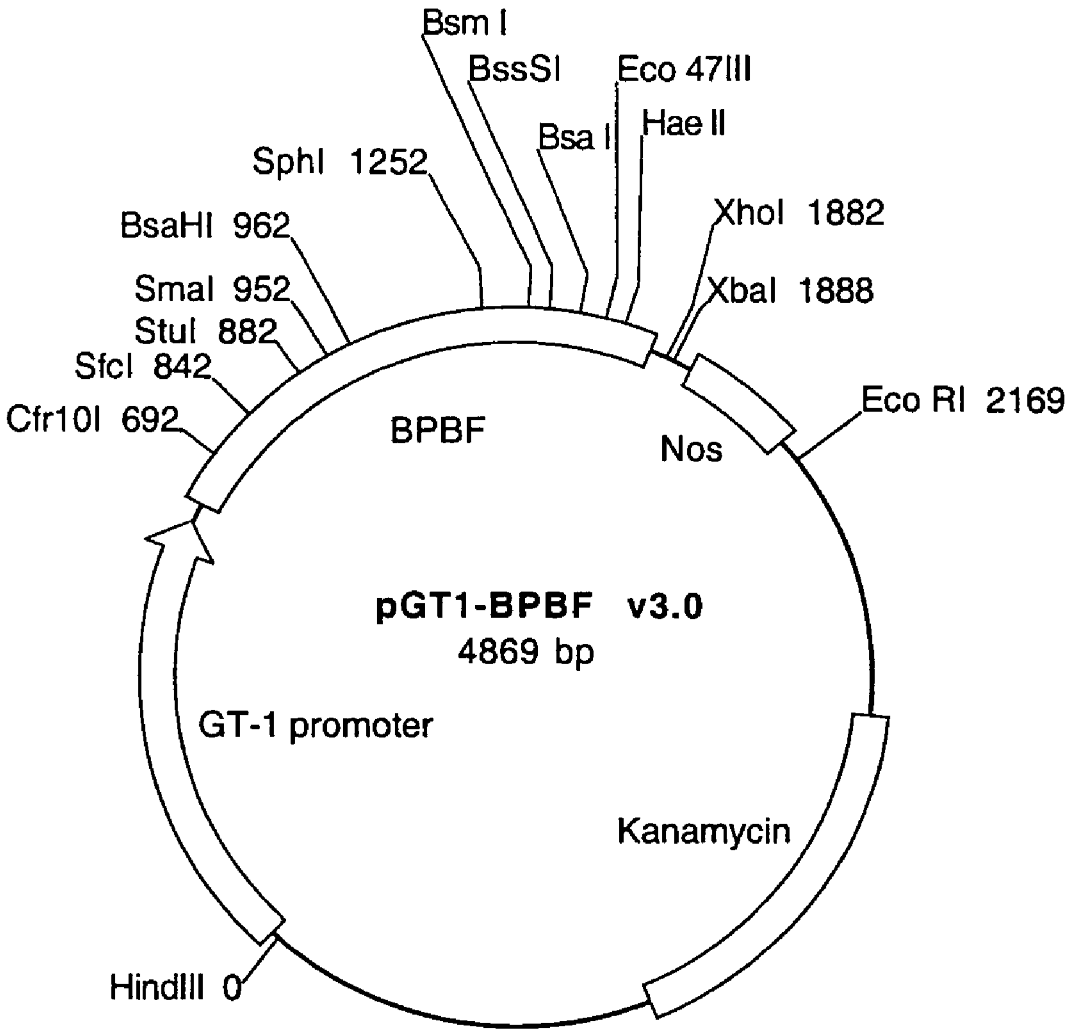
FIGS. 11A-C provide a schematic depiction of the map of 3 plasmids which contain various transcription factor coding sequences under the control of the rice endosperm-specific glutelin promoter (Gt-1), where (A) the plasmid includes the barley prolamin box binding factor protein (BPBF), (B) the plasmid includes the maize prolamin box binding factor protein (PBF) and (C) the plasmid includes the maize opaque2 binding protein (O2).
Figure 11B:
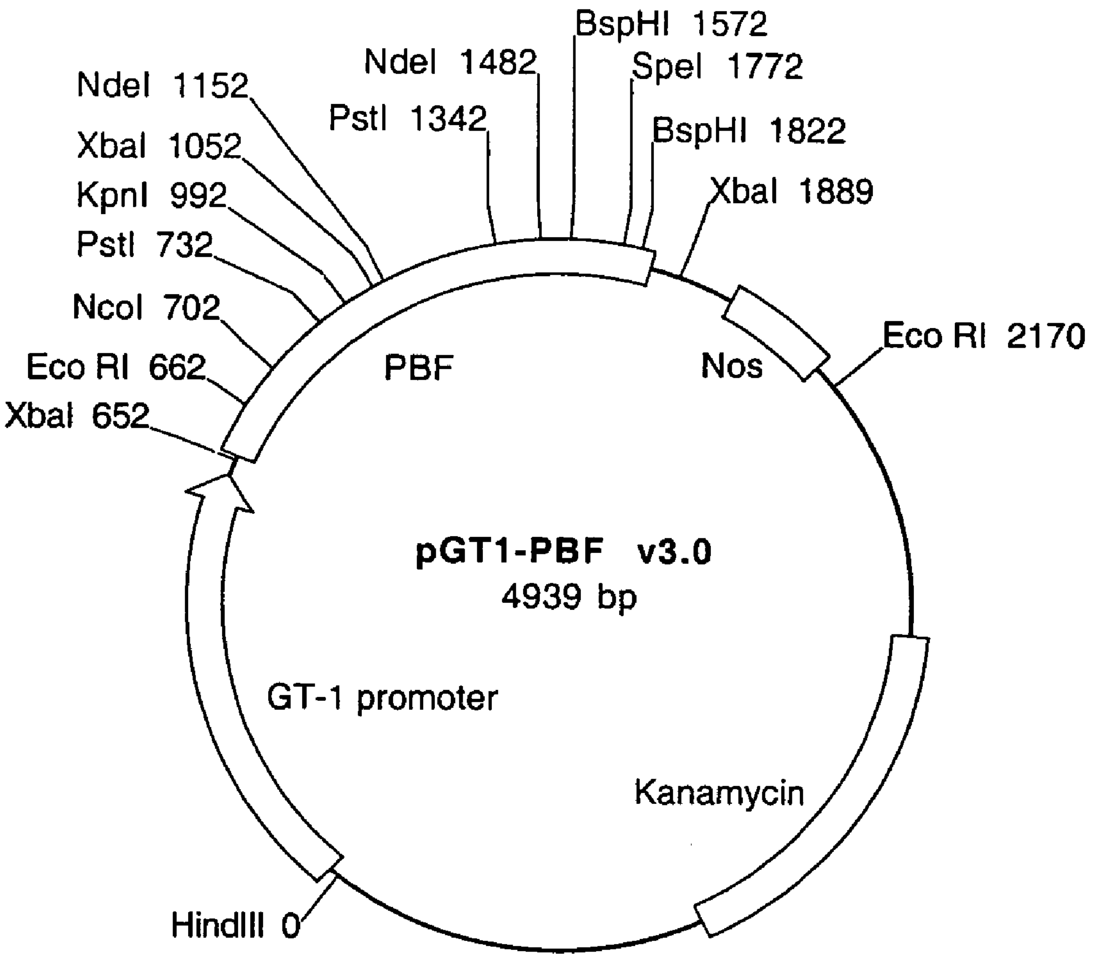
Figure 11C:
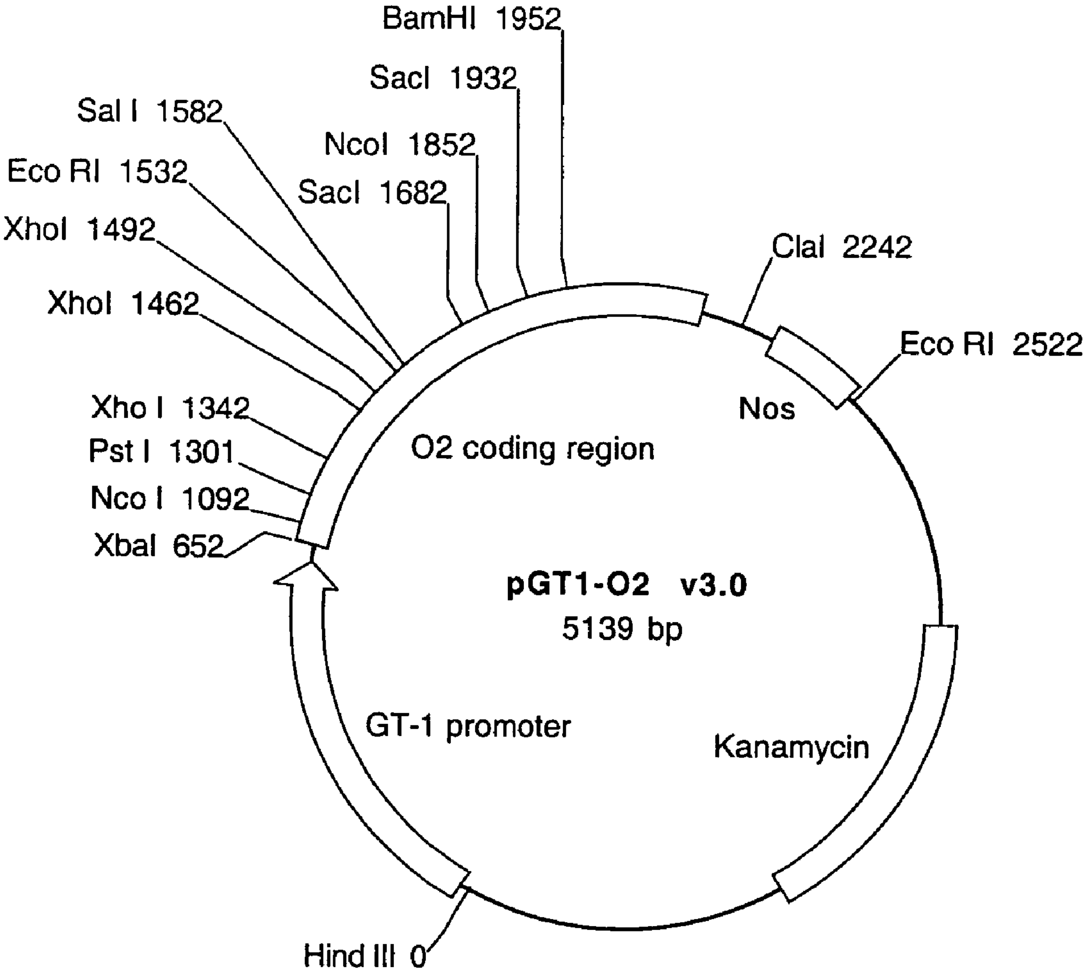

The nucleic acid sequence for the Opaque2 transcription factor found for example at GenBank Accession number X15544 (opaque2 gene), M29411 (opaque2 cDNA) was cloned into an expression vector under the control of the rice glutelin-1 (Gt-1) promoter (FIG. 11C, maize).

The rice PBF and maize PBF coding sequences found for example at GenBank Accession Nos. D11385 (rice cDNA) and ZMU82230 (maize cDNA) were also cloned into an expression vector under the control of the rice glutelin-1 (Gt-1) promoter.

The DNA sequence of the rice (*Oryza sativa*) globulin promoter, ("Glb") with putative binding sites for the O2 transcription factor and the prolamin box and the DNA sequence of the wheat Bx7 promoter with putative binding sites for the O2 transcription factor and the prolamin box are shown in FIGS. 9 and 10, respectively. The coding sequence for the wheat Bx7 gene is presented at GenBank Accession Nos. M22209.

Promoters were digested to produce the appropriate cohesive ends and cloned into compatible sites in a reporter construct. In one example, the reporter construct is comprised of the rice globulin (Glb) or wheat Bx7 promoter translationally fused with GUS, with the resulting constructs designated, Glb/GUS/NOS and Bx7/GUS/NOS (FIG. 12A).

The effect of plant transcription factors on the gene expression was evaluated by co-transformation with a heterologous nucleic acid construct effective to express the transcription factor, e.g. O2, PBF, BPBF or Reb.

Example 2

Transient Expression Assays with the Reb Transcription Factor

A. Plasmid Construction

Plasmids were constructed using standard molecular biological techniques as described in Ausubel et al., 1987. Plasmids API212 (Glb-GUS) carrying the rice globulin gene promoter fused to the GUS reporter gene and API142 (Gt1-GUS) containing the rice glutelin 1 gene promoter fused to the GUS reporter gene were used for transient expression assays. The globulin promoter (GenBank Accession number X63990) and glutelin 1 promoter (GenBank Accession number Y00687) were obtained from M2O2 (*Oryza sativa Japonica* subsp.) by amplification with POR. The plasmid containing the Reb gene under the control of its native promoter was designated pAPI267 (Native-Reb). The plasmid designated Glb-Reb (pAPI266) was prepared by cloning the Reb coding region (NruI/SacI fragment) into the Glb-GUS plasmid after removal of the GUS gene by digestion with SmaI/SacI, thus replacing the GUS gene with the Reb gene. Using the same strategy, the plasmid designated Actin-Reb (pAPI277) was made by replacing the GUS gene of plasmid Act1-D-GUS (McElroy, 1990) with the complete Reb gene (NruI/SacI fragment). The Act1-D promoter was kindly provided by Professor Ray Wu, Cornell University (McElroy, 1990).

B. Transient Assay Using Rice Endosperm

Rice spikelets with immature endosperm (7-9 days after pollination, dap) of M2O2 (*Oryza sativa Japonica* subsp.) were collected from plants grown in the greenhouse at 30° C. The spikelets were sterilized with 70% ethanol for 10 min. After evaporation of residual ethanol, the endosperm was dissected and 10 immature endosperms placed on a filter paper in a Petri dish containing AA medium [Chen et al., 1998] supplemented with 20 mM ammonium nitrate.

Fifty μl of gold particles (60 $mg \cdot ml^{-1}$ at 1:1 ratio of 1.0 and 1.5-3.0 μm diameter gold particle) were coated with 5 μg DNA consisting of a mixture of the reporter gene, the effector gene, and the internal control gene, typically at a molar ratio of 1:1:1. DNA coating was accomplished as described in the instruction manual of the Biolistic PDS system (Bio-RAD, Hercules, Calif., USA). pAHC18 containing the luciferase gene driven by an ubiquitin promoter [Christensen et al., 1996] was used as an internal control. In tests without the effector gene, pAHC18 was replaced by pBluescript DNA. Particle bombardment was carried out with a biolistic Helium gun device at 1100 psi (Biolistic PDS 1000/He system, Bio-Rad, Hercules, Calif., USA). After bombardment, the immature endosperms were incubated at 25° C. for 24 h in 5 ml of AA medium supplemented with 20 mM ammonium nitrate, 50 $\mu g \cdot ml^{-1}$ cefotaxin and 50 $\mu g \cdot ml^{-1}$ timentin (Sigma, Louis, Mo., USA) to prevent bacterial growth. The endosperms were then harvested and ground with 55 μl extraction buffer (0.1 M potassium phosphate, pH 8.0, 1 mM EDTA, 10 mM DDT, 5% glycerol, 0.2 mM leupeptin and 0.2 μM phenylethylsulfonyl fluoride (PMSF). The extract was centrifuged at 25,000 g for 5 min at 4° C. From the supernatant, a 20 μl aliquot was added to 180 μl of luciferase assay buffer (0.25 M Tricine, pH 7.8, 150 mM magnesium chloride, 10 mM ATP, 1 mM DDT and 100 $\mu g\ ml^{-1}$ BSA). Another 20 μl aliquot was added to 200 μl of GUS assay buffer (Tropix, Bedford, Mass., USA). Luciferase activity was measured after incubation at 25° C. for 20 min and β-glucuronidase activity after 1 h at 37° C. for 1 h with a Monolight 2010 chemi-illuminometer according to the manufacturer's instructions (Analytical Luminescence Lab., Monolight, San Diego, Calif., USA). β-glucuronidase activity was normalized to the luciferase activity and expressed relative to the activity of the Glb-GUS. In general, the data presented reflect an average of at least six assays of two independent experiments.

C. Transcriptional Activation with Reb

The function of Reb gene was analyzed by the transient assay with rice immature endosperm. Transient expression studies were carried out to evaluate the effect of Reb on expression of GUS (β-glucuronidase), under the control of the Glb promoter.

The results shown in FIG. 6B indicate that GUS expression was increased when Reb was expressed under the control of the globulin promoter, the actin promoter or the native Reb promoter suggesting that Reb is effective to an activate expression mediated by Glb promoter.

Putative Reb binding sites in the globulin (Glb) promoter were identified as shown in FIG. 4.

In order to determine, if binding of the Reb protein to the motif (GCCACGT(A/C)AG) (SEQ ID NO:36) in the globulin (Glb) gene promoter activates transcription of this promoter, plasmids containing fusions of the Reb coding region with the Glb promoter and the rice actin (Act) gene promoter were prepared (FIG. 6A). These as well as the expression plasmid containing the native Reb gene (pAPI266) were co-bombarded into the rice endosperm with a plasmid containing the GUS reporter gene driven by the Glb gene promoter and an internal control plasmid containing the luciferase gene driven by the ubiquitin promoter.

Setting the level of GUS expression by the globulin gene promoter as 1, the co-delivery of the plasmids containing the Reb gene increased GUS expression irrespective of whether the gene was driven by its own promoter or the Glb promoter or the Actin promoter (FIG. 6B). The increases were 2.43, 2.01 and 1.98 fold, respectively. The activation of GUS expression was abolished when a promoter-less Reb construct was co-bombarded with Glb-GUS (FIG. 6B). These results suggested that the Reb protein functions as a transcriptional activator of the Glb promoter.

D. Identification of the Upstream Activation Sequence (UAS) for Reb

Using a band-shift assay, Nakase et al., 1997 have shown that Reb binds to two motifs, GCCACGTAAG (SEQ ID NO:37) or GCCACGTCAG (SEQ ID NO:38). An analysis of the Glb promoter sequence revealed two copies of GCCACGTAAG (SEQ ID NO:37) and one copy of GCCACGTCAG (SEQ ID NO:38) clustered in the sequence region −700 bp distal to the TATA box of the promoter (FIG. 4).

Figure 7A:
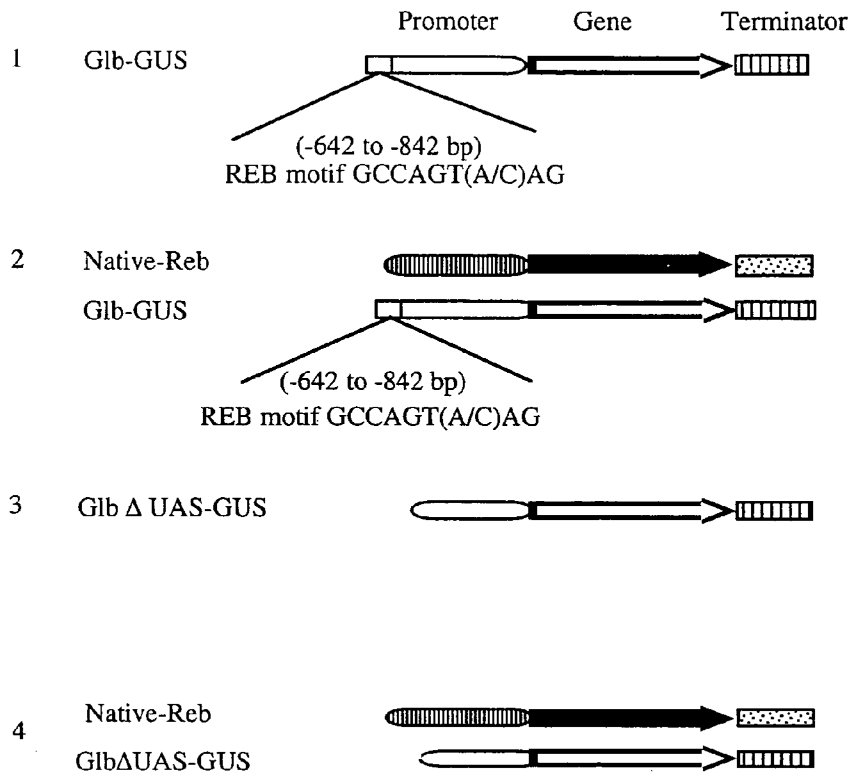
FIG. 7A presents a schematic diagram of the plasmid constructs used for loss-of-function analysis of Reb transactivation measured by a transient assay using: (1) the GUS reporter construct, Glb-GUS-Nos; (2) the Native-Reb-Term construct co-bombarded with the Glb-GUS-Nos reporter construct; (3) the GlbΔUAS-GUS-Nos construct; and (4) the Native-Reb-Term co-bombarded with the Glb reporter construct in which the Reb UAS motifs of the Glb promoter [GCCAGT(A/C) AG] (SEQ ID NO: 41) were deleted.

In order to determine whether the binding motifs for Reb signify an upstream activation sequence (UAS), 200 bp of the Glb promoter, which contains the three motifs located at positions −642 to −842 distal to the TATA box were deleted from the Glb promoter (FIG. 7A). The deletion was demonstrated to have no effect on the expression of GUS as both the Glb-GUS and the GlbΔUAS-GUS (UAS deleted) constructs showed the same level of background GUS expression (FIG. 7B).

Figure 7B:
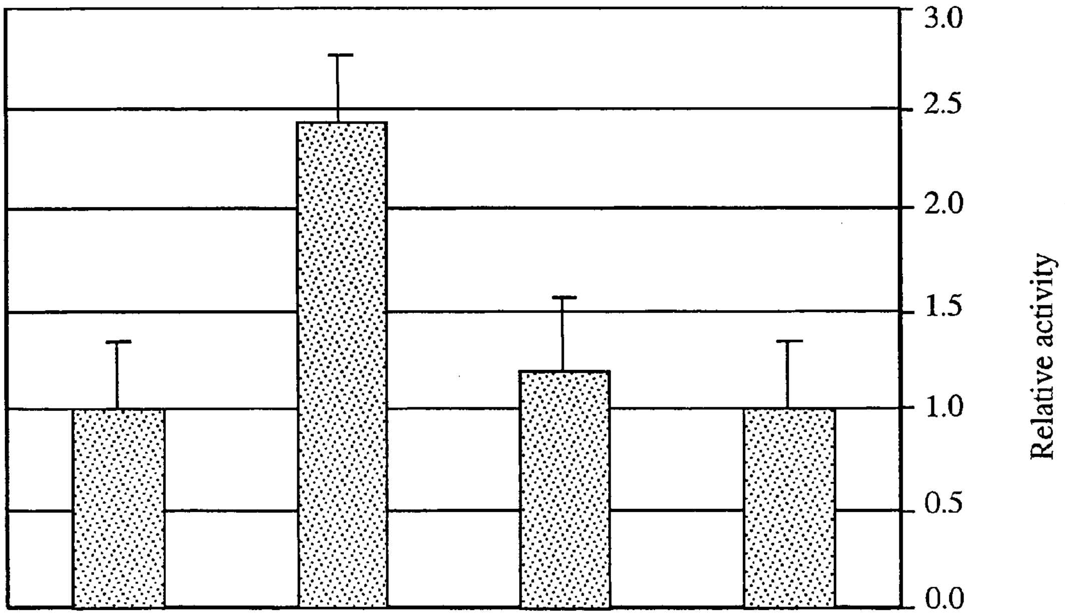
FIG. 7B illustrates the relative GUS activity as measured in transient expression assays using the effector/reporter combinations shown in FIG. 7A.

When Native-Reb was co-bombarded with GlbΔUAS-GUS, the transcriptional activation by Reb which was evident when Native-Reb was co-bombarded with Glb-GUS was lost (FIG. 7B). These data indicate the transcriptional activation of Glb-GUS by Reb occurs through this 200 bp fragment containing Reb binding motifs.

Figure 8A:
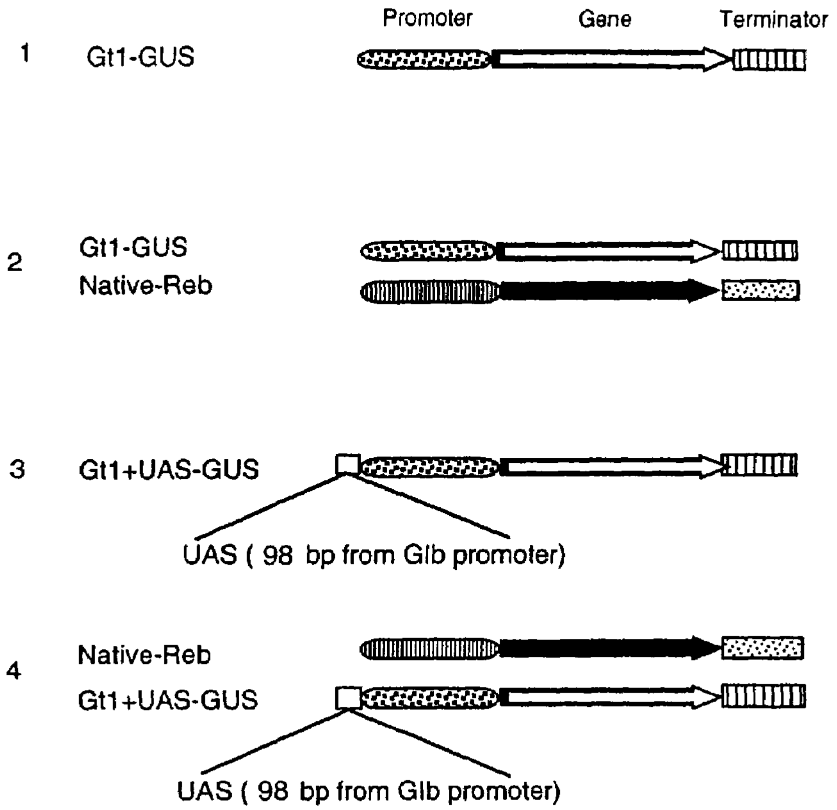
FIG. 8A presents a schematic diagram of the plasmid constructs used for gain-of-function analysis Reb transactivation by transient assay using: (1) a GUS reporter construct with GUS expressed under the control of the Gt1 promoter (Gt1-GUS-Nos); (2) the Gt1-GUS-Nos construct where the cells were co-bombarded with an expression construct which has Reb expressed under the control of the native Reb promoter (native-Reb-Term); (3) a GUS reporter construct with GUS expressed under the control of the Gt1 promoter modified to contain the Reb response sequence, UAS (Gt1-UAS-GUS-Nos); and (4) the modified Gt1-UAS-GUS-Nos reporter construct where the cells were co-bombarded with native-Reb-Term.

A scan of the rice glutelin1 (Gt1) promoter sequence did not reveal the presence of Reb binding motifs. Accordingly, Gt1 was selected as a candidate for the introduction of the UAS from the Glb promoter in order to test for gain of the Reb response function. Heterologous nucleic acid constructs were prepared containing the native Gt1 promoter linked to the GUS gene (Gt1-GUS), and a Gt1 promoter modified to contain a 98 bp Reb UAS fragment containing 3 copies of GCCACGT(C/A)AG (SEQ ID NO:36) (amplified from the G1b promoter) was inserted at position −630 bp distal to the TATA box of the Gt1 promoter in order to generate Gt1+UAS-GUS (FIG. 8A).

Figure 8B:
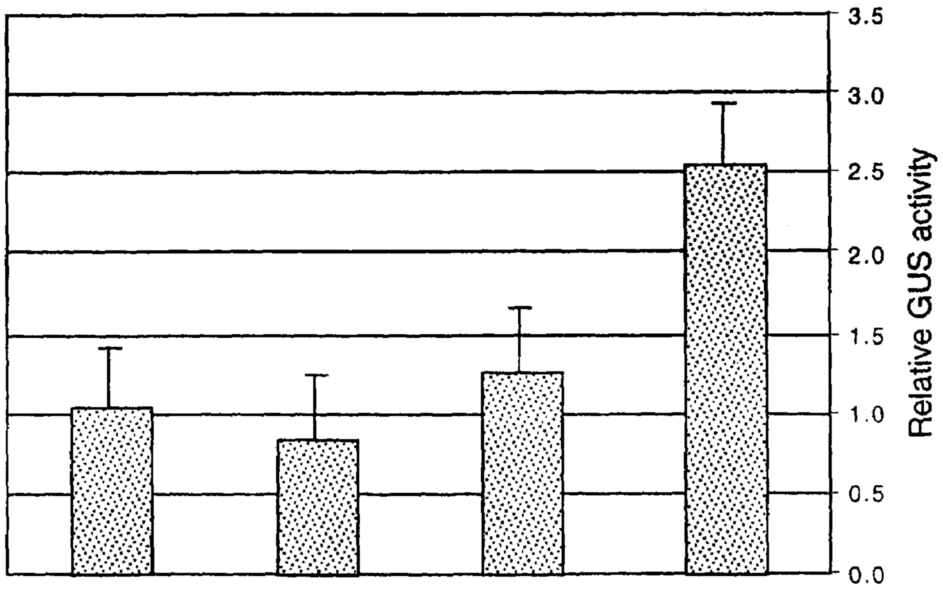
FIG. 8B illustrates the relative GUS activity as measured in transient expression assays using the reporter constructs shown in FIG. 9A.

When Gt1-GUS was tested by co-bombardment of developing endosperm with the native Reb gene and Gt1-GUS, the results showed that Reb does not activate the Gt1 promoter (FIG. 8B). Gt1+UAS-GUS was tested for GUS expression and it was shown that addition of the Reb UAS to the Gt1 promoter did not increase its capacity for GUS expression significantly (FIG. 8B). However, when Gt1+UAS-GUS was tested by co-bombardment of developing endosperm with the native Reb gene a 2.5 fold increase in GUS activity was obtained (FIG. 8B).

The Reb protein was previously described as a transcription factor. The results described herein show that (1) Reb is a transcriptional activator, as evidenced by a 2.0 to 2.5-fold increase in GUS activity when Reb effector constructs were co-transferred with the reporter uid A gene encoding GUS under the control of the Glb promoter into immature rice endosperm cells; (2) Reb specifically activates the Glb promoter but not glutelin gene family promoters; (3) Reb interacts with an approximately 100 bp upstream activation sequence (UAS) containing the motifs GCCACGTCAG (SEQ ID NO:38) and GCCACGTAAG (SEQ ID NO:37) (GCCACGT(A/C)AG) (SEQ ID NO:36) of the Glb promoter, as confirmed by loss-of-function and gain-of-function experiments. The loss of activation function, when the 200 bp fragment containing the Reb UAS is removed from the Glb gene promoter, and the gain of this function, when the 98 bp fragment with Reb UAS is added to the Gt1 promoter, establishes the 98 bp fragment as an upstream activation sequence (UAS).

Example 3

Transient Expression Assays with the O2 and PBF Transcription Factors

A. Plasmid Construction

Plasmids were constructed using standard molecular biological techniques as described in Ausubel et al., 1987. A 693 bp segment of the Gt1 promoter sequence was removed from pGt1 v3.0 SDM, a Gt1 expression vector, and used to replace the CaMV 35S promoter in pBI221 through HindIII and SmaI sites, resulting in Gt1/GUS/NOS. The promoter regions from the rice glutelin genes Gt3, GluB-1 and GluB-2; the rice prolamin genes RP6 and PG5a; the rice globulin gene Glb; and the wheat glutelin gene, Bx7; were PCR amplified from M2O2 genomic DNA or the wheat variety, Anza, for Bx7.

The PCR amplifications were carried out using the GeneAmp PCR system (model 2400, Perkin-Elmer) operated according to the manufacturers instructions. Basic cycling conditions were 30 cycles, after a 2 minute pre-denaturing step at 95° C., with a 30 second denaturing step at 95° C., a 30 second annealing step at specific temperature, and a 2 minute extension step at 72° C. The final extension step was 5 minute at 72° C., followed by 4° C. soaking step. Reaction components per 50 µl volume, were 1 µg of genomic DNA or 1 ng of plasmid DNA, 2.5 µl of 5 µM primer mixture, 5 µl of 10 mM dNTP, 2.5 units of Taq polymerase (Perkin-Elmer), 5 µl of 10×PCR buffer (Perkin-Elmer). The concentration of $MgCl_2$ was 1.5 mM, for all the promoters with the exception of the Bx7 promoter for which 2.5 mM $MgCl_2$ was used. All the PCR primers and amplified fragment sizes are presented in Table 1.

Each of the PCR amplified promoter sequences was cloned into the GUS cassette of pBI221 through PstI and XbaI sites to give Gt3/GUS/NOS, GluB-1/GUS/NOS, GluB-2/GUS/NOS, RP6/GUS/NOS, PG5a/GUS/NOS, Glb/GUS/NOS, Bx7/GUS/NOS, for the Gt3, GluB-1, GluB-2, PG5a, RP6, Glb and Bx7 promoters, respectively.

TABLE 1

Primer sequence used to amplify promoter fragment

| Primers | Primer sequences | PCR amplified fragment (bp) | Annealing temperature |
|---|---|---|---|
| Gt3/fw | GTTAGTcTGCAgTGTAAGTGTAGCTTC (SEQ ID NO:3) | 856 | 58° C. |
| Gt3/rv | ATGGTTGtCtaGaTTTTGTGGGACTGAAC (SEQ ID NO:4) | | |
| GluB-1/fw2 | ACAGACAGcTGcAGAGATATGGATTTTCTAAG (SEQ ID NO:5) | 1319 | 62° C. |
| GluB-1/rv2 | GGAACTCtCtAgAGCTATTTGTACTTGCTTATG (SEQ ID NO:6) | | |
| GluB-2/fw | TCCGAGctgcAGTAATGGATACCTAGT (SEQ ID NO:7) | 1028 | 58° C. |
| GluB-2/rv | GTAGTTtCtAgAGCTATTAGCAGTTGC (SEQ ID NO:8) | | |
| PG5a/fw2 | CGGTGcTGcAGATGGGTTGGGAACCCT (SEQ ID NO:9) | 874 | 58° C. |
| PG5a/rv2 | ATGATCTagATTGCTCTGGGACATAGAT (SEQ ID NO:10) | | |
| RP6/fw | AATTCCTgCagCATCGGCTTAGGTGTA (SEQ ID NO:11) | 684 | 58° C. |
| RP6/rv | TGATCTagATTGTTGTTGGATTCTACT (SEQ ID NO:12) | | |
| Osglb/fw2 | GGCGCCTGcAGGGAGGAGAGGGGAGAGAT (SEQ ID NO:13) | 997 | 58° C. |
| OSglb/rv | ACCTTGCTctagATTGATGATCAATCAGA (SEQ ID NO:14) | | |
| Bx7/fw2 | CGTCGTCTcTGcAGGCCAGGGAAAGACAATG (SEQ ID NO:15) | 993 | 62° C. |
| Bx7/rv | CGCTTAtCtAgaTCAGTGAACTGTCAGTG (SEQ ID NO:16) | | |

All transcription factor ("effector") plasmids where the coding sequences were placed under the control of the CaMV 35S promoter were generated by subcloning cDNA fragments of either O2, o2676 or PBF downstream of the CaMV 35S promoter and the Adh1 intron and upstream of the nos 3' end in pMF6. For O2, the BglII O2Δ1 cassette described by Schmidt et al., 1992 (which removes the start codons for the three small ORFs present in the 5' leader sequence, thus promoting increased O2 expression), was inserted into the BamHI site of pMF6. The o2676 effector was generated as described for O2 except that an internal restriction fragment containing the o2676 point mutation (Aukerman, 1991) was substituted for the corresponding restriction fragment in BglII O2Δ1 cassette. For PBF, a BamHI-XhoI fragment containing the entire PBF cDNA (VicenteCarbajosa, 1997) was subcloned into the same sites of pMF6. O2Δ1 and PBF were also expressed under the control of the maize UBI1 promoter and first intron by subcloning the respective cDNA clones into the BamHI site of the pAHC17 plasmid (Christensen et al., 1996).

FIGS. 11A-C are a schematic depiction of plasmids containing the (A) barley prolamin box binding factor protein (BPBF), (B) maize prolamin box binding factor protein (PBF) and (C) the maize opaque2 binding protein (O2) transcription factor coding sequences under the control of the rice endosperm-specific glutelin promoter (Gt-1).

The construction of antisense plasmids for the O2 and PBF DNA binding domains was carried out using PCR primers designed to amplify the highly conserved region of DNA binding domains of O2 and PBF. The PCR primer sets for O2 were (MO2/fw: 5'-TTCTGGGATCCAAGATGCCTACCGAGG-3' (SEQ ID NO:17) and MO2/rv: 5'-GGGGTCGGATCCGAGATGGGCATGGAC-3' (SEQ ID NO:18), and for PBF (PBF/fw: 5'-AGTGGGGATCCTAAGCCGAGGCCGCAAC-3' (SEQ ID NO:19) and PBF/rv: 5'-GCTAGGGGATCCTGGTGCATAGGTAGCA-3' (SEQ ID NO:20), resulting in amplification of 333 bp and 278 bp amplification fragments, respectively when Ubi:O2 and Ubi:PBF were used as the template.

The PCR reactions were performed in 50 μl of 1×PCR reaction buffer (50 mM KCl, 10 mM Tris-HCl, pH 9.0, and 0.1% Triton X-100) containing 250 μM dNTP, 1 ng of template, 0.1 μM of each of forward and reverse primers, and 0.3 unit of Taq polymerase (Perkin-Elmer). The GeneAmp PCR system (model 2400, Perkin-Elmer) was programmed for an initial denaturing temperature of 94° C. for 4 min, a 30 sec denaturing temperature of 94° C., an annealing temperature of 58° C. for 30 sec, and an extension temperature of 72° C. for 2 min. The reaction was carried out for 30 cycles. An additional extension at 72° C. followed for 5 min was allowed to proceed after completion of the final cycle. The PCR products were purified by phenol:chloroform:isoamyl alcohol extraction procedure and precipitated with 100% ethanol. After resuspending in 50 μl of dH20, the amplified products were digested with BamHI. The BamHI flanked PCR products were used to replace the luciferase coding region of pAHC18 [Christensen et al., 1996].

Insertion of the PCR-amplified DNA binding domain of O2 and PBF in antisense orientation into the expression cassette containing the ubiquitin promoter was completed by PCR using the primer sets MO2/rv and NOS/rv; 5'-CGGCAACAGGATTCAATCT-3' (SEQ ID NO:21), PBF/rv and NOS/rv. The PCR was performed under the conditions described above, with the exception that the annealing temperature was changed to 53° C.

B. Transient Assay Using Rice Endosperm

DNA coated gold particles were prepared by mixing 50 μl of gold suspension (60 mg/ml), 50 μl of $CaCl_2$, 2.5 M and 20 μl of spermidine, 0.1 M. In all cases, 5 μg of the GUS chimeric construct and 5 μg of pAHC18 (containing the luciferase gene under the control of the ubiquitin promoter), were used. For co-transfection with effector plasmids, effector plasmids were additionally added in the amount indicated. The total amount of plasmids used for coating gold particles remained constant by adding the pBluescriptII KS (+) or the PMF plasmid (containing the CaMV 35S promoter driving an expression cassette which lacks a coding region). After vortexing for 1 min, the gold particles were washed with 100% ethanol twice and finally resuspended in 50 μl of 100% ethanol. 10 μl of gold particle suspension was loaded into a macrocarrier for bombardment.

Rice immature seeds at 7 to 9 DAP (days after pollination) were harvested and sterilized with husk by incubating 10 minutes in 70% ethanol and followed by spraying with 100% ethanol. After the ethanol evaporated completely, transient assay incubation buffer (TAIB: complete AA medium [Thompson, 1986] supplemented with $NH_4NO_3$ 1.4 g/L, 100 μg/ml of cefotaxime and 100 μg/ml of timentin) was added to prevent seeds from drying out. A portion of each seed grain which contains the embryo (about one fifth) was cut off using a sharp blade and the immature endosperm was squeezed out. About 10 rice immature endosperms were placed in the center of a 3 MM Whatman filter paper, prewetted with TAIB. Particle bombardment was carried out using the biolistic helium gun device (Dupont PSD-1000), as described Hwang et al., 1998. After bombardment, the bombarded immature endosperms were incubated in 5 ml of TAIB in the dark at 25° C. for 1 day.

After incubation, immature endosperms were transferred to a conical Eppendorf tube and homogenized in 55 μl of extraction buffer ($KH_2PO_4$, 0.1 M, EDTA, 1 mM and β-mercaptoethanol, 7 mM) by a disposable plastic pestle. After spinning down the cell debris by centrifuging at 15,000 rpm for 15 min, 20 μl of supernatant was used in an assay for GUS or luciferase enzyme activity [deWet, 1987; Bronstein, 1994].

C. Transcriptional Activation with O2 and PBF

Transient expression assays were carried out to evaluate the effector activity of the O2 and PBF transcription factors on GUS expression.

Rice immature endosperms were isolated from caryopses at 7-9 DAP (DAP:Days After Pollination). The amount of each effector plasmid used is indicated in the individual examples, below. The total amount of plasmid for coating the gold particles remained constant by adding pBluescriptII KS(+). To normalize transfection efficiency, in every experiment, a luciferase gene under the control of the maize ubiquitin promoter was co-transfected (with 5 μg of pAHC18 (Ubi/LUC/NOS) used as an internal control for all experiments). Following measurements of GUS and LUX activity, the GUS expression level was normalized by dividing by the LUX activity from luciferase to obtain the GUS/LUX ratio. Therefore, the GUS/LUX ratio quantitatively indicates the transcriptional activity from the promoter of the heterologous reporter gene.

Developing rice endosperms at 7-9 DAP were biolistically bombarded with various heterologous nucleic acid constructs to examine the ability of the maize trans acting factor genes encoding opaque 2 (O2) and prolamin box binding factor (PBF) to effect expression of heterologous nucleic acid constructs under the control of the promoter regions from the rice glutelin genes Gt3, GluB-1 and GluB-2; the rice prolamin genes RP6 and PG5a; the rice globulin gene Glb; and the wheat glutelin gene, Bx7. O2 and PBF were expressed under the control of the Ubi promoter in the Ubi:O2 and Ubi:PBF constructs, respectively.

As shown in FIG. 13B, co-transfection of the Gt1 reporter plasmid (Gt1/GUS/NOS) with 35S:O2 and 35S:PBF resulted in approximately a 5 and 3-fold in transcription activity, respectively, relative to the activity from the Gt1 reporter plasmid alone (FIG. 13B).

When immature endosperms were co-bombarded with an equimolar mixture of the 35S:O2 and 35S:PBF constructs, GUS expression from Gt1/GUS/NOS increased up to 6-fold (FIG. 14B). Transient assays using effector plasmids expressing mutant forms of the O2 and PBF transcription factors demonstrated that the observed activation is a consequence of direct interaction between O2 and PBF and the Gt1 promoter. The relative GUS/LUX ratio from the Gt1 reporter plasmid was not affected by co-bombardment with effector plasmids expressing defective forms of the O2 and PBF proteins (FIG. 14B) indicating that the capability of O2 and PBF to bind their specific target sites is critical for transactivation of the Gt1 promoter.

FIG. 13B illustrates transactivation of the Gt1 promoter by various amounts of O2 and PBF effector plasmids in rice immature endosperms. As shown in FIG. 13B, Ubi:O2 and Ubi:PBF at the amount of 1 μg were able to transactivate the Gt1 promoter, approximately 4 and 3 fold, respectively. This transactivation effect increased along with the increase in the amount of effector up to approximately 5 μg. The increase in promoter activity by O2 and PBF together was shown to be additive, independent of the amount of plasmid combined (FIG. 13B).

As described above, in addition to the promoter of rice glutelin gene (Gt1), several other promoters of genes encoding different kinds of seed storage proteins like rice globulin, rice prolamin and wheat glutenin were tested for their responsiveness to O2 and PBF (FIG. 12A). The transcription activity from the promoter of rice globulin, Glb was increased by about 3 and 4 fold, in the presence of O2 and PBF, respectively (FIG. 12B). Bx7, the glutelin promoter from wheat, was shown to be transactivated in rice immature endosperms by co-bombardment with O2 and PBF up to about 1.8 fold, respectively (FIG. 12B). The O2 and PBF effectors were also shown to transactivate the rice prolamin gene promoters, RP6 about 5 and 3.5 fold, and PG5a, about 2 and 1.5 fold, respectively (FIG. 12B).

The effect of O2 and PBF on the promoters from different kinds of rice storage genes including Gt1, Gt3, GluB-1 and GluB-2; the rice prolamin genes RP6 and PG5a; the rice globulin gene Glb and the wheat glutelin gene, Bx7 was tested. Table 2 shows the responsiveness of the promoters to O2 and PBF, with an additive increase in transactivation observed by co-transfection with both effector plasmids. Of the promoters tested, the Gt1 promoter was the most responsive to both of O2 and PBF and co-transfection with both plasmids gave about a 15 fold increase in GUS activity. The additive increase in promoter activity by co-bombardment of both effector plasmids was observed in all the promoters of storage protein genes that were tested. The rice actin promoter was much less responsiveness to O2 and PBF effectors and the promoter activity of the CaMV 35S promoter was not affected by co-transfection with O2 and PBF effector plasmids (Table 2).

TABLE 2

GUS expression in rice immature endosperms in response to O2 and PBF.

| Effector | O2[1] | PBF[1] | O2/PBF[1] |
|---|---|---|---|
| Gt1 | 10.8(2.14) | 4.57(1.55) | 14.6(1.08) |
| Glb | 3.22(0.72) | 4.42(0.85) | 8.55(2.27) |

TABLE 2-continued

GUS expression in rice immature endosperms in response to O2 and PBF.

| Effector | O2[1] | PBF[1] | O2/PBF[1] |
|---|---|---|---|
| RP6 | 5.22(1.45) | 3.36(0.71) | 8.20(1.18) |
| Bx7 | 1.78(0.13) | 1.84(0.38) | 3.81(1.03) |
| PG5a | 2.13(0.42) | 1.59(0.18) | 3.14(0.60) |
| Actin | 1.59(0.25) | 1.14(0.21) | 1.64(0.48) |
| CaMV 35S | 1.18(0.04) | 1.06(0.18) | 1.34(0.12) |

[1]fold activation was calculated by normalizing the GUS/LUX ratio from rice endosperms co-bombarded with each effector and a reporter construct to the GUS/LUX ratio of that effector alone. For example, for GT1, all results are given relative to the GUS/LUX ratio of Gt1/GUS/NOS construct. S.D. indicates the standard deviation of a mean value for at least five independent particle bombardments.

[1]fold activation was calculated by normalizing the GUS/LUX ratio from rice endosperms co-bombarded with each effector and a reporter construct to the GUS/LUX ratio of that effector alone. For example, for GT1, all results are given relative to the GUS/LUX ratio of Gt1/GUS/NOS construct. S.D. indicates the standard deviation of a mean value for at least five independent particle bombardments.

[1]Results are presented as "fold activation(SD)", calculated by normalizing the GUS/LUX ratio from rice endosperms co-bombarded with each effector and a reporter construct to the GUS/LUX ratio of that effector alone. For example, for GT1, all results are given relative to the GUS/LUX ratio of Gt1/GUS/NOS construct. S.D. indicates the standard deviation of a mean value for at least five independent particle bombardments.

Example 4

Generation of Transgenic Plants which Express Plant Transcription Factors

Figure 15A:
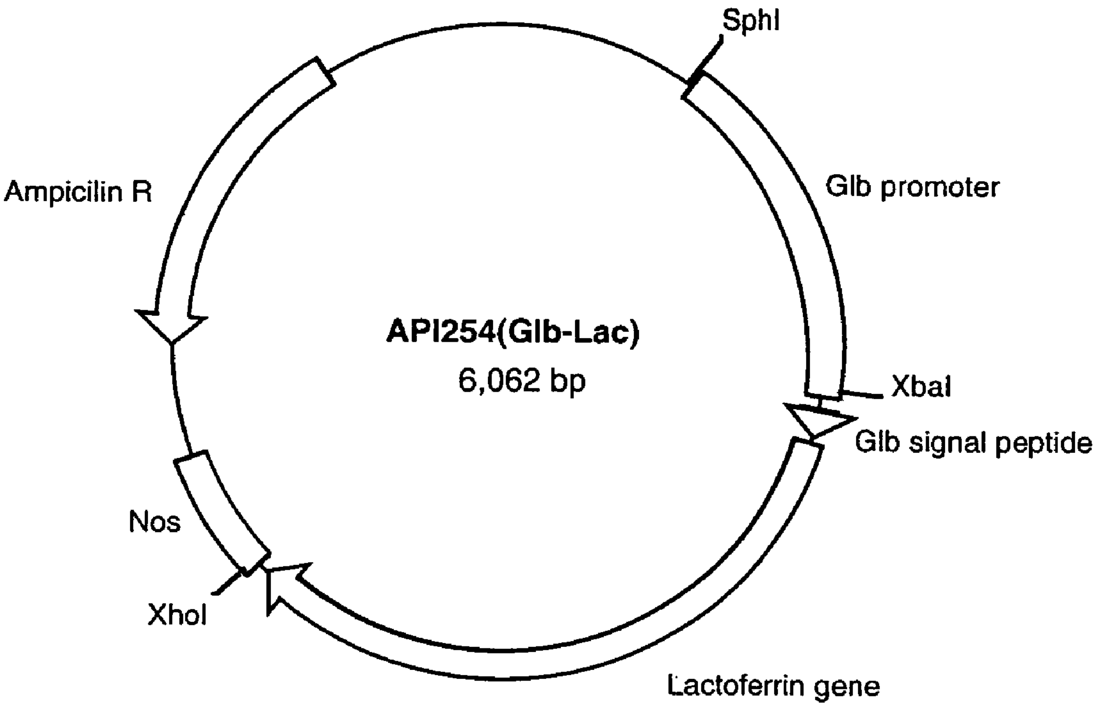
FIGS. 15A and B provide a schematic depiction of the map of 2 plasmids comprising heterologous protein coding sequences under the control of the rice endosperm-specific globulin promoter (Glb), including the Glb signal peptide, where (A) contains the lactoferrin coding sequence, and (B) contains the human lysozyme coding sequence.
Figure 15B:
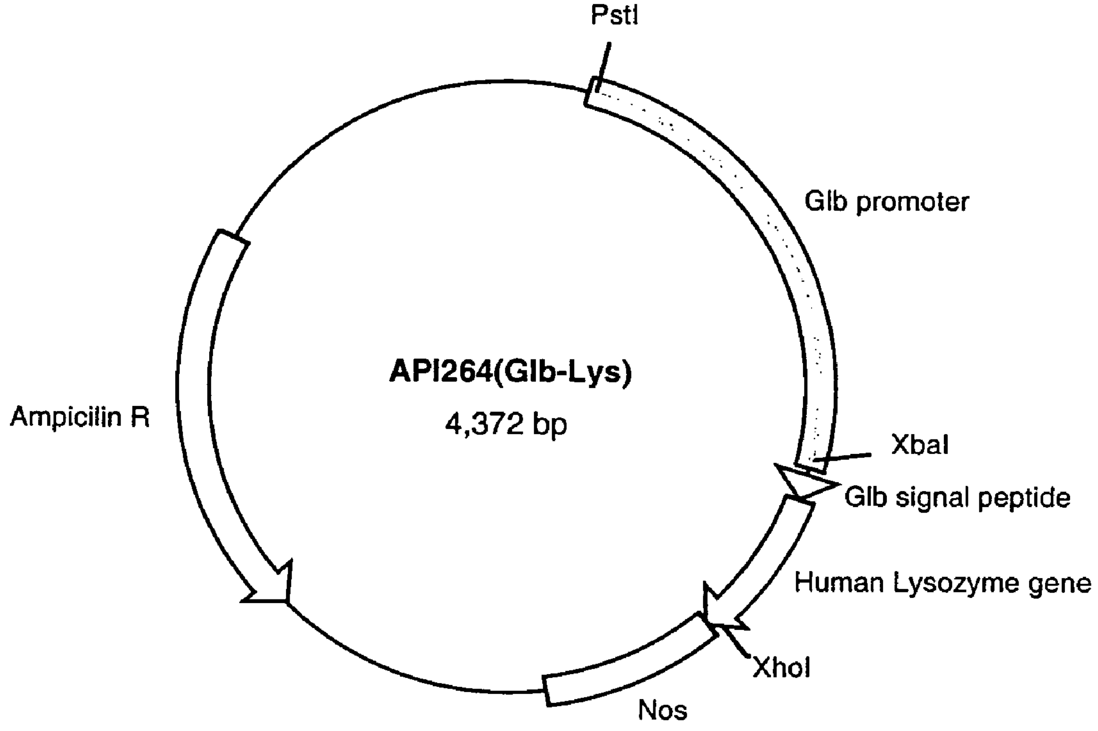

Heterologous nucleic acid constructs were prepared for generation of stable transgenic plant lines. FIGS. 15A and B present a schematic depiction of exemplary plasmids for use in generating such stable transgenic plants. The plasmids contain a heterologous protein coding sequence for lactoferrin and lysozyme under the control of the rice endosperm-specific globulin promoter (Glb), as shown in FIG. 15A and FIG. 15B, respectively.

A. Vector Constructs

A gene encoding the mature polypeptide of human lysozyme (EC 3.2.1.17) with a G+C content of 68.4% was synthesized (Operon, Alameda, Calif., USA) based on the sequence of GenBank Accession number J03801. The DNA was digested with DraI/XhoI, and ligated into the NaeI/XhoI sites of the expression cassette in plasmid API241 which contains the rice globulin gene promoter and signal peptide (GenBank Accession Number X63990). The resulting plasmid was named pAPI264.

B. Development of Stable Transformants and Transgenic Plants

Microprojectile-mediated transformation of rice was carried out based on the procedure described in [Chen, 1998]. Calli were derived from the hypocotyls of germinating mature seeds of the cultivar TP309 (*Oryza sativa*, subspec. *Japonica*). Calli with a diameter of 2-4 mm were selected and placed on a N6 medium (Sigma, Louis, Mo., USA) supplemented with 0.3M mannitol and 0.3M sorbitol for about 20 hours before bombardment. Bombardment was carried out with the biolistic PDC-1000/He instrument (Bio-Rad, Hercules, Calif., USA). Fifty μl of gold particles (60 mg·ml$^{-1}$ at 1:1 ratio of 1.0 and 1.5-3.0 μm diameter gold particle) were coated with effector DNA, target DNA and selection marker DNA in a ratio of 3:3:1 (w/w) and accelerated with a helium pressure of 1100 psi. After two day's incubation, calli were transferred to N6 selection media containing 35 mg·$l^{-1}$ hygromycin B and allowed to grow in the dark at 26° C. for 45 days. Calli resistant to hygromycin B were transferred to regeneration media and used to generate plantlets as described in [Chen, 1998]. After shoots had reached a height of 1-3 cm, the plantlets were transferred to rooting media (MS plus 0.05 mg·$l^{-1}$ α-Naphthaleneactic acid, Sigma, Louis, Mo., USA) and two weeks later the plantlets were transferred to soil and grown in the greenhouse to maturity.

C. PCR Analysis of Transgenic Plants

Figure 16A:
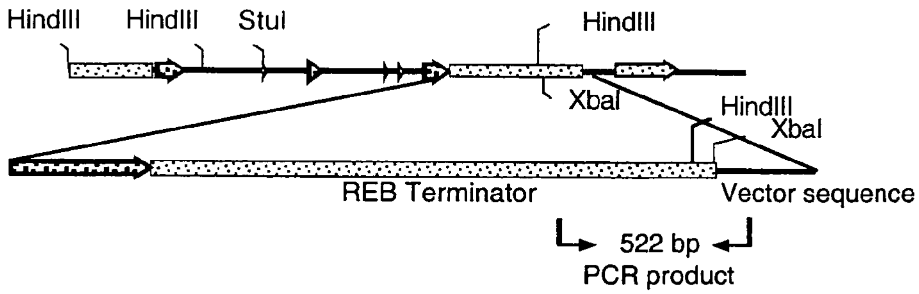
FIGS. 16A-16C depict the results of a POR analysis of $T_0$ transgenic plants containing Reb and the human lysozyme gene.
Figure 16B:
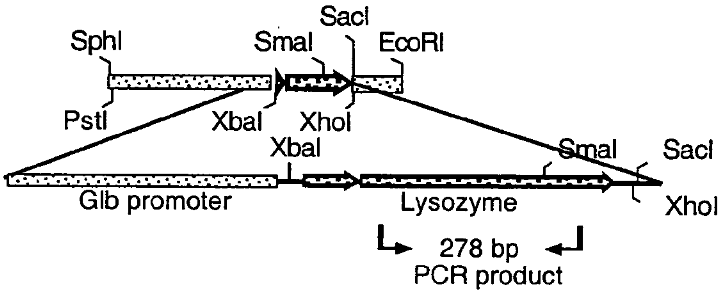
Figure 16C:
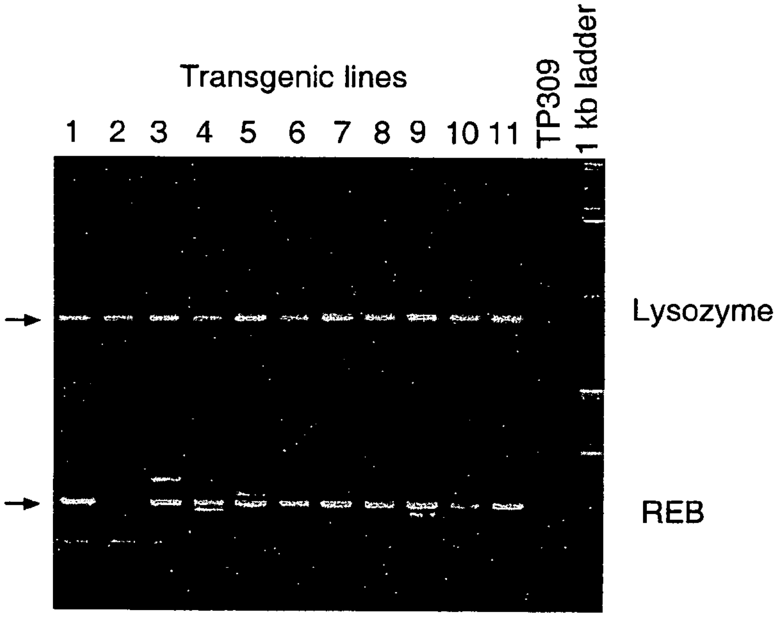

Genomic DNA was prepared from samples of transgenic plant leaves as described in [Dellaporta, 1983 59] and used as the template for amplification with two pairs of primers for the identification of transgenes. For the rice Reb gene, the forward primer 5'-CCATCCAATCCAATCCACTCCAAC-3' (FIG. 16A; SEQ ID NO:22) was designed based on a 3' untranslated terminal sequence of the gene, and the reverse primer was designed based on the vector sequence 5'-AGGCGATTAAGTTGGGTAACG-3' (FIG. 16A, SEQ ID NO:23). For the human lysozyme transgene, the forward primer was designed based on the 5' end of the open reading frame of the gene 5'-CCTAGCCAAAGTCTT CGAGCGGTG-3' (FIG. 16B; SEQ ID NO:24), and the reverse primer was designed based on the 3' end of the open reading frame of the gene 5'-GCGATGTTGTCTTGCAGC-3' (FIG. 16B; SEQ ID NO:25). The PCR mixture contained 100 ng genomic DNA, 10 mM Tris (pH 8.3), 1.5 mM $MgCl_2$, 50 mM KCl, and 0.5 μM dNTP. Amplification employed a program of denaturing at 94° C. for 5 min followed by 30 cycles of 94° C. for 30 seconds, 60° C. for 30 seconds and 72° C. for 45 seconds. The PCR products were resolved by electrophoresis in a 1.2% agarose gel.

D. Lysozyme Activity Assay

A lysozyme assay was carried out using a procedure where twenty individual seeds from each T1 transgenic plant were ground in 1 ml of pre-cold extraction buffer (PBS plus 0.35 M NaCl). After centrifugation at 25,000 g for 5 min at 4° C., the supernatant was recovered. A series of dilutions were made and an aliquot was added to a 96-well microtiter plate containing 250 μl of 0.015% *Micrococcus letus* cells in each well (Sigma, Louis, Mo., USA; procedure developed at Applied Phytologics Inc.). Human lysozyme (EC 3.2.1.17, Sigma, Louis, Mo., USA) was used as the standard and lysozyme activity was measured based on the decrease in turbidity, evaluated using a Microplate Reader 3550 (Bio-Rad, Hercules, Calif., USA). The lysozyme concentration in the samples was determined based on absorbance values of samples relative to a standard curve prepared using different concentrations of human lysozyme. The lysozyme expression level in a given transgenic plant was calculated as the average lysozyme content of the twenty seeds taken from that plant. Total soluble protein in seed extracts was estimated using the Bradford protein assay (Bio-Rad, Hercules, Calif., USA).

Figure 17:
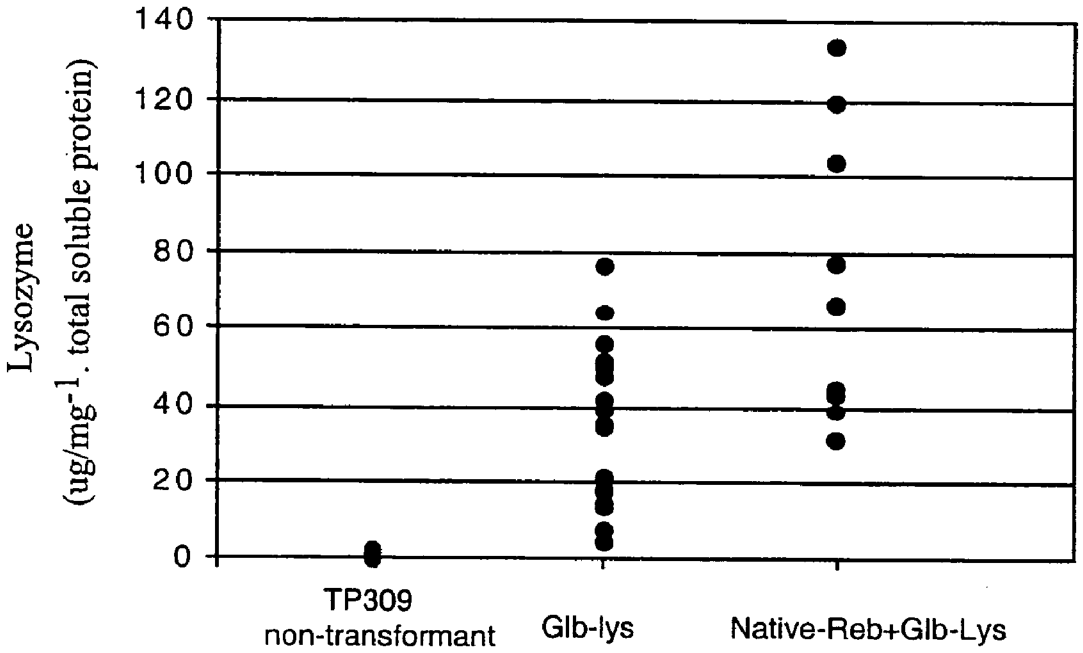
FIG. 17 illustrates the results of an analysis for the expression of human lysozyme in mature seed of $T_0$ transgenic plants derived from progenitor cells transformed with constructs containing the human lysozyme gene expressed under the control of the Glb promoter and the Reb gene expressed under the control of its own promoter. Seeds of ten plants containing the Reb and lysozyme genes and seeds from 17 plants containing only the lysozyme gene were analyzed for lysozyme, with twenty individual seeds analyzed from each plant.

E. Enhanced Human Lysozyme Expression in Transgenic Rice Seed Co-Transformed with Reb In order to evaluate the ability of Reb to increase the expression of a transgene in transgenic plants, plants cells were co-transformed with heterologous nucleic acid constructs comprising the human lysozyme gene driven by the Glb promoter (Glb-lys) and the Reb gene driven by the actin promoter (Act-Reb) and with the Act-Reb construct alone. Normal plant phenotypes were obtained among transformants containing both Glb-lys and native Reb and PCR analysis confirmed that both genes had integrated into the genome in 10 out of 11 plants (FIG. 17). Transgenic seeds were harvested at maturity and lysozyme activity was analyzed.

Lysozyme expression in seeds of the 10 transgenic plants containing native-Reb and Glb-lys ranged from 31-133 μg·$mg^{-1}$ soluble protein with an average of 69.8±11.6 μg·$mg^{-1}$ soluble protein (FIG. 17). Seeds taken from seventeen transgenic plants containing Glb-Lys alone expressed lysozyme in amounts ranging from 7 to 76 μg·$mg^{-1}$ soluble protein with an average of 33.95±4.96 μg·$mg^{-1}$ soluble protein (FIG. 17). No lysozyme activity was detected in untransformed rice seeds (FIG. 17). The results showed that the expression level of the lysozyme increased on an average 2-fold, when the seeds were transgenic for both the Reb gene and Glb-lys. The statistical analysis (t-test) showed that the amount of lysozyme in seeds from the plants transgenic for the Reb gene and Glb-lys is significantly higher than in the plants with Glb-lys alone (P<0.001).

TABLE 3

Brief Description of the Sequences.

| Description | SEQ ID NO |
|---|---|
| forward PCR primer for REB BAC DNA: 5'-CTGATATGTGCCCATGTTCCAAAC-3' | 1 |
| reverse PCR primer for REB BAC DNA: 5'-CCTTGCTGAATGCAGATGTTTCAC-3' | 2 |
| Gt3/fw primer: GTTAGTcTGCAgTGTAAGTGTAGCTTC | 3 |
| Gt3/rv primer: ATGGTTGtCtaGaTTTTGTGGGACTGAAC | 4 |
| GluB-1/fw2 primer: ACAGACAGcTGcAGAGATATGGATTTTCTAAG | 5 |
| GluB-1/rv2 primer: GGAACTCTCtAgAGCTATTTGTACTTGCTTATG | 6 |
| GluB-2/fw primer: TCCGAGctgcAGTAATGGATACCTAGT | 7 |
| GluB-2/rv primer: GTAGTTtCtAgAGCTATTAGCAGTTGC | 8 |
| PG5a/fw2 primer: CGGTGcTGcAGATGGGTTGGGAACCCT | 9 |
| PG5a/rv2 primer: ATGATCTagATTGCTCTGGGACATAGAT | 10 |
| RP6/fw primer: AATTCCTgCagCATCGGCTTAGGTGTA | 11 |

TABLE 3-continued

Brief Description of the Sequences.

| Description | SEQ ID NO |
|---|---|
| RP6/rv primer: TGATCTagATTGTTGTTGGATTCTACT | 12 |
| Osglb/fw2 primer: GGCGCCTGcAGGGAGGAGAGGGGAGAGAT | 13 |
| OSglb/rv primer: ACCTTGCTctagATTGATGATCAATCAGA | 14 |
| Bx7/fw2 primer: CGTCGTCTcTGcAGGCCAGGGAAAGACAATG | 15 |
| Bx7/rv2 primer: CGCTTAtCtAgaTCAGTGAACTGTCAGTG | 16 |
| forward PCR primer for O2 DNA<br>MO2/fw: 5'-TTCTGGGATCCAAGATGCCTACCGAGG-3' | 17 |
| reverse PCR primer for O2 DNA<br>MO2/rv: 5'-GGGGTCGGATCCGAGATGGGCATGGAC-3' | 18 |
| forward PCR primer for PBF DNA<br>PBF (PBF/fw: 5'-AGTGGGGATCCTAAGCCGAGGCCGCAAC-3' | 19 |
| reverse PCR primer for PBF DNA<br>PBF/rv: 5'-GCTAGGGGATCCTGGTGCATAGGTAGCA-3' | 20 |
| NOS/rv PCR primer<br>CGGCAACAGGATTCAATCT | 21 |
| forward primer for REB analysis (FIG. 18A)<br>5'-CCATCCAATCCAATCCACTCCAAC-3' | 22 |
| reverse primer for REB analysis (FIG. 18A)<br>5'-AGGCGATTAAGTTGGGTAACG-3' | 23 |
| forward primer for human lysozyme analysis (FIG. 18B)<br>5'-CCTAGCCAAAGTCTT CGAGCGGTG-3' | 24 |
| reverse primer for human lysozyme analysis (FIG. 18B)<br>5'-GCGATGTTGTCTTGCAGC-3' | 25 |
| *Oryza sativa glutelin* 1 (Gtl) upstream regulatory sequence described in: Okita TW et al., J. Biol Chem. 264: 12573-12581, 1989 and GenBank Accession No. M28156 | 26 |
| *Oryza sativa* prolamin RP6 upstream regulatory sequence described in: Wen TN, et al., Plant Physiol 101: 1115-1116, 1993 and GenBank Accession No. X65064 | 27 |
| *Oryza sativa* prolamin PG5a upstream regulatory sequence described in: Nakase M et al., Plant Mol. Biol. 32: 621-630, 1996 and GenBank Accession No. D73383) | 28 |
| *Oryza sativa* globulin gene Glb promoter sequence (FIG. 9) | 29 |
| *Tricticum aestivum* Bx7 gene promoter sequence (FIG. 10) | 30 |
| the Opaque2 coding sequence found at GenBank Accession No. X15544 (gene) | 31 |
| the Opaque2 coding sequence found at GenBank Accession No. M29411<br>(opaque2 cDNA). | 32 |
| rice PBF coding sequence found at GenBank Accession No. D11385 | 33 |
| maize PBF coding sequence found at GenBank Accession No. ZMU82230 | 34 |
| DNA coding sequence for the rice (*Oryza sativa*) Reb bZIP protein<br>(FIGS. 2A-I) | 35 |

What is claimed is:

1. A method of expressing a heterologous protein in a monocot seed, comprising:

introducing into a monocot plant cell, a first construct containing a nucleotide sequence encoding the heterologous protein and operably linked thereto, a first seed-storage-protein promoter that is activated during seed maturation by the binding of a transcription factor selected from Reb, O2 or PBF to the promoter;

introducing into the cell, a second construct for expressing the transcription factor during seed maturation operably linked to a second seed-storage protein promoter that is activated during seed maturation, and growing the plant from said cell to seed maturation.

2. The method of claim 1, wherein said first seed-storage protein promoter is a monocot endosperm-specific globulin (Glb) promoter identified by SEQ ID NO: 29.

3. The method of claim 1, wherein the first and second seed-storage protein promoters are the same.

4. The method of claim 3, wherein said seed-storage-protein promoter is a monocot endosperm-specific globulin (Glb) promoter identified by SEQ ID NO: 29.

* * * * *